(12) United States Patent
Kerr et al.

(10) Patent No.: US 8,632,525 B2
(45) Date of Patent: Jan. 21, 2014

(54) POWER CONTROL ARRANGEMENTS FOR SURGICAL INSTRUMENTS AND BATTERIES

(75) Inventors: Wendy A. Kerr, Cincinnati, OH (US); Richard F. Schwemberger, Cincinnati, OH (US); Richard L. Leimbach, Cincinnati, OH (US); Brett E. Swensgard, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 319 days.

(21) Appl. No.: 12/884,995

(22) Filed: Sep. 17, 2010

(65) Prior Publication Data

US 2012/0071866 A1 Mar. 22, 2012

(51) Int. Cl.
*A61B 17/00* (2006.01)

(52) U.S. Cl.
USPC ...... 606/1; 606/13; 606/41; 606/47; 600/101; 600/104

(58) Field of Classification Search
USPC .............. 606/1, 13, 27, 32–52; 600/101, 102, 600/104–108; 227/175.1, 175.2
See application file for complete search history.

(56) References Cited

U.S. PATENT DOCUMENTS

| | | | |
|---|---|---|---|
| 5,810,811 A | 9/1998 | Yates et al. | |
| 5,868,790 A | 2/1999 | Vincent et al. | |
| 6,905,057 B2 | 6/2005 | Swayze et al. | |
| 6,978,921 B2 | 12/2005 | Shelton, IV et al. | |
| 7,328,828 B2 | 2/2008 | Ortiz et al. | |
| 7,354,447 B2 | 4/2008 | Shelton, IV et al. | |
| 7,407,078 B2 | 8/2008 | Shelton, IV et al. | |
| 7,416,101 B2 | 8/2008 | Shelton, IV et al. | |
| 7,422,139 B2 | 9/2008 | Shelton, IV et al. | |
| 7,431,189 B2 | 10/2008 | Shelton, IV et al. | |
| 7,434,717 B2 | 10/2008 | Shelton, IV et al. | |
| 7,438,209 B1 | 10/2008 | Hess et al. | |
| 7,441,684 B2 | 10/2008 | Shelton, IV et al. | |
| 7,441,685 B1 | 10/2008 | Boudreaux | |
| 7,448,525 B2 | 11/2008 | Shelton, IV et al. | |
| 7,464,846 B2 | 12/2008 | Shelton, IV et al. | |
| 7,464,849 B2 | 12/2008 | Shelton, IV et al. | |
| 7,467,740 B2 | 12/2008 | Shelton, IV et al. | |
| 7,472,815 B2 | 1/2009 | Shelton, IV et al. | |
| 7,490,749 B2 | 2/2009 | Schall et al. | |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Ahmed Farah

(57) ABSTRACT

Various embodiments are directed to battery unit for use with surgical instruments. The battery units may comprise a plurality of cells and include a translatable discharge drain. When attached to the surgical instrument, the discharge drain may electrically connect an anode of the battery unit to a cathode of the battery unit, for example, via a resistive element in order to drain the battery unit.

20 Claims, 56 Drawing Sheets

(56) References Cited

U.S. PATENT DOCUMENTS

| | | |
|---|---|---|
| 7,500,979 B2 | 3/2009 | Hueil et al. |
| 7,506,791 B2 | 3/2009 | Omaits et al. |
| 7,510,107 B2 | 3/2009 | Timm et al. |
| 7,549,564 B2 | 6/2009 | Boudreaux |
| 7,568,603 B2 | 8/2009 | Shelton, IV et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,644,848 B2 | 1/2010 | Swayze et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,934,630 B2 | 5/2011 | Shelton, IV et al. |
| 7,959,050 B2 | 6/2011 | Smith et al. |
| 2007/0102472 A1 | 5/2007 | Shelton, IV |
| 2007/0106317 A1 | 5/2007 | Shelton, IV et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0167522 A1 | 7/2008 | Giordano et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0237296 A1 | 10/2008 | Boudreaux et al. |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0314957 A1 | 12/2008 | Boudreaux |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0090763 A1 | 4/2009 | Zemlok et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0242610 A1 | 10/2009 | Shelton, Iv et al. |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072252 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |

(56) References Cited

U.S. PATENT DOCUMENTS

| | | | |
|---|---|---|---|
| 2011/0006101 A1 | 1/2011 | Hall et al. | |
| 2011/0006103 A1 | 1/2011 | Laurent et al. | |
| 2011/0011914 A1 | 1/2011 | Baxter, III et al. | |
| 2011/0011915 A1 | 1/2011 | Shelton, IV | |
| 2011/0022032 A1* | 1/2011 | Zemlok et al. | 606/1 |
| 2011/0024477 A1 | 2/2011 | Hall | |
| 2011/0024478 A1 | 2/2011 | Shelton, IV | |
| 2011/0024479 A1 | 2/2011 | Swensgard et al. | |
| 2011/0042441 A1 | 2/2011 | Shelton, IV et al. | |
| 2011/0060363 A1 | 3/2011 | Hess et al. | |
| 2011/0062212 A1 | 3/2011 | Shelton, IV et al. | |
| 2011/0068145 A1 | 3/2011 | Bedi et al. | |
| 2011/0068148 A1 | 3/2011 | Hall et al. | |
| 2011/0084113 A1 | 4/2011 | Bedi et al. | |
| 2011/0084115 A1 | 4/2011 | Bedi et al. | |
| 2011/0087276 A1 | 4/2011 | Bedi et al. | |
| 2012/0071711 A1* | 3/2012 | Shelton et al. | 600/104 |
| 2012/0080477 A1* | 4/2012 | Leimbach et al. | 227/175.2 |
| 2013/0103024 A1* | 4/2013 | Monson et al. | 606/33 |

FOREIGN PATENT DOCUMENTS

| | | |
|---|---|---|
| CA | 2514274 A1 | 1/2006 |
| DE | 273689 C | 5/1914 |
| DE | 1775926 A | 1/1972 |
| DE | 3210466 A1 | 9/1983 |
| DE | 9412228 U | 9/1994 |
| DE | 19924311 A1 | 11/2000 |
| DE | 69328576 T2 | 1/2001 |
| DE | 20112837 U1 | 10/2001 |
| DE | 20121753 U1 | 4/2003 |
| DE | 10314072 A1 | 1/2006 |
| EP | 0122046 A1 | 10/1984 |
| EP | 0070230 B1 | 10/1985 |
| EP | 0033548 B1 | 5/1986 |
| EP | 0276104 A2 | 7/1988 |
| EP | 0639349 A2 | 2/1994 |
| EP | 0324636 B1 | 3/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0676173 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0741996 B1 | 2/2004 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1157666 B1 | 9/2005 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1652481 A2 | 5/2006 |
| EP | 1382303 B1 | 6/2006 |
| EP | 1045672 B1 | 8/2006 |
| EP | 1617768 B1 | 8/2006 |
| EP | 1702567 A2 | 9/2006 |
| EP | 1129665 B1 | 11/2006 |
| EP | 1400206 B1 | 11/2006 |
| EP | 1256317 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1769756 A1 | 4/2007 |
| EP | 1769758 A1 | 4/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1839596 A1 | 10/2007 |
| EP | 1402821 B1 | 12/2007 |
| EP | 1872727 A1 | 1/2008 |
| EP | 1897502 A1 | 3/2008 |
| EP | 1702568 B1 | 7/2008 |
| EP | 1970014 A1 | 9/2008 |
| EP | 1980213 A2 | 10/2008 |
| EP | 1759645 B1 | 11/2008 |
| EP | 1693008 B1 | 12/2008 |
| EP | 1759640 B1 | 12/2008 |
| EP | 2000102 A2 | 12/2008 |
| EP | 1749486 B1 | 3/2009 |
| EP | 2090256 A2 | 8/2009 |
| EP | 1813206 B1 | 4/2010 |
| EP | 1769754 B1 | 6/2010 |
| EP | 1702570 B1 | 10/2010 |
| FR | 999646 A | 2/1952 |
| FR | 1112936 A | 3/1956 |
| FR | 2765794 | 1/1999 |
| GB | 939929 A | 10/1963 |
| GB | 1210522 A | 10/1970 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |

(56) References Cited

FOREIGN PATENT DOCUMENTS

| | | |
|---|---|---|
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/22055 A1 | 7/1996 |
| WO | WO 96/35464 A1 | 11/1996 |
| WO | WO 97/34533 A1 | 9/1997 |
| WO | WO 97/39688 A2 | 10/1997 |
| WO | WO 98/17180 A1 | 4/1998 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/010482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |
| WO | WO 2008/109125 A1 | 9/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
U.S. Appl. No. 12/884,838, filed Sep. 17, 2010.
International Search Report for PCT/US2011/051357, dated Oct. 15, 2012 (7 pages).
International Preliminary Report on Patentability for PCT/US2011/051357, dated Mar. 19, 2013 (14 pages).

* cited by examiner

POWER CONTROL ARRANGEMENTS FOR SURGICAL INSTRUMENTS AND BATTERIES

BACKGROUND

A growing number of surgical instruments are powered by one or more battery cells. Such instruments include a variety of electrically powered implements and may be used in a variety of surgical environments. Battery-powered surgical instruments may include motor-driven implements, such as cutters, graspers, and/or staplers, for example. Battery-powered surgical instruments may also include non-motor driven implements, such as RF cutter/coagulators, ultrasonic cutter/coagulators, and/or laser cutter/coagulators, for example. Battery-powered instruments are also used now in various different surgical environments including, for example, endoscopic environments, laparoscopic environments, and open environments.

Battery-powered surgical instruments often utilize primary cells, which are pre-charged and often intended for a single discharge (e.g., one use). Using single discharge cells avoids the difficulties associated with re-sterilizing and recharging cells. Primary cells, however, present challenges related to shipping, storage and disposal. For example, charged cells can result in hazardous waste if not properly discharged since they may be only used once and still have significant amount of charge left. To mitigate the-risks, many jurisdictions have regulations governing the conditions under which cells may be shipped and disposed. Cells and batteries with higher amounts of stored energy are required to be shipped, stored, and disposed of with safety measures that are more stringent and often more expensive.

SUMMARY

Various embodiments may be directed to a surgical instrument having an end effector and a handle operatively coupled to the end effector. The handle may have a trigger to actuate the end effector and a battery dock that has a protruding member. The surgical instrument may include a battery unit attachable to the battery dock, where the battery unit is in electrical contact with at least one of the handle and the end effector when attached to the battery dock. The battery unit may have a casing and a first anode and a first cathode positioned within the casing. The battery unit may also have a translatable discharge drain, where, upon attachment of the battery unit to the battery dock, the protruding member contacts the discharge drain and the discharge drain translates with respect to casing to electrically couple the first anode of the battery unit to the first cathode of the battery.

Also, various embodiments may be directed to a surgical instrument having a battery compartment. The surgical instrument may have a protruding member positioned proximate the battery compartment a battery unit. The battery unit may have a casing and a plurality of cells positioned within the casing, where at least a portion of the plurality of cells are not electrically connected to one another. The battery unit may have a discharge switch having an open position and a closed position, where, when in the closed position, the discharge switch electrically couples an anode of the battery unit to a cathode of the battery unit. The discharge switch may be mechanically biased towards the closed position, where the discharge switch is held in the open position by a non-conductive portion of the casing. The discharge switch may be translated into the closed position by the protruding member upon attachment of the battery unit into the battery compartment of the surgical instrument.

Additionally, various embodiments may be directed to a surgical system having a surgical device having a battery dock. The surgical system may also have a battery unit, where the battery unit has a first and second grouping of cells and a translatable battery drain positioned proximate the first and second grouping of cells. The translatable battery drain may have a first and second set of contacts; where, in a first position, the first and second set of contacts are not electrically coupled to first and second grouping of cells. In a second position, the first set of contacts may be electrically coupled to the first grouping of cells and the second set of contacts is electrically coupled to the second grouping of cells. The translatable battery drain may translate from the first position to the second position upon attachment of the battery unit to the battery dock.

DRAWINGS

The features of the various embodiments are set forth with particularity in the appended claims. The various embodiments, however, both as to organization and methods of operation, together with advantages thereof, may best be understood by reference to the following description, taken in conjunction with the accompanying drawings as follows:

Figure 23A:
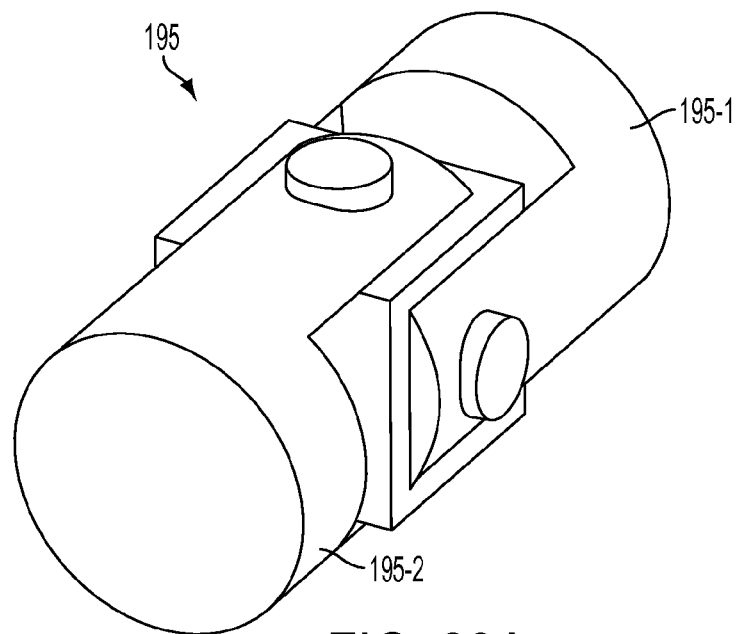
Figure 23B:
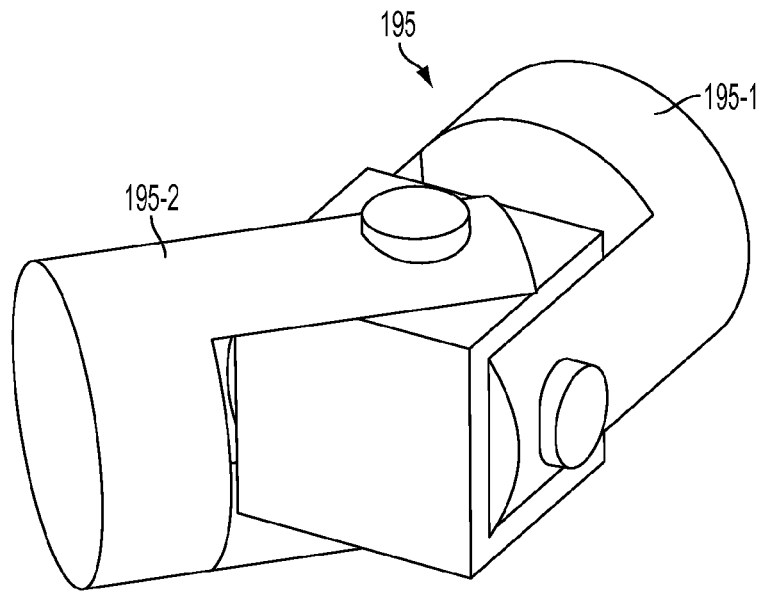

FIGS. 23A-B show one embodiment of a universal joint ("u-joint") that may be employed at the articulation point of a surgical instrument.

Figure 24A:
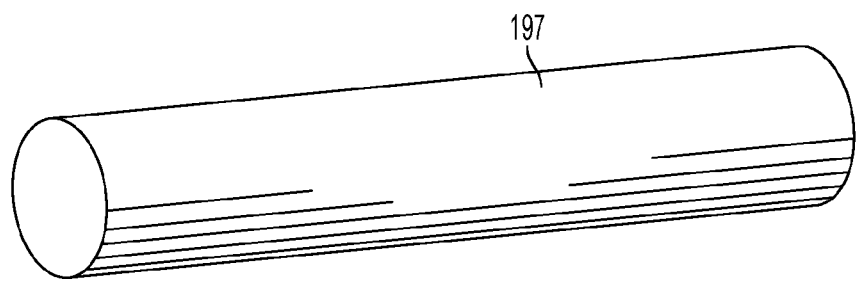
Figure 24B:
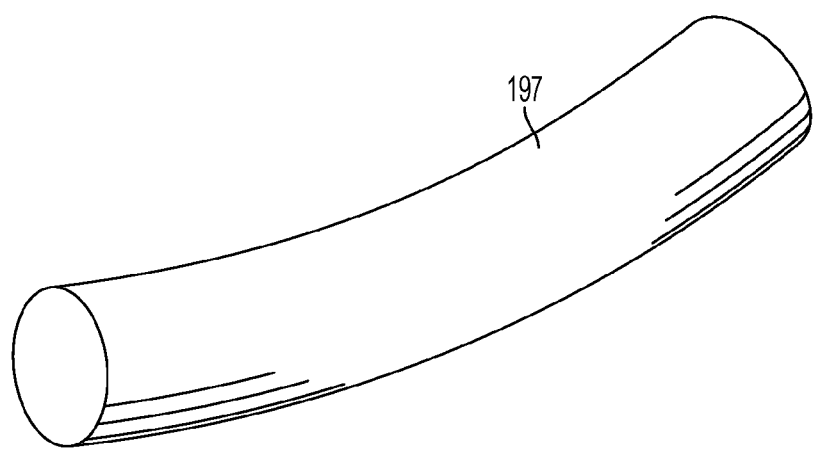
Figure 25:
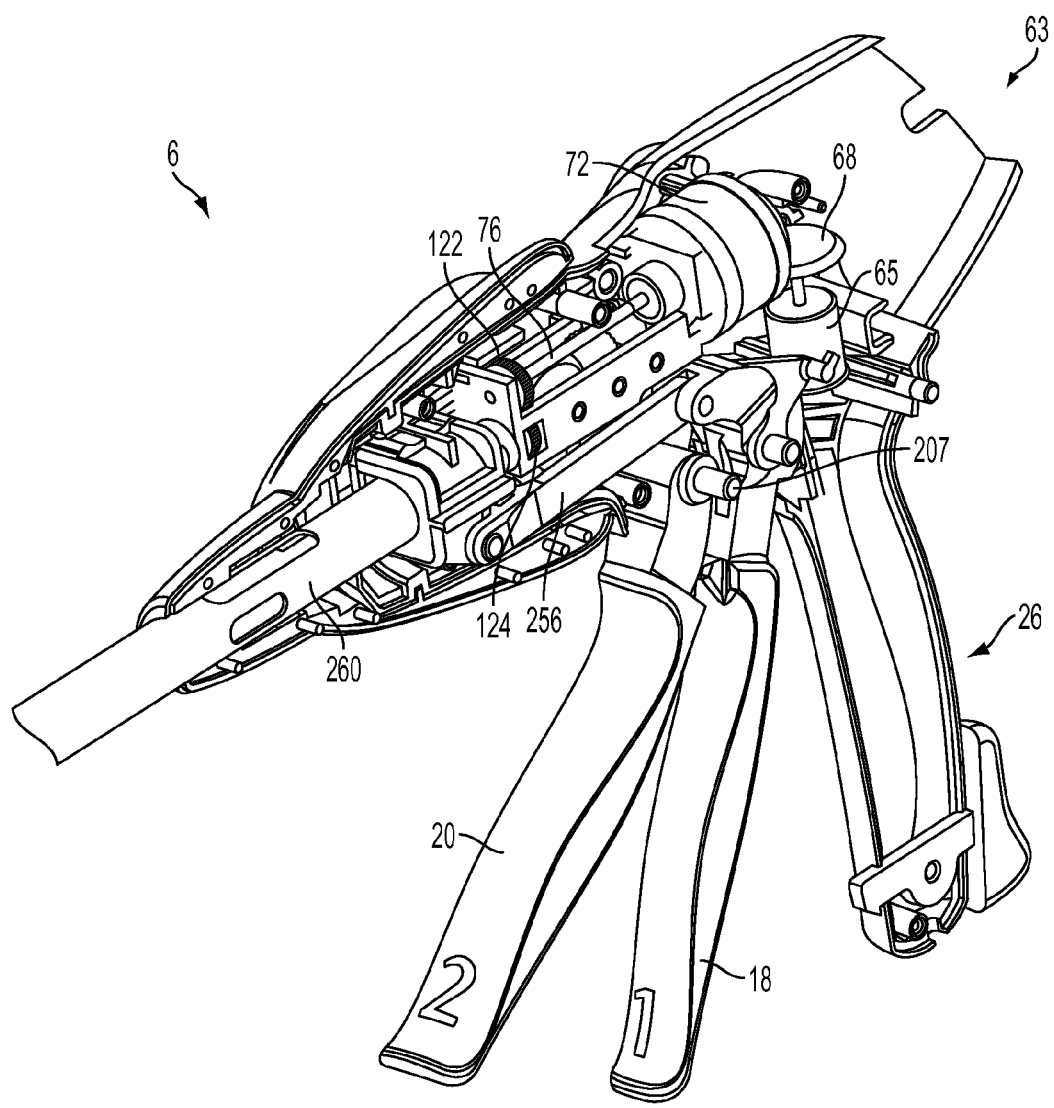
Figure 26:
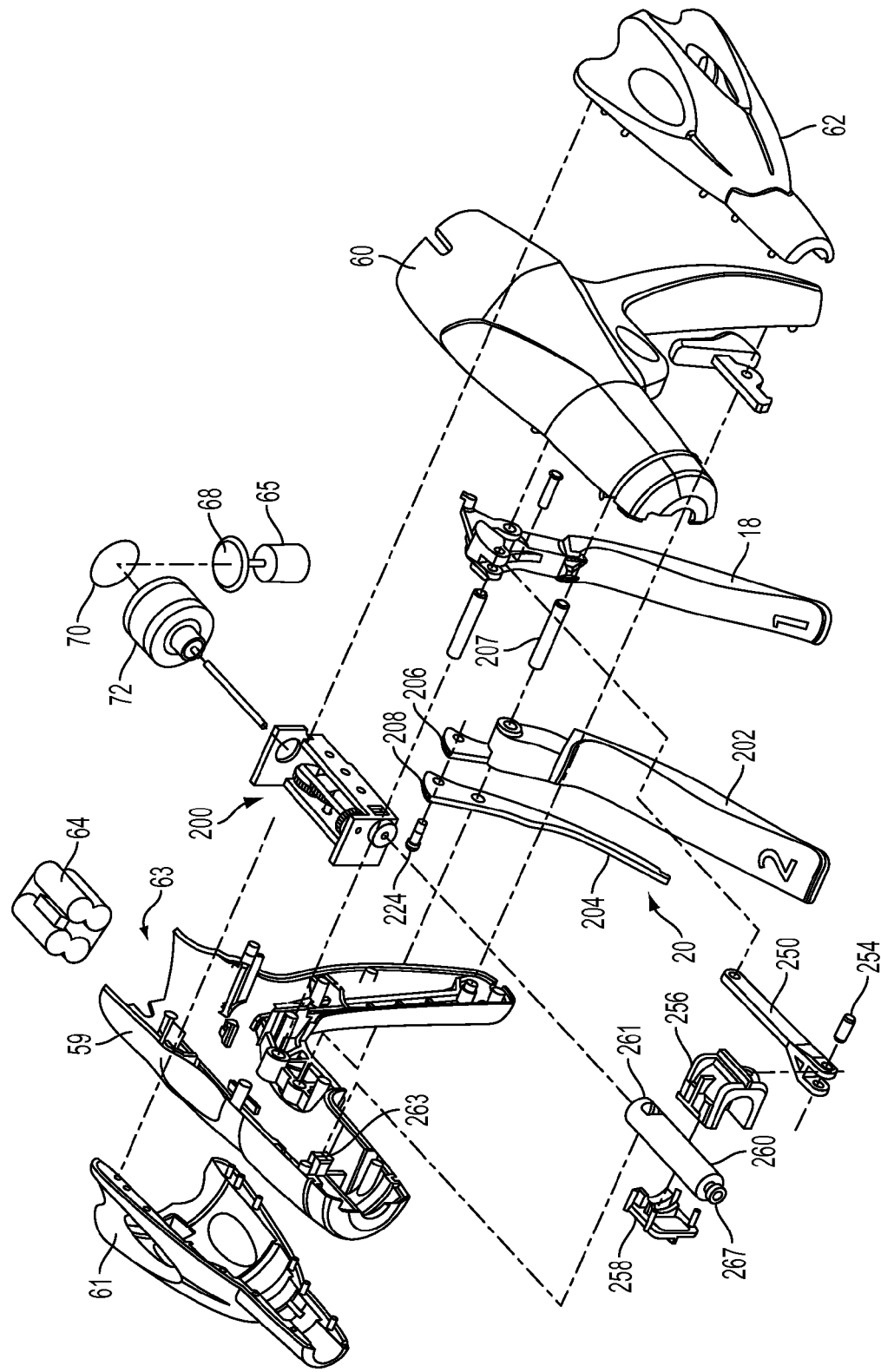
Figure 27:
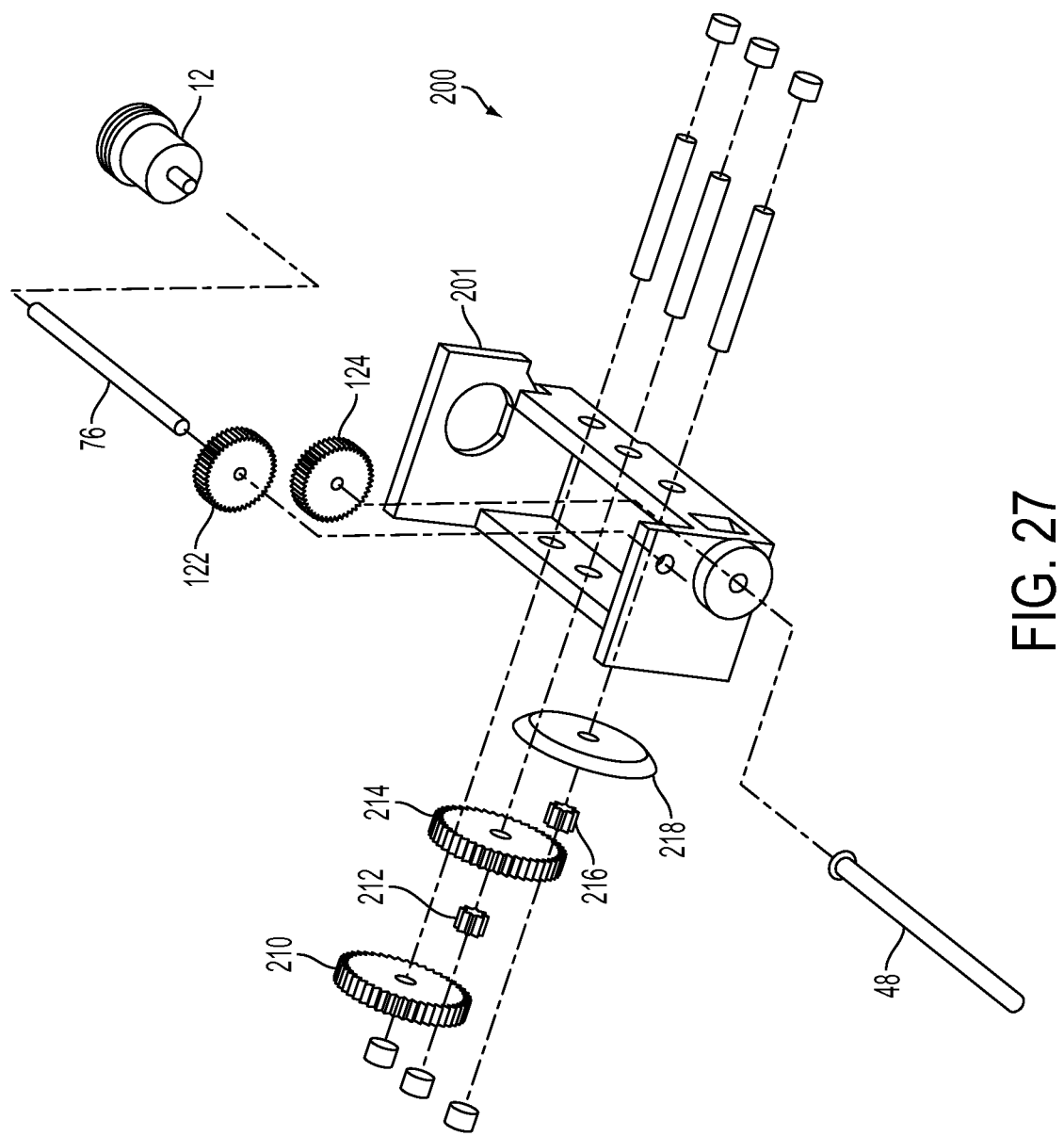
Figure 28:
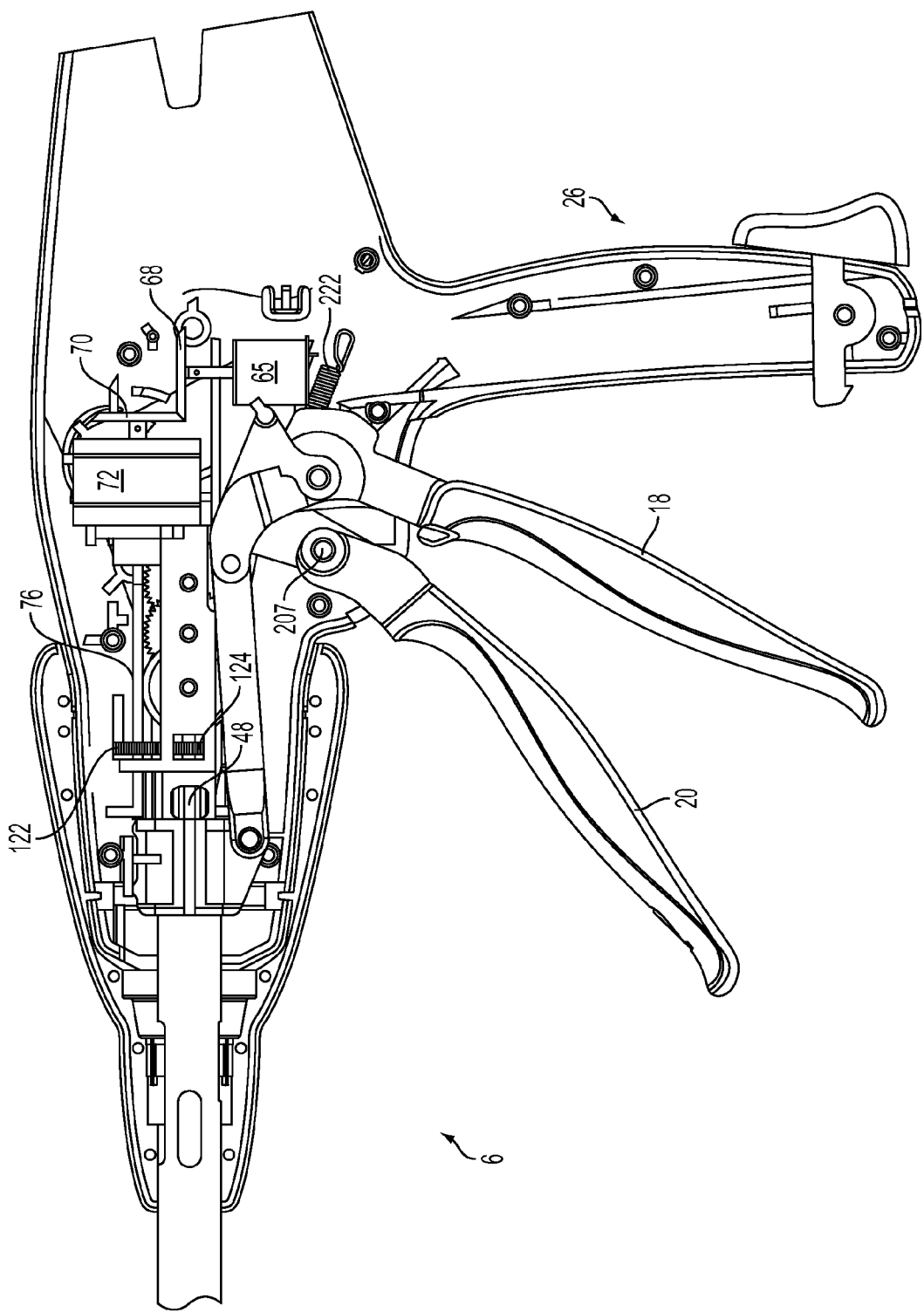
Figure 29:
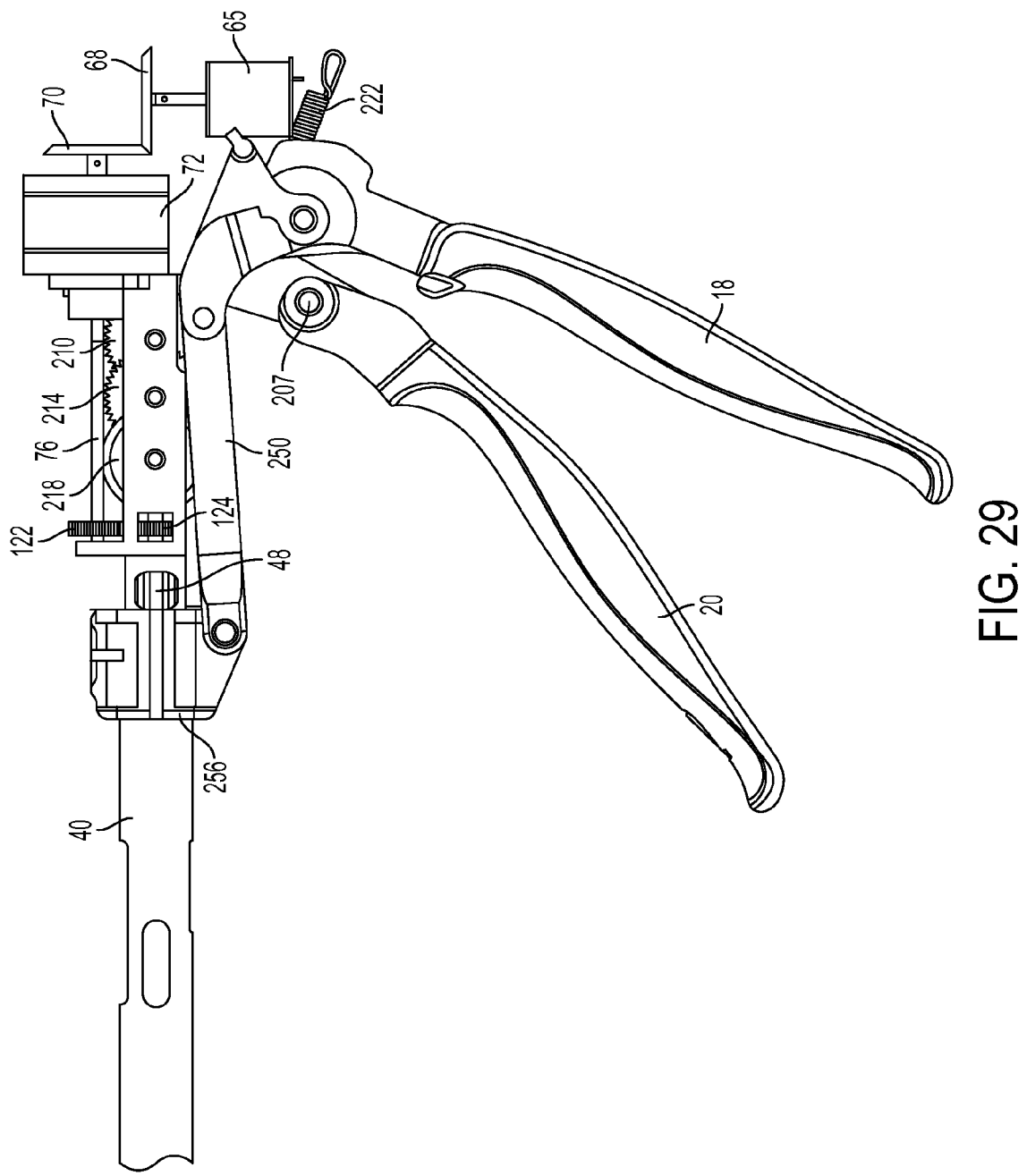
Figure 30:
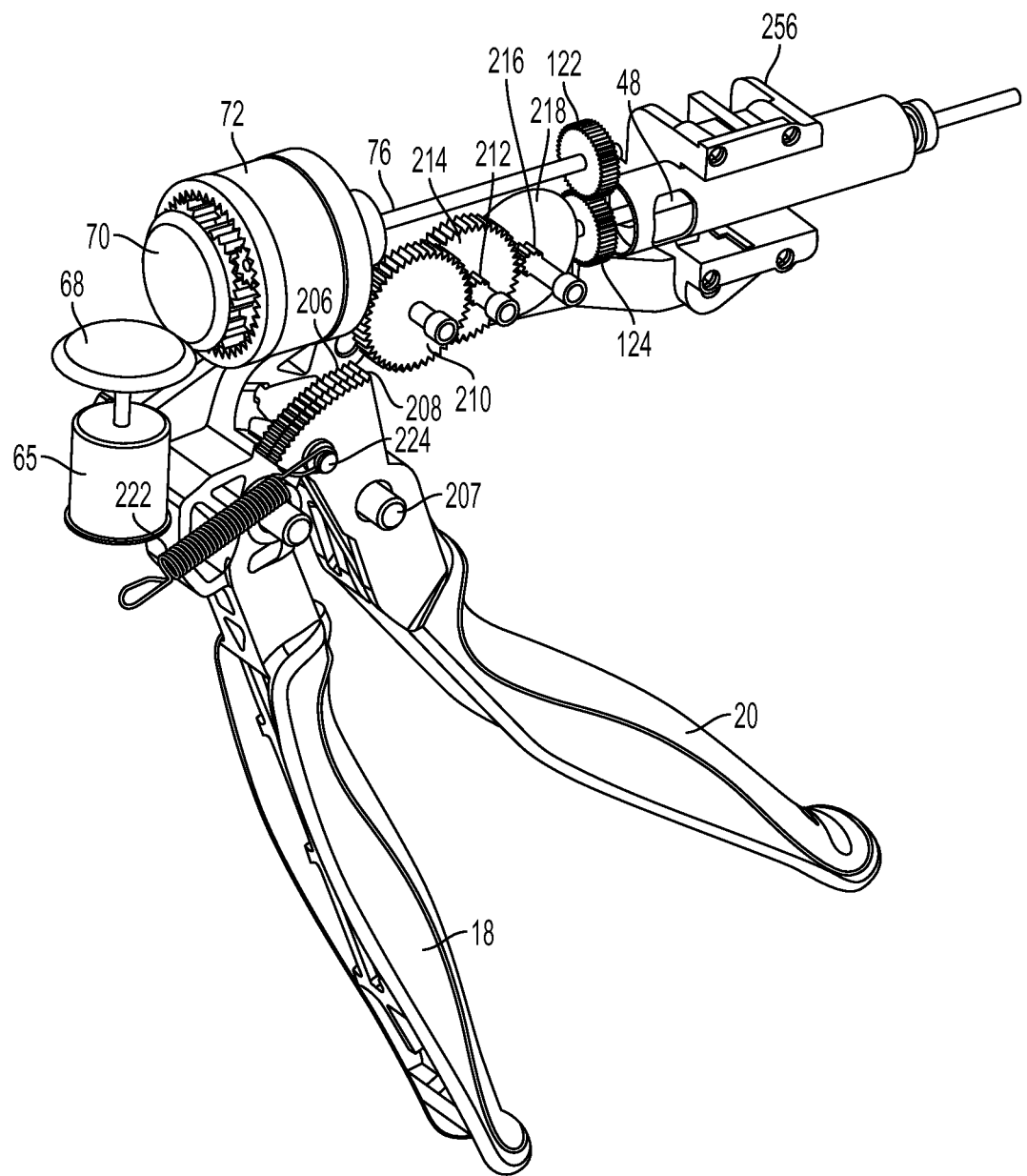
Figure 31:
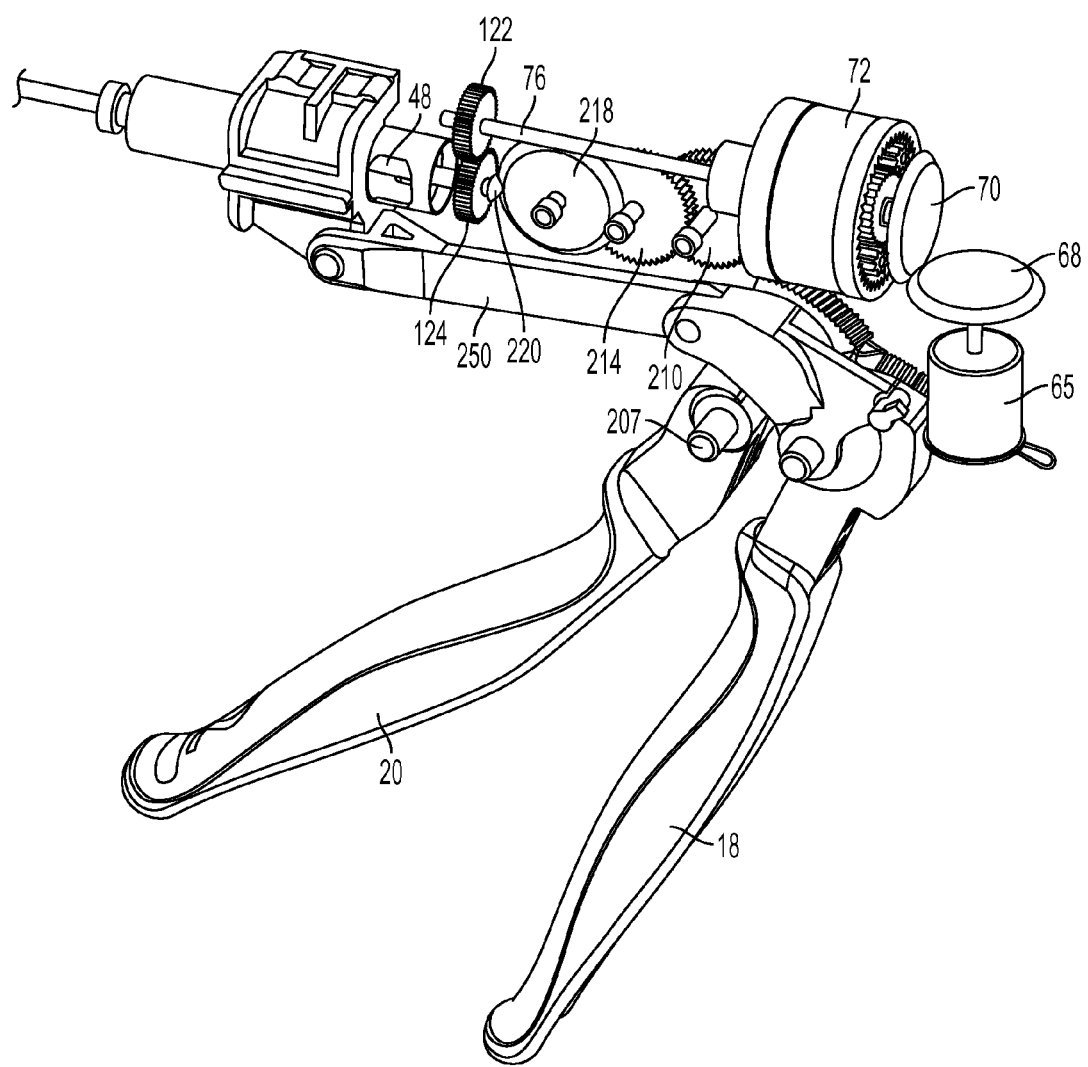

FIGS. 24A-B show one embodiment of a torsion cable that may be employed at an articulation point of a surgical instrument.

FIGS. 25-31 illustrate another embodiment of a motorized, two-stroke surgical cutting and fastening instrument with power assist.

FIGS. 32-36 illustrate one embodiment of a two-stroke, motorized surgical cutting and fastening instrument with power assist.

FIGS. 37-40 illustrate one embodiment of a motorized surgical cutting and fastening instrument with such a tactile position feedback system.

Figure 41:
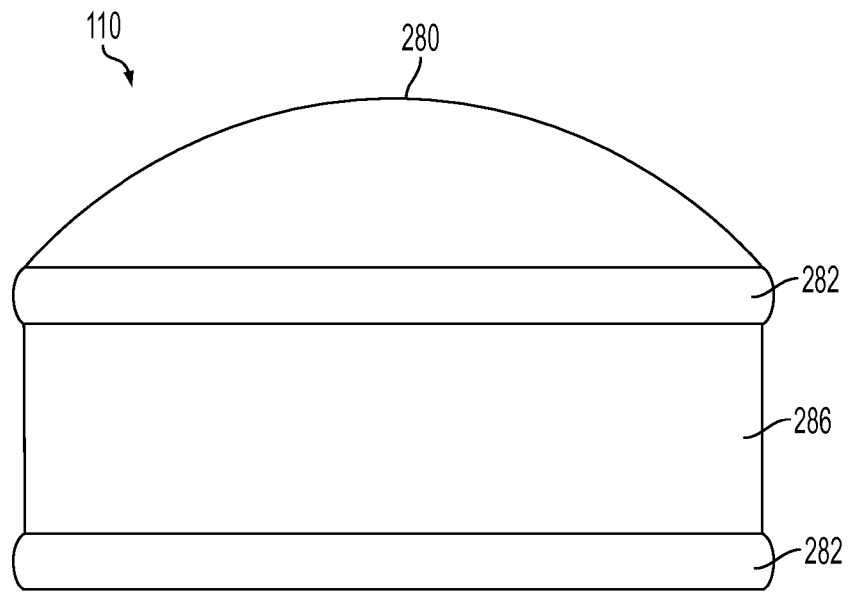
Figure 42:
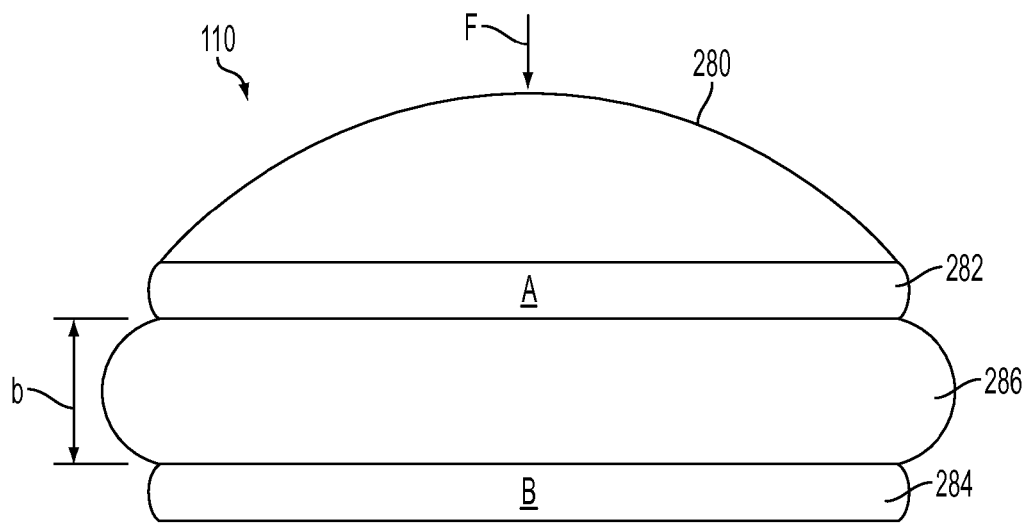

FIGS. 41 and 42 illustrate two states of one embodiment of a variable sensor that may be used as the run motor sensor.

Figure 43:
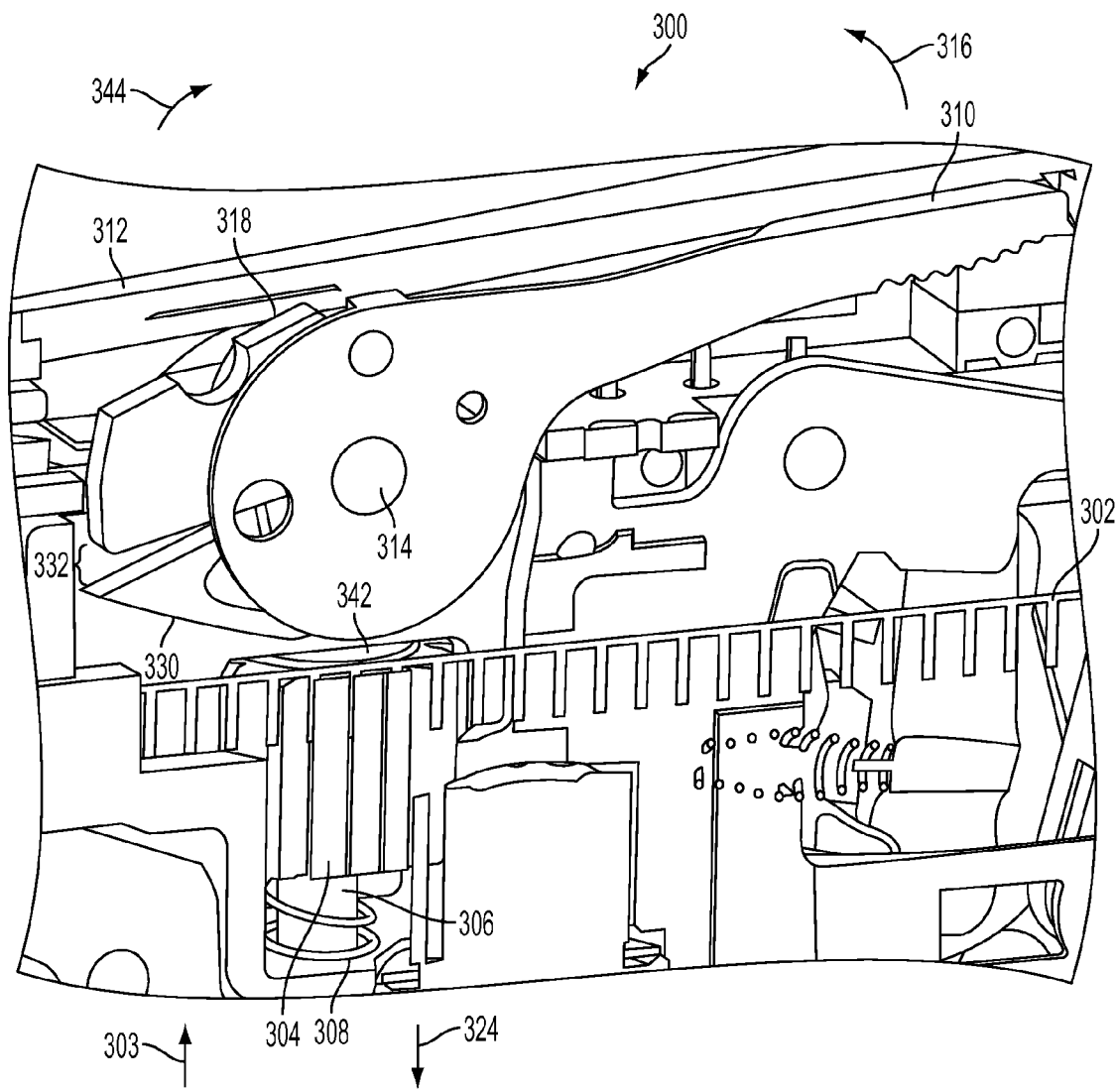

FIG. 43 is a partial cross-sectional view of a surgical instrument with various components removed for clarity.

Figure 44A:
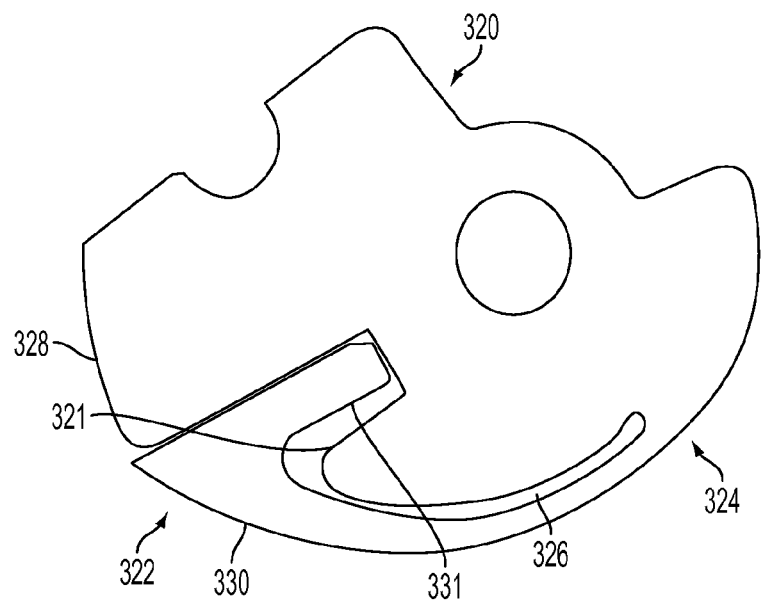

FIGS. 44A and 4B illustrate a locking cam during various states of operation

Figure 45C:
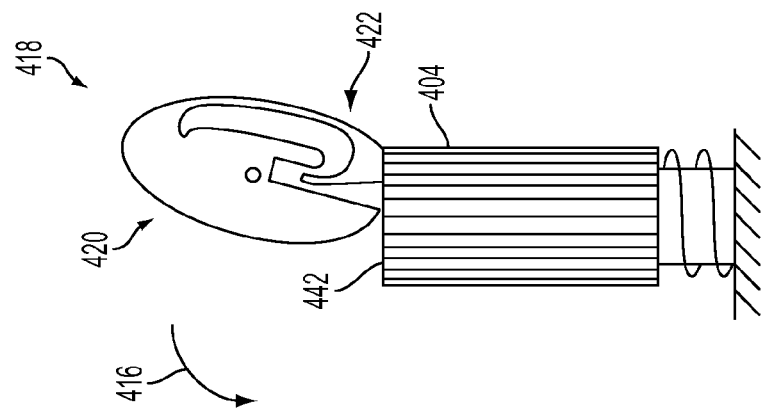
Figure 45B:
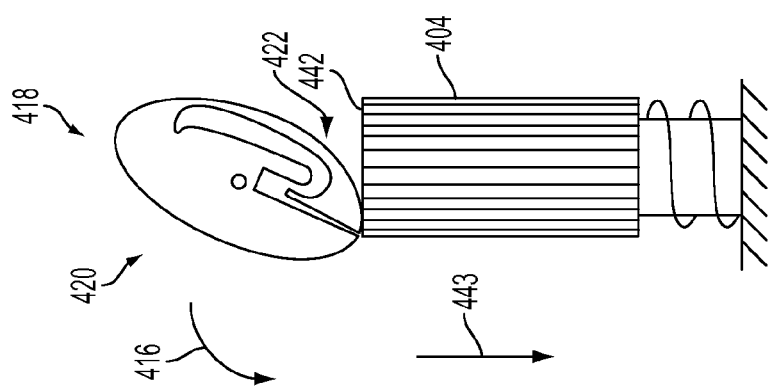
Figure 45A:
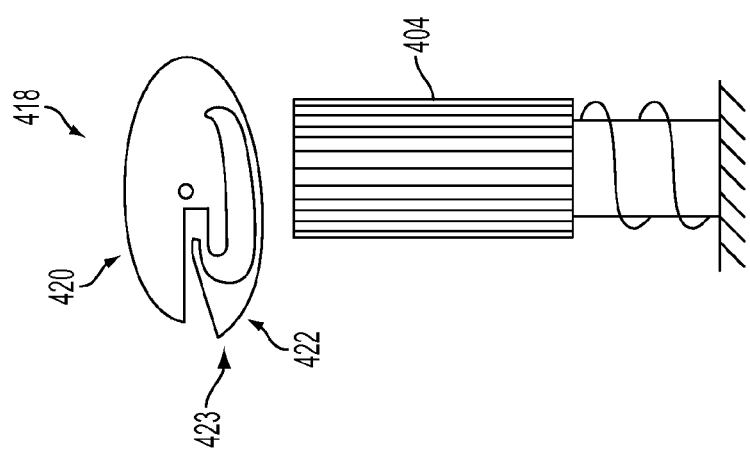

FIGS. 45A, 45B and 45C show a locking cam and a gear during various stages of operation.

Figure 46:
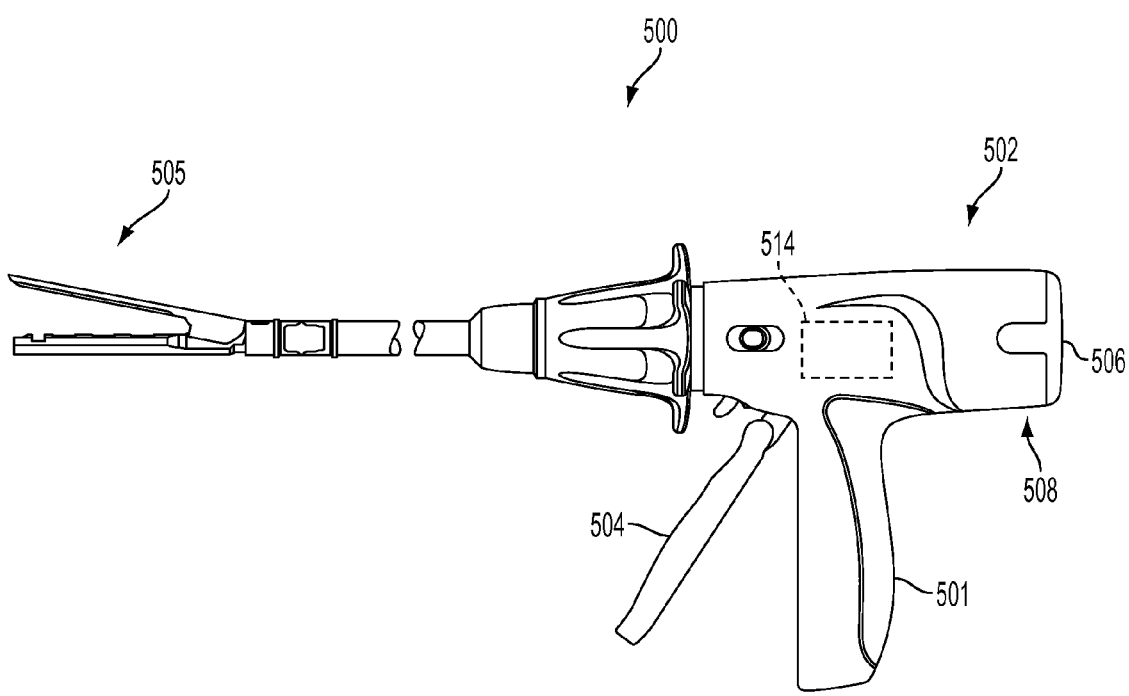

FIG. 46 illustrates one embodiment of a surgical instrument.

Figure 47A:
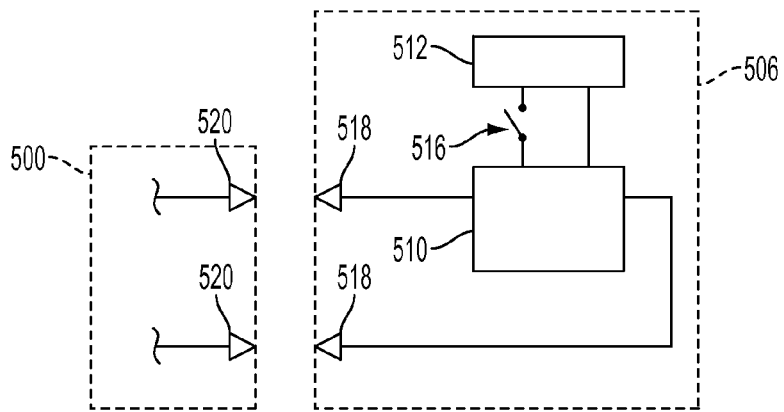
Figure 47B:
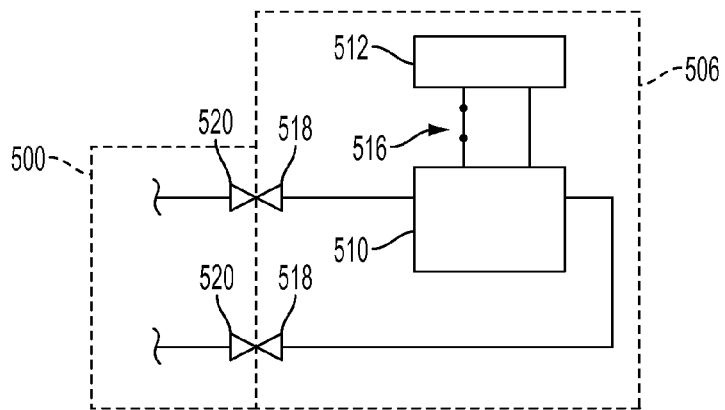
Figure 47C:
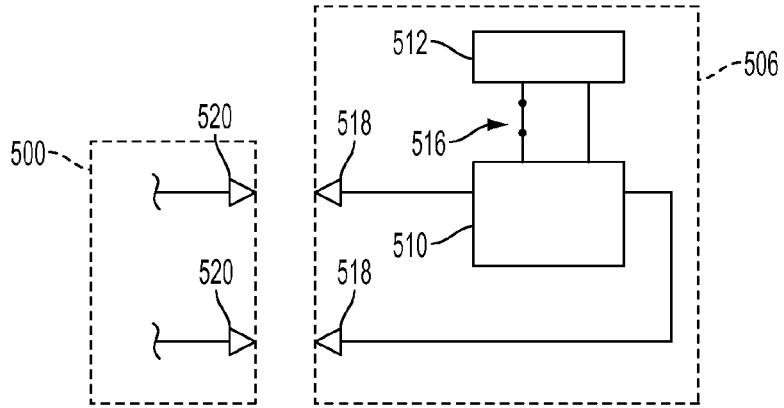

FIGS. 47A, 47B and 47C schematically illustrate the attachment and detachment of a battery unit to an instrument.

Figure 48:
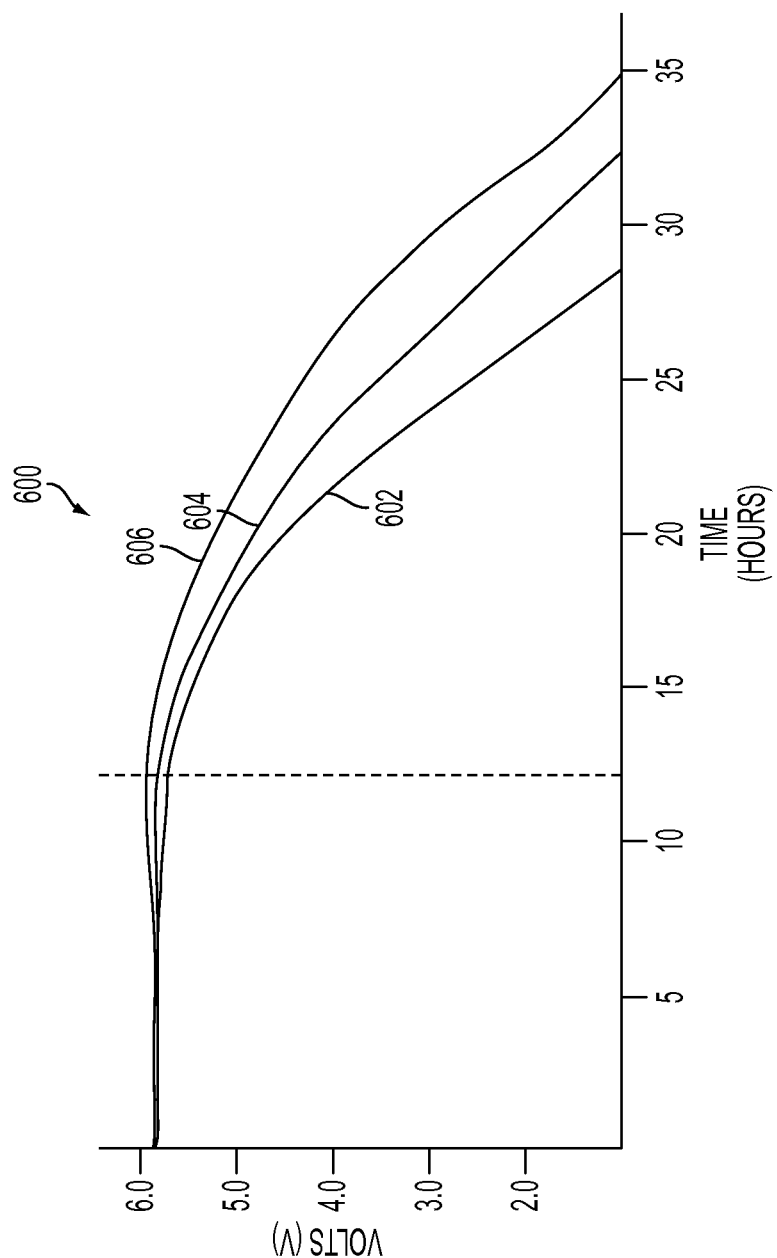

FIG. 48 is a graph of the voltage level of a battery unit over time, as measured from the time of attachment to the instrument, in accordance with one non-limiting embodiment.

Figure 49A:
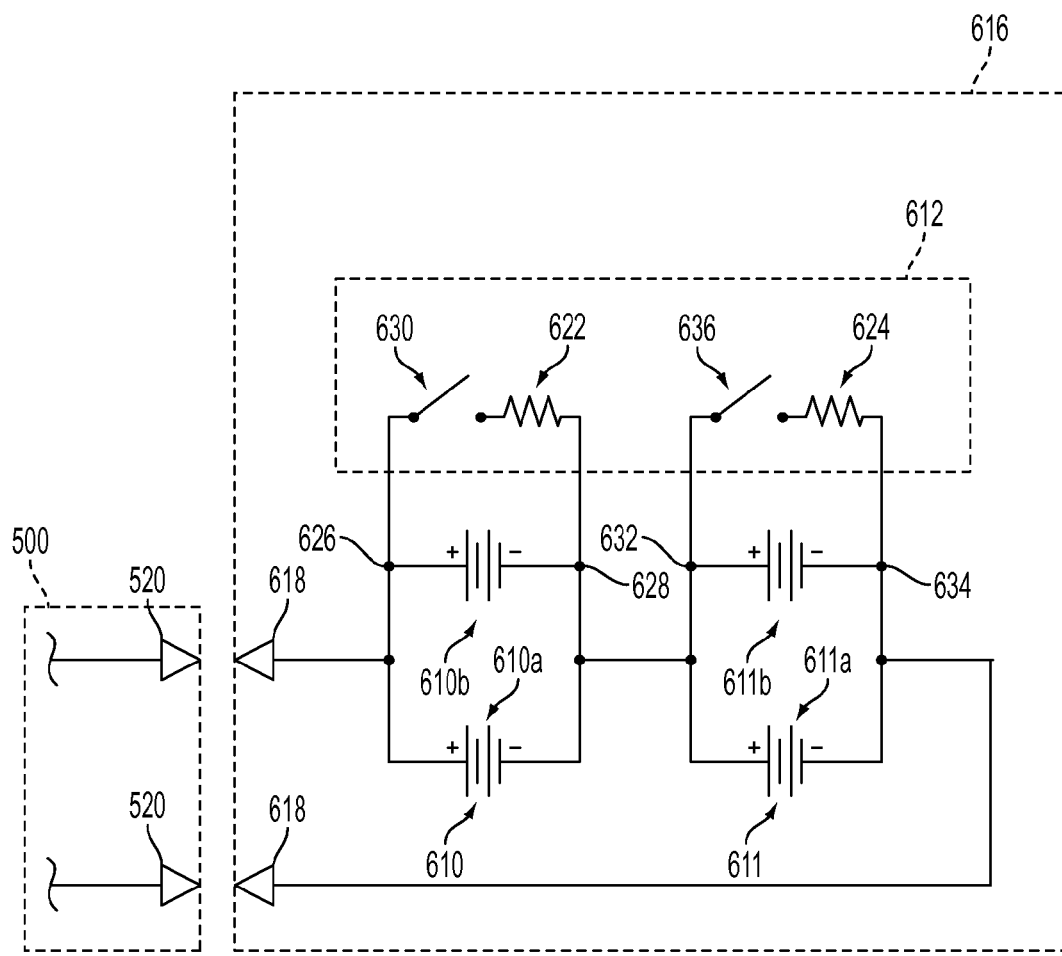

FIG. 49A is one embodiment of a simplified circuit diagram of a battery unit comprising a drain.

Figure 49B:
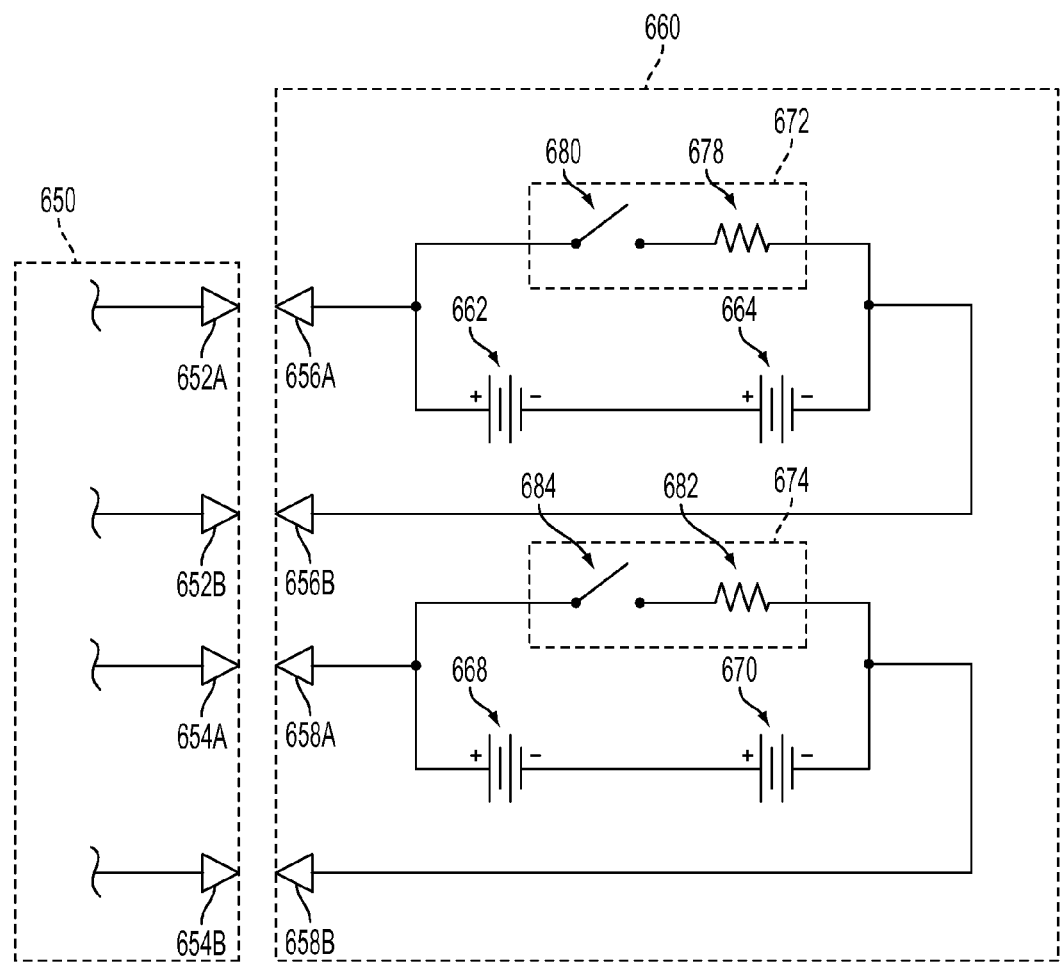
Figure 50:
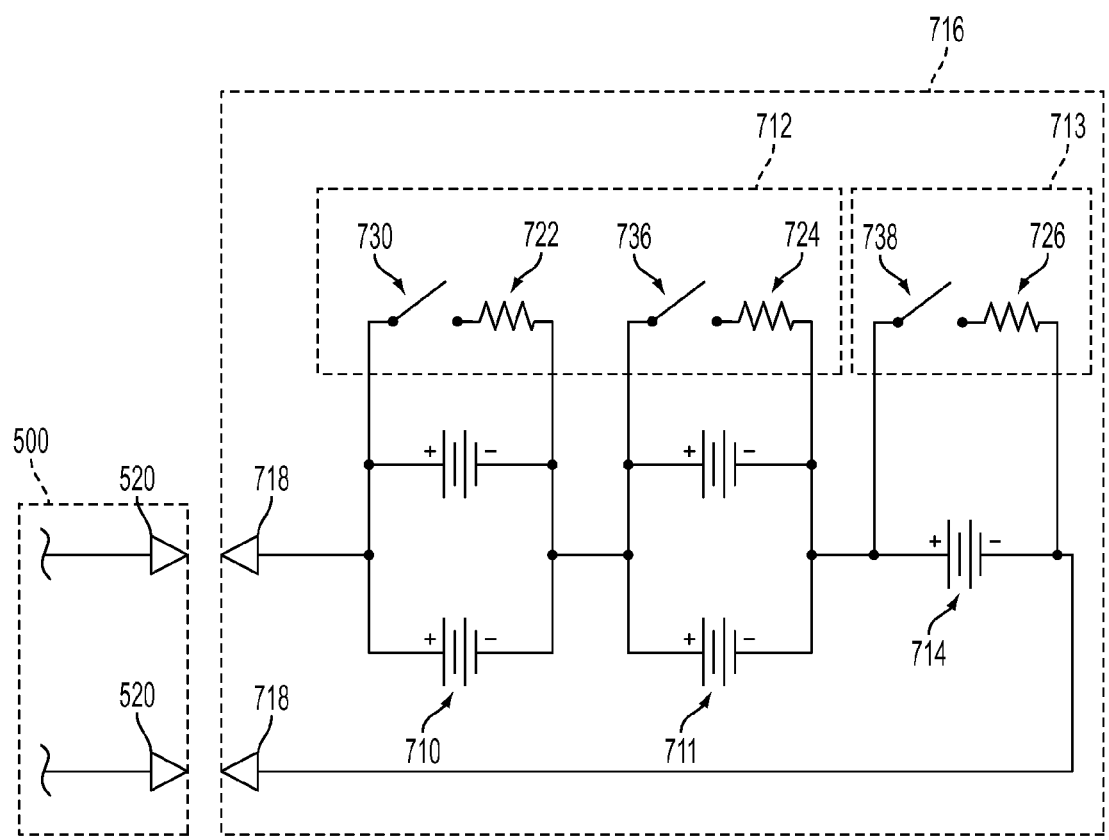

FIG. 49B is another embodiment of a simplified circuit diagram of a battery unit comprising a drain FIG. 50 is one embodiment of a simplified circuit diagram of a battery unit comprising a first drain and a second drain.

Figure 51:
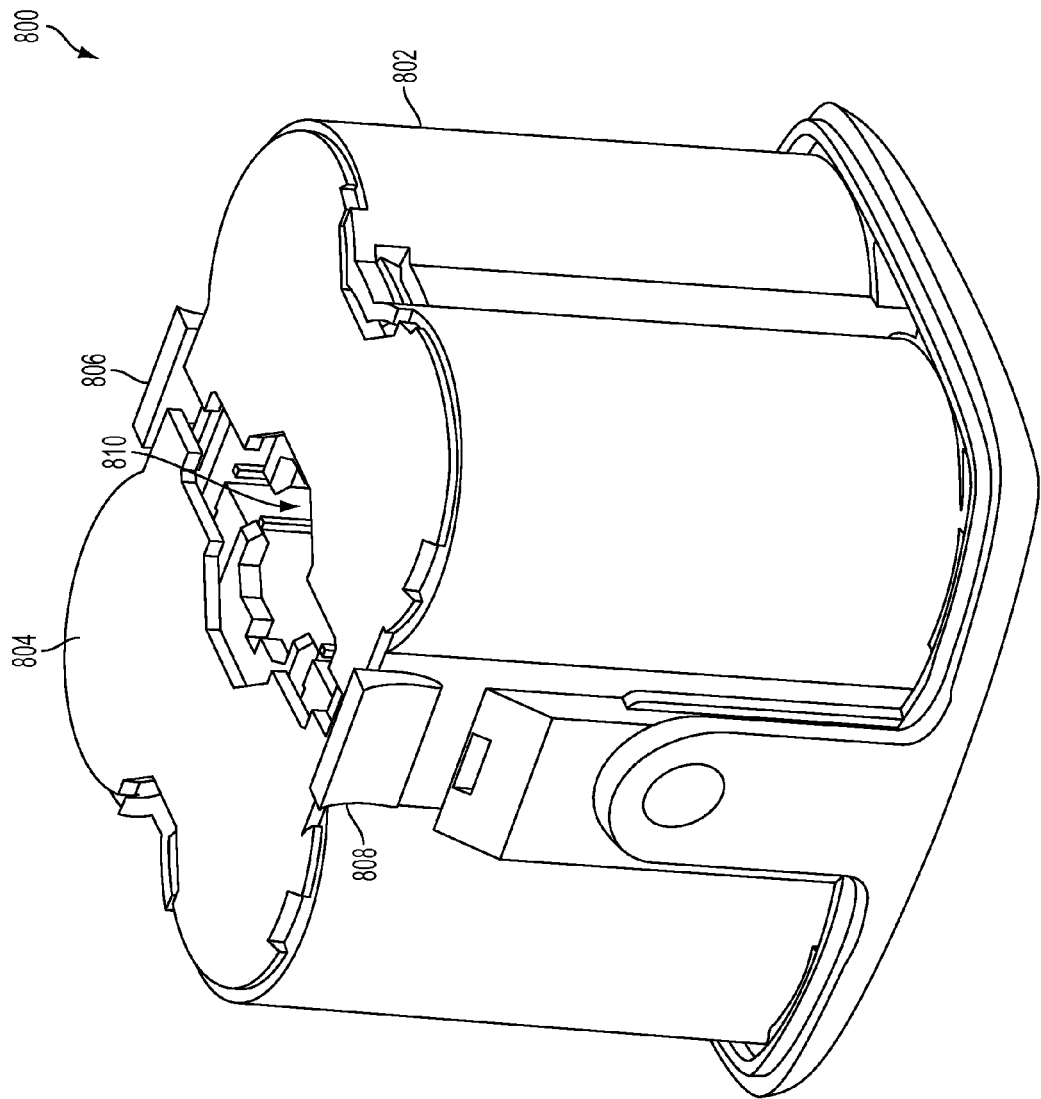
Figure 52:
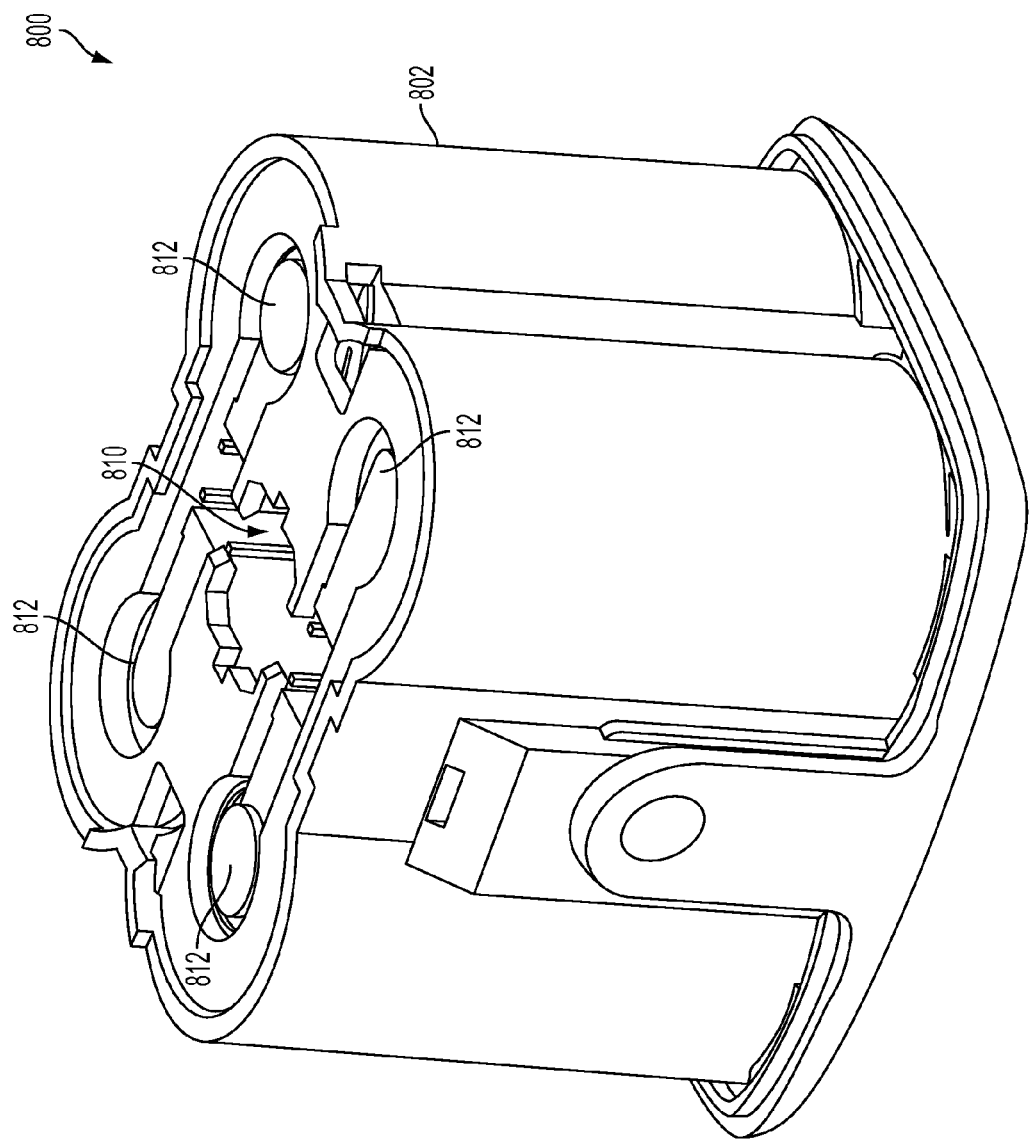
Figure 53:
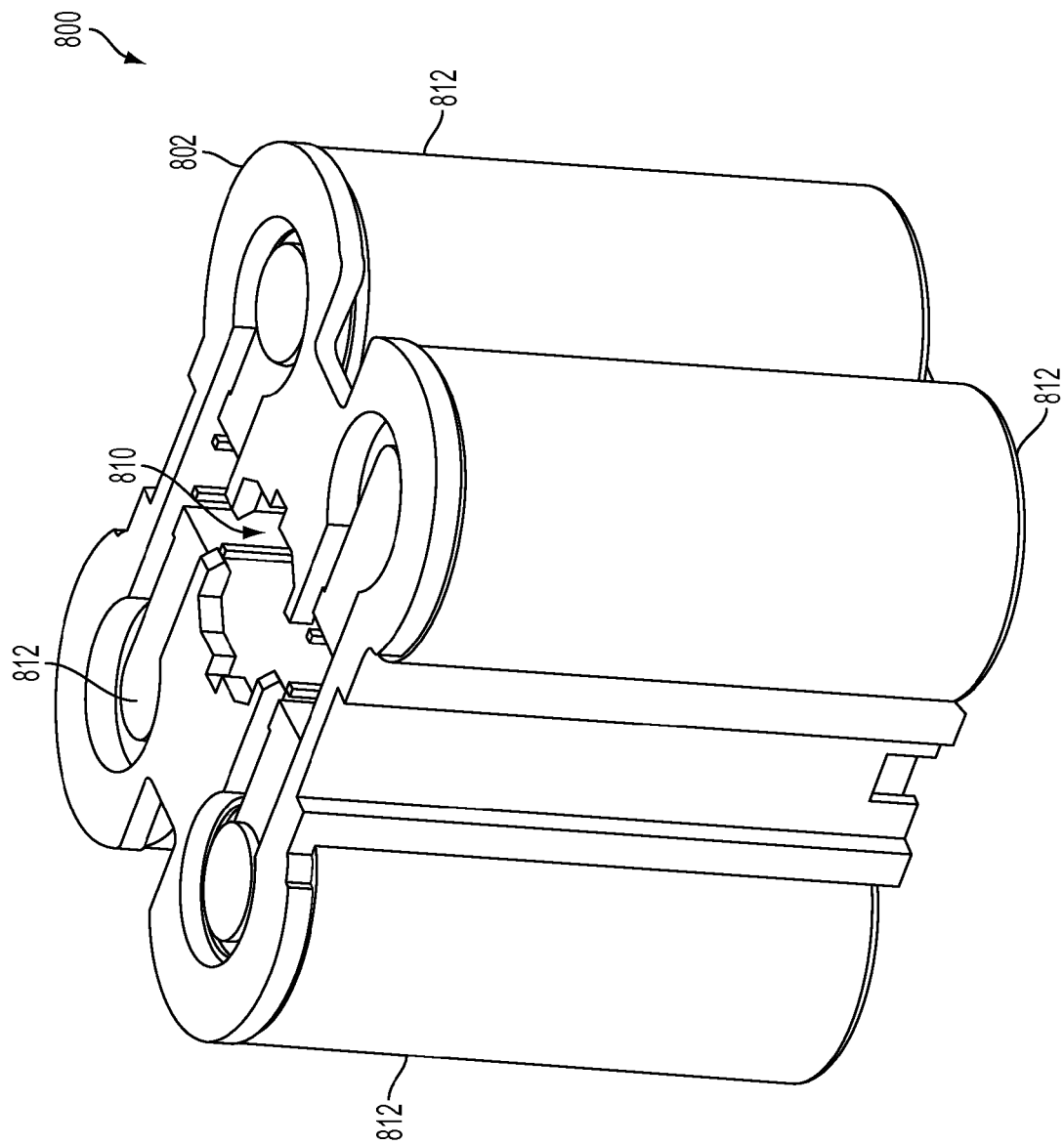

FIGS. 51-53 are perspective views of one embodiment of a battery unit.

Figure 54A:
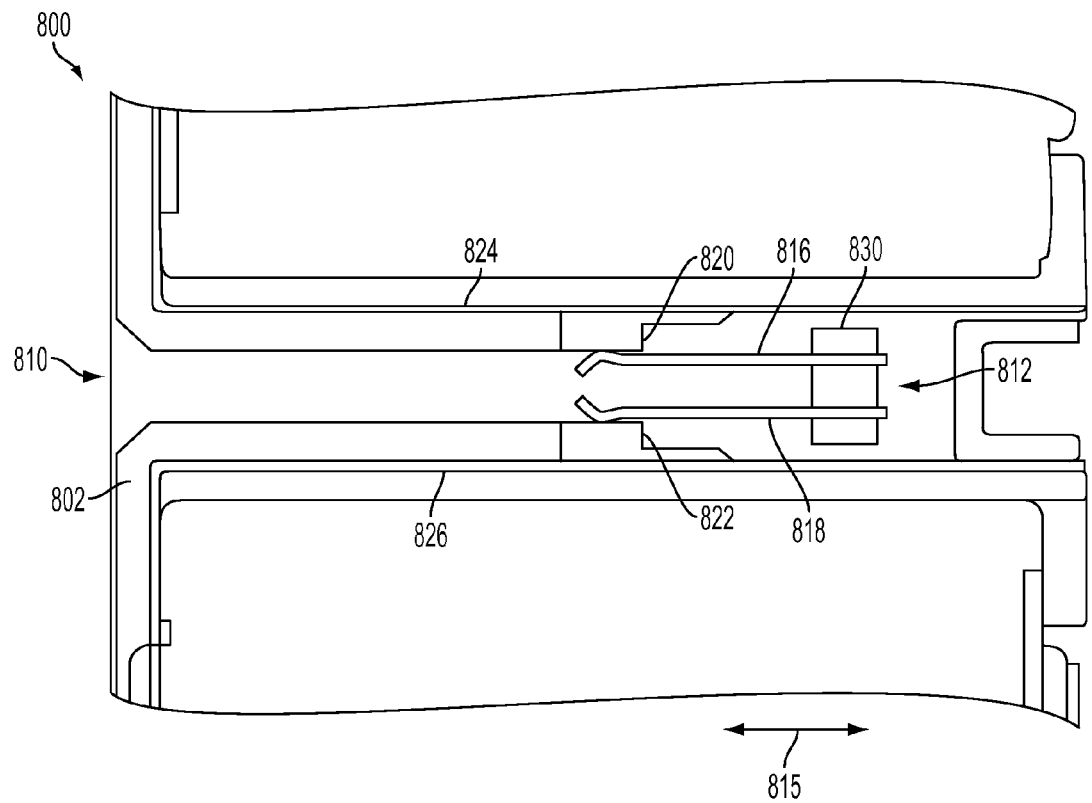
Figure 54B:
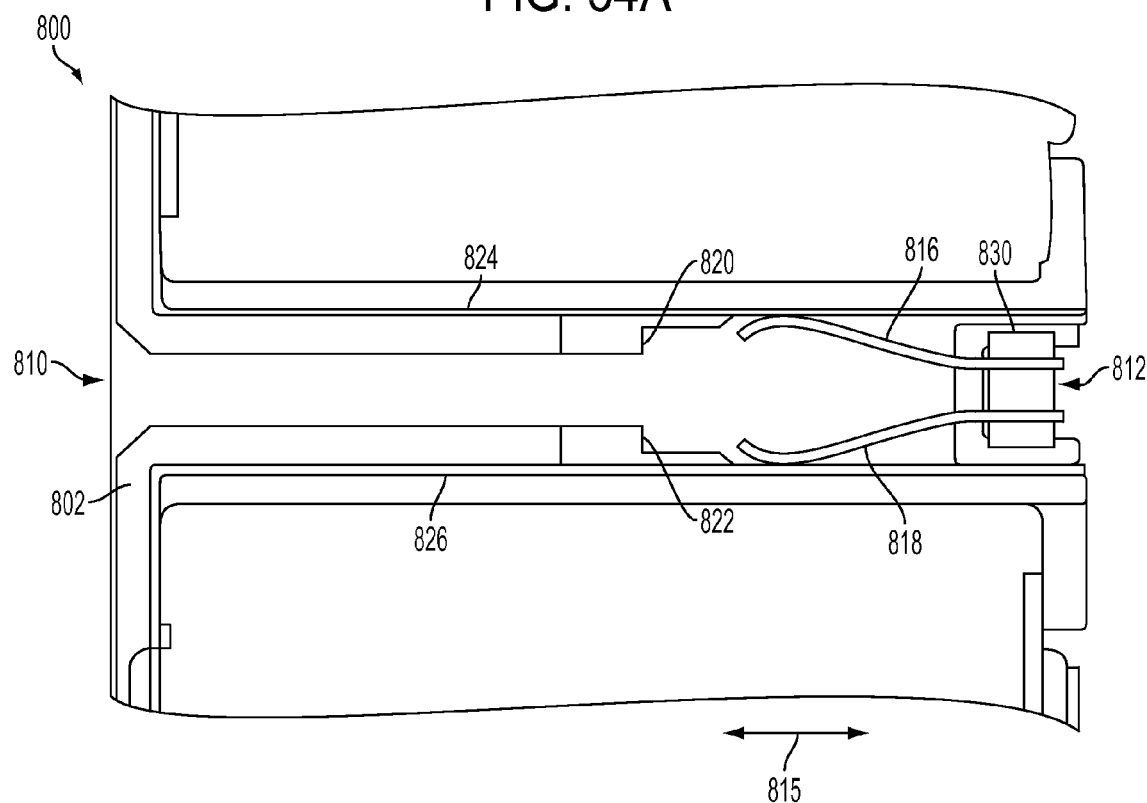

FIGS. 54A and 54B illustrate cross-sectional views of one embodiment of a battery unit including a translatable drain.

Figure 55:
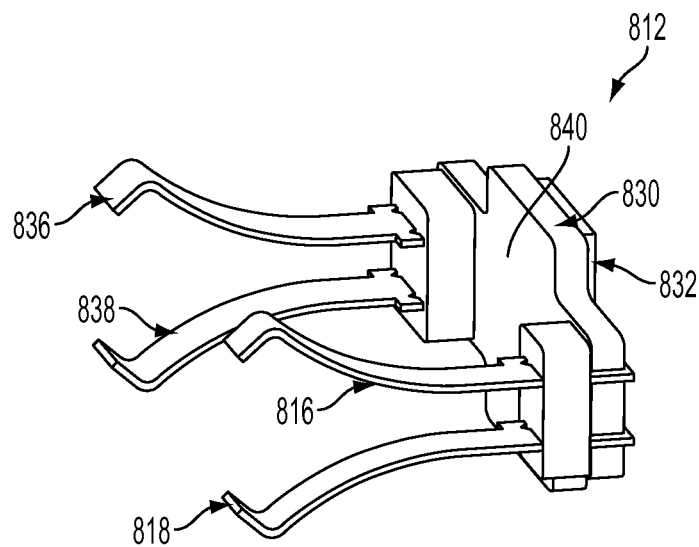

FIG. 55 is a perspective view of one embodiment of a drain.

Figure 56:
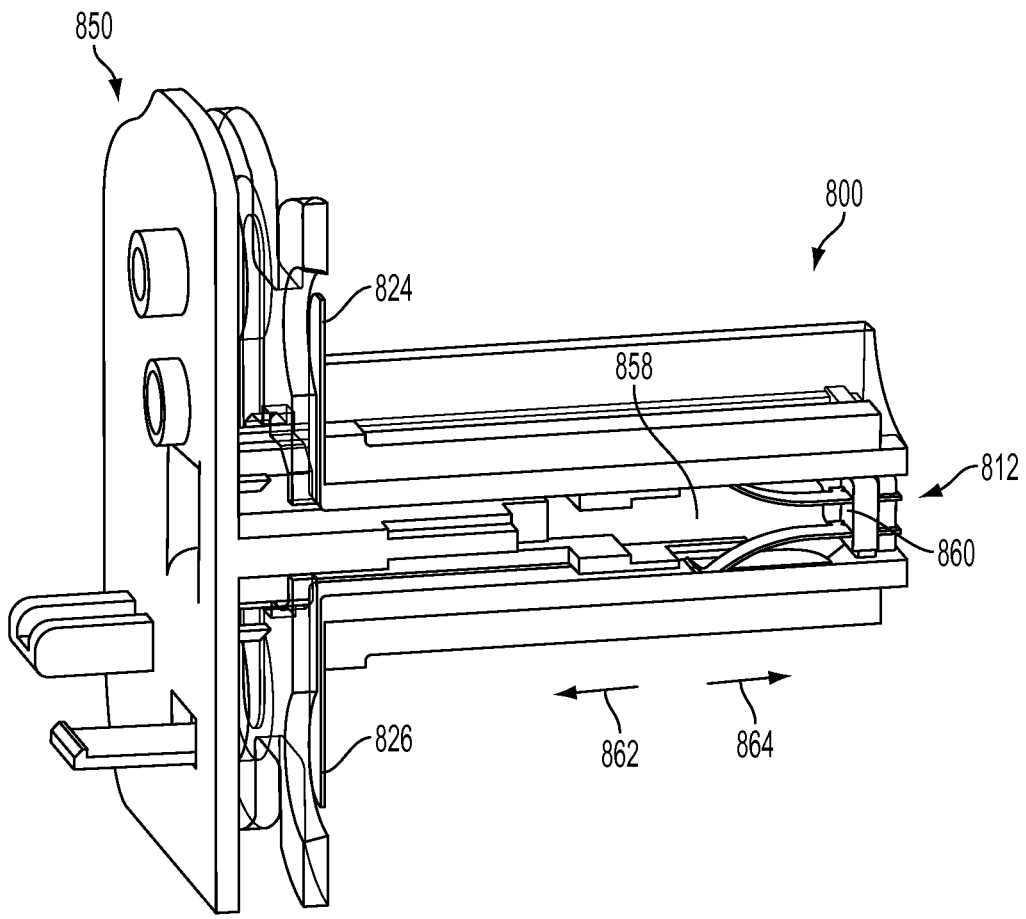

FIG. 56 illustrates a battery unit attached to a battery dock with various components omitted for clarity.

Figure 57A:
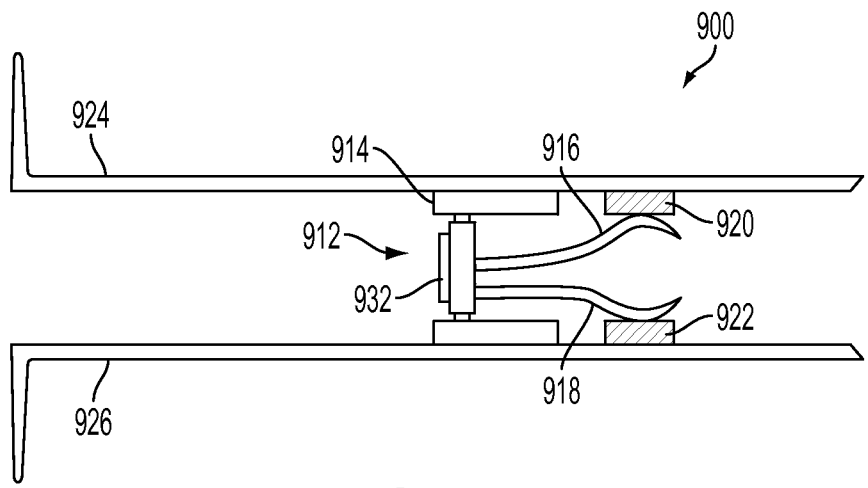
Figure 57B:
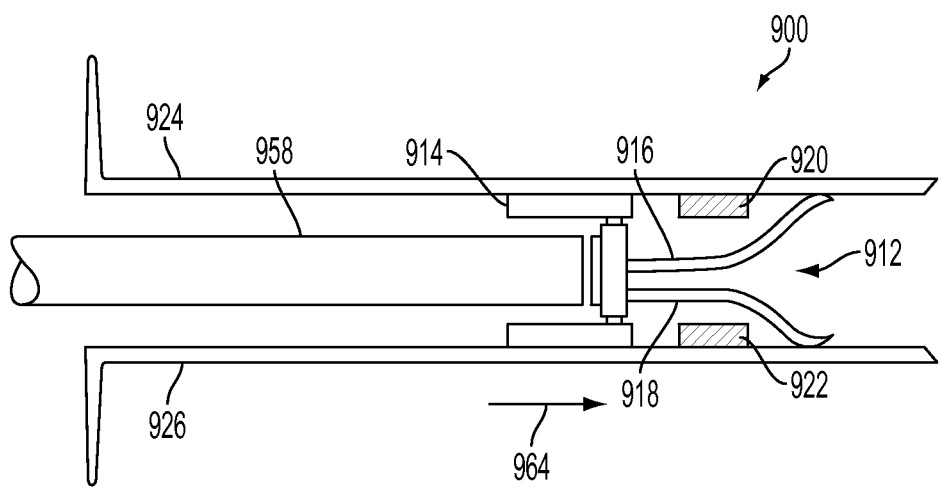

FIGS. 57A and 57B illustrate a battery unit with various components omitted for clarity.

Figure 58A:
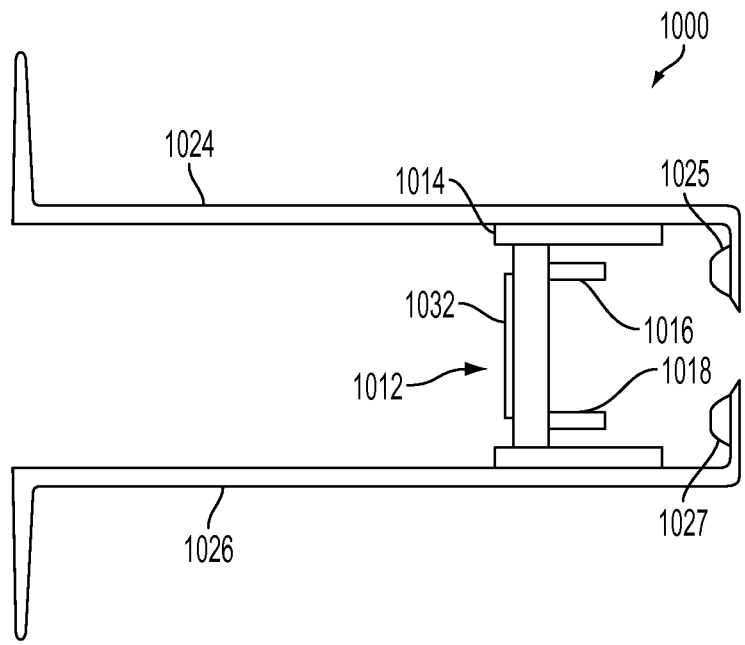
Figure 58B:
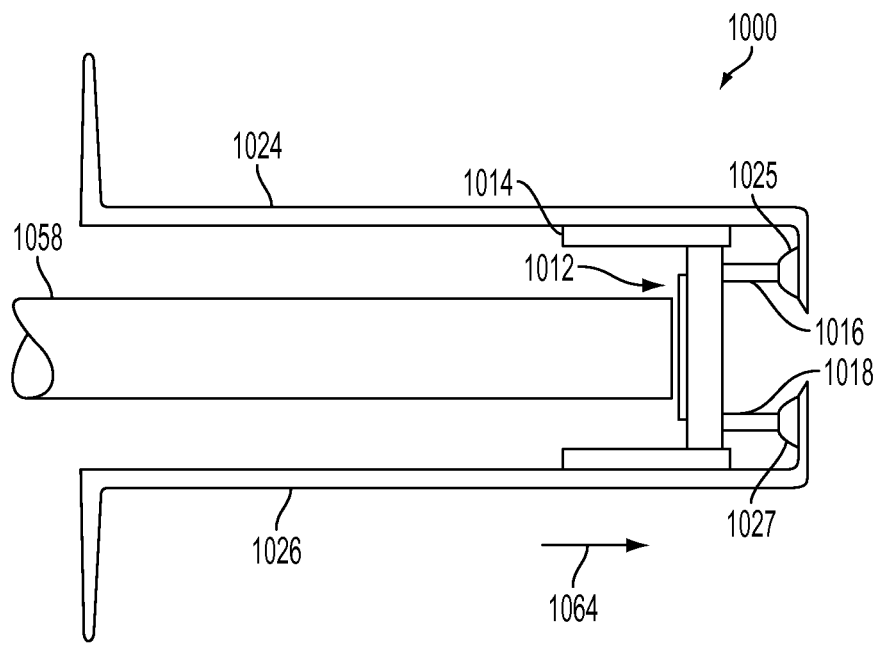

FIGS. 58A and 58B illustrate a battery unit with various components omitted for clarity.

Figure 59:
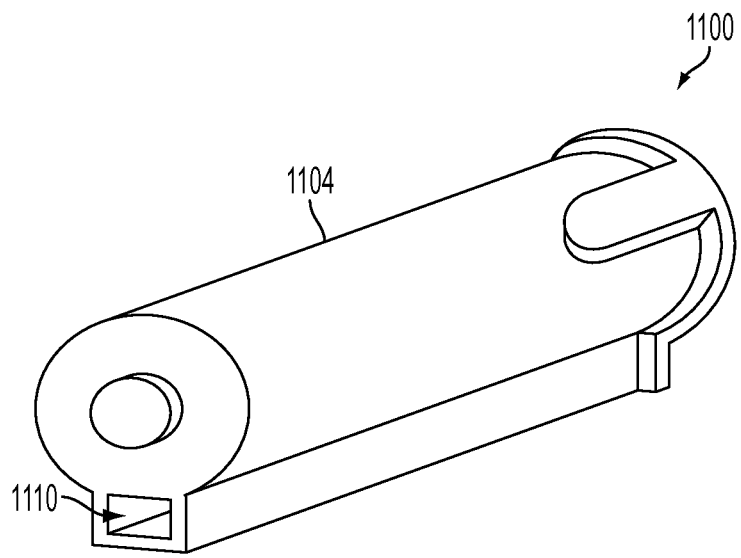

FIG. 59 is a perspective view of one embodiment of single cell battery unit.

Figure 60A:
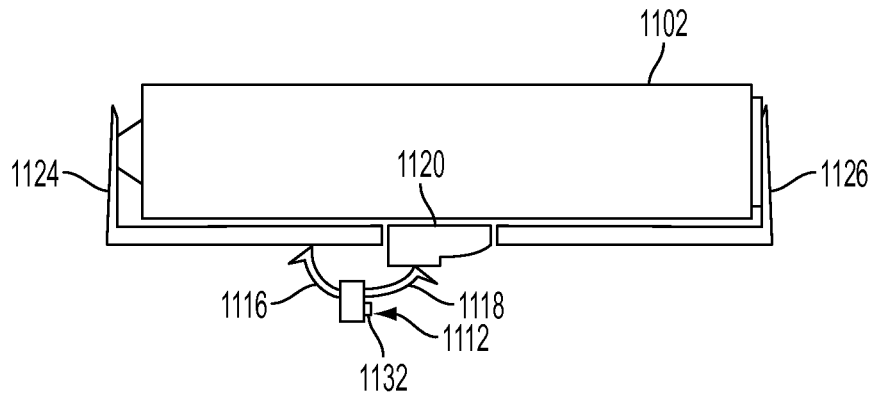
Figure 60B:
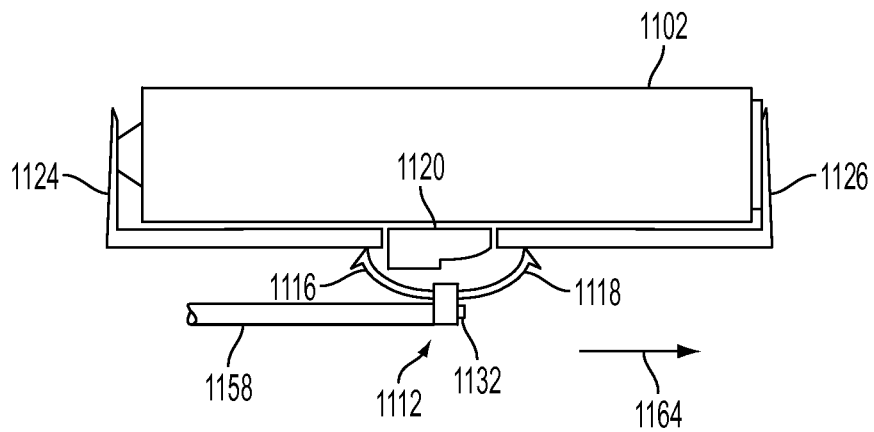

FIGS. 60A and 60B show internals views of the battery unit of FIG. 59 during various stages of operation with various components omitted for clarity.

DESCRIPTION

Various embodiments are directed to battery powered surgical instruments and batteries comprising features for facilitating shipping, storage and disposal. For example, according to one embodiment, a battery unit may comprise at least one cell within a casing that defines a cavity. The battery unit may have a translatable discharge drain positioned proximate to the cavity. The drain may be moveable between an open position and a closed position. A surgical instrument for use with the battery unit may comprise a battery dock, battery compartment, or other battery-receiving portion that includes a protruding portion that is received by the cavity of the battery unit. Prior to attachment to the surgical instrument, the discharge drain may be in the open position. Upon attachment of the battery unit to the surgical instrument, the protruding portion may contact the discharge drain to translate the drain with respect to the casing. When moved to its closed position, the discharge drain may create a discharge circuit between an anode of the battery unit, a cathode of the battery unit, and a resistive element, for example. From the time of attachment, the discharge circuit drains the energy from the battery unit. In some embodiments, the battery unit will be almost discharged or fully discharged or after about 24 hours, for example. Generally, the use of the discharge drain helps to ensure the voltage level of the battery unit are at or beneath acceptable levels for disposal.

Prior to describing embodiments of the cells, batteries, battery units, and associated surgical instruments, a detailed description of an example embodiments of a battery powered surgical instrument is provided. Although the surgical instruments described herein comprise motorized implements for cutting and stapling, it will be appreciated that the battery configurations described herein may be used with any suitable type of electrical surgical instrument such as cutters, claspers, staplers, RF cutter/coagulators, ultrasonic cutter/coagulators, and laser cutter/coagulators, for example.

Figure 1:
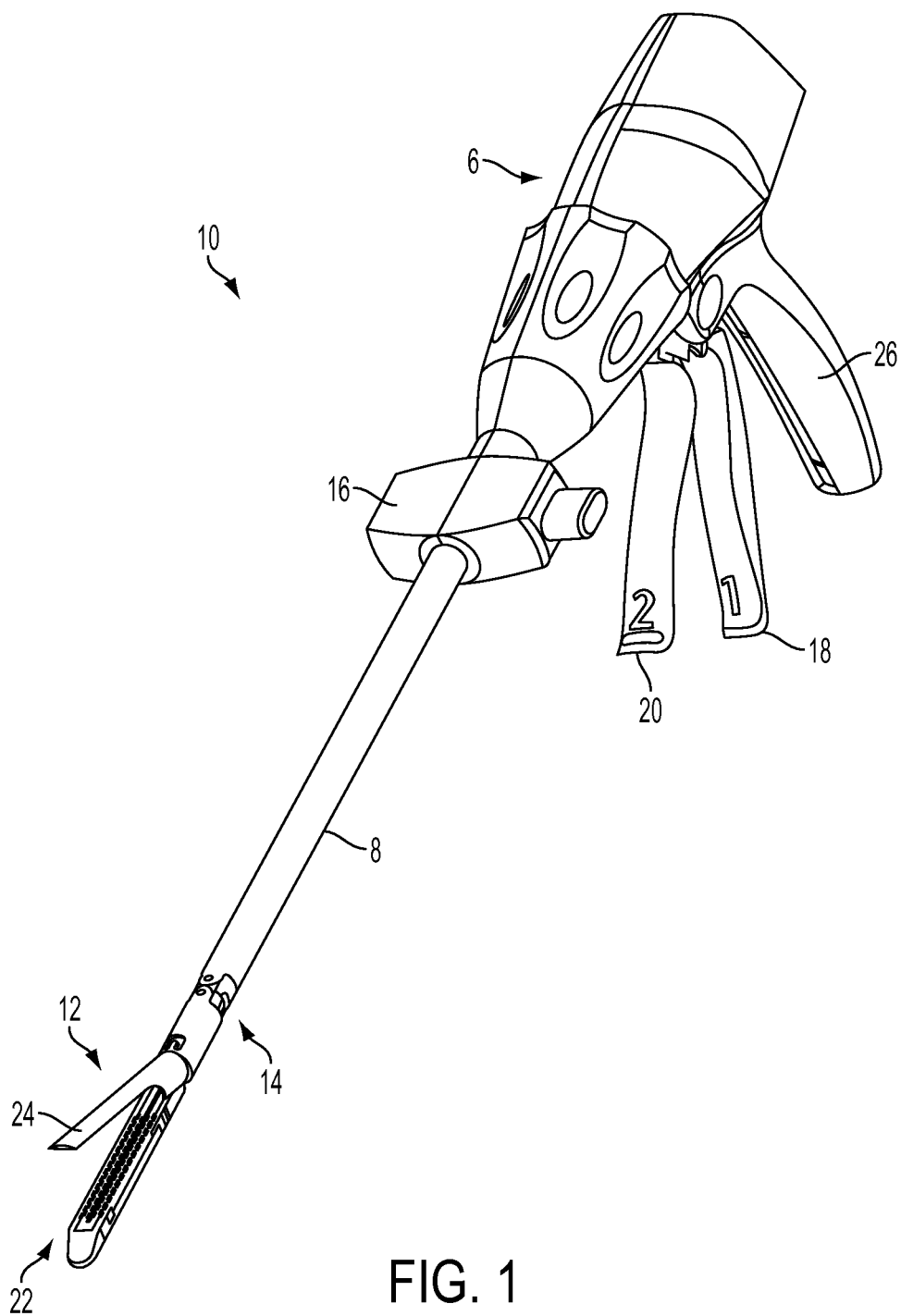
FIGS. 1 and 2 are perspective views of one embodiment of a surgical cutting and fastening instrument.
Figure 2:
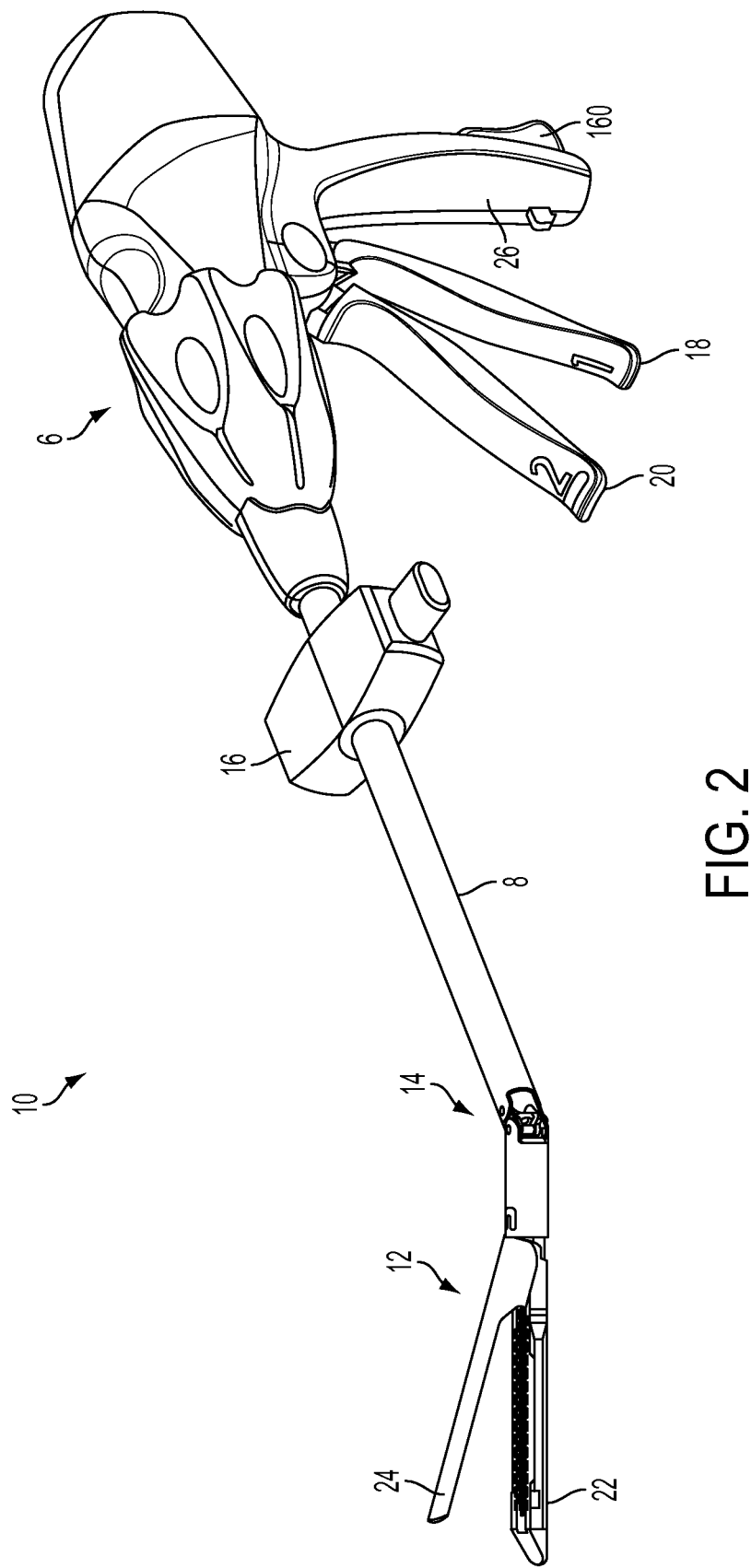

FIGS. 1 and 2 are perspective views of one embodiment of a surgical cutting and fastening instrument 10. The illustrated embodiment is an endoscopic instrument and, in general, the embodiments of the instrument 10 described herein are endoscopic surgical cutting and fastening instruments. It should be noted, however, that according to other embodiments, the instrument may be a non-endoscopic surgical cutting and fastening instrument, such as a laparoscopic or open surgical instrument.

The surgical instrument 10 depicted in FIGS. 1 and 2 comprises a handle 6, a shaft 8, and an articulating end effector 12 pivotally connected to the shaft 8 at an articulation pivot 14. An articulation control 16 may be provided adjacent to the handle 6 to effect rotation of the end effector 12 about the articulation pivot 14. In the illustrated embodiment, the end effector 12 is configured to act as an endocutter for clamping, severing and stapling tissue, although, in other embodiments, different types of end effectors may be used, such as end effectors for other types of surgical devices, such as graspers, cutters, staplers, clip appliers, access devices, drug/gene therapy devices, ultrasound, RF or laser devices, for example.

The handle 6 of the instrument 10 may include a closure trigger 18 and a firing trigger 20 for actuating the end effector 12. It will be appreciated that instruments having end effectors directed to different surgical tasks may have different numbers or types of triggers or other suitable controls for operating the end effector 12. The end effector 12 is shown separated from the handle 6 by a preferably elongate shaft 8. In one embodiment, a clinician or operator of the instrument 10 may articulate the end effector 12 relative to the shaft 8 by utilizing the articulation control 16, as described in more detail in pending U.S. patent application Ser. No. 11/329,020, filed Jan. 10, 2006, entitled "Surgical Instrument Having An Articulating End Effector," by Geoffrey C. Hueil et al., which is incorporated herein by reference in its entirety.

The end effector 12 includes in this example, among other things, a staple channel 22 and a pivotally translatable clamping member, such as an anvil 24, which are maintained at a spacing that assures effective stapling and severing of tissue clamped in the end effector 12. The handle 6 includes a pistol grip 26 towards which a closure trigger 18 is pivotally drawn by the clinician to cause clamping or closing of the anvil 24 toward the staple channel 22 of the end effector 12 to thereby clamp tissue positioned between the anvil 24 and channel 22. The firing trigger 20 is farther outboard of the closure trigger 18. Once the closure trigger 18 is locked in the closure position as further described below, the firing trigger 20 may rotate slightly toward the pistol grip 26 so that it can be reached by the operator using one hand. Then the operator may pivotally draw the firing trigger 20 toward the pistol grip 26 to cause the stapling and severing of clamped tissue in the end effector 12. In other embodiments, different types of clamping members besides the anvil 24 could be used, such as, for example, an opposing jaw.

It will be appreciated that the terms "proximal" and "distal" are used herein with reference to a clinician gripping the handle 6 of an instrument 10. Thus, the end effector 12 is distal with respect to the more proximal handle 6. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The closure trigger 18 may be actuated first. Once the clinician is satisfied with the positioning of the end effector 12, the clinician may draw back the closure trigger 18 to its fully closed, locked position proximate to the pistol grip 26. The firing trigger 20 may then be actuated. The firing trigger 20 returns to the open position (shown in FIGS. 1 and 2) when the clinician removes pressure, as described more fully below. A release button 160 on the handle 6, and in this example, on the pistol grip 26 of the handle 6, when depressed may release the locked closure trigger 18.

Figure 3:
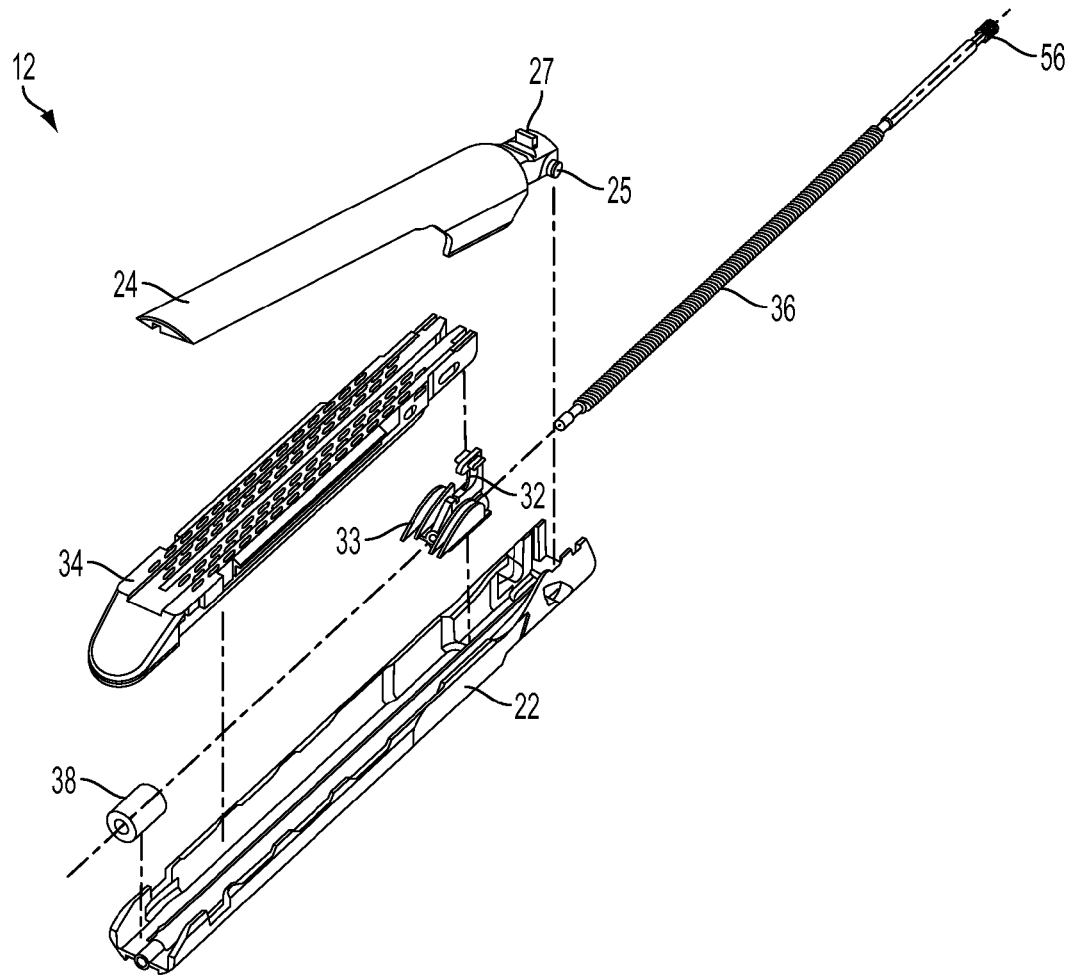
FIG. 3 is an exploded view of one embodiment of the end effector of the surgical cutting and fastening instrument of FIGS. 1 and 2.

FIG. 3 is an exploded view of one embodiment of the end effector 12. As shown in the illustrated embodiment, the end effector 12 may include, in addition to the previously-mentioned channel 22 and anvil 24, a cutting instrument 32, a sled 33, a staple cartridge 34 that is removably seated in the channel 22, and a helical screw shaft 36. The cutting instrument 32 may be, for example, a knife. The anvil 24 may be pivotably opened and closed at a pivot point 25 connected to the proximate end of the channel 22. The anvil 24 may also include a tab 27 at its proximate end that is inserted into a component of the mechanical closure system (described further below) to open and close the anvil 24. When the closure trigger 18 is actuated, that is, drawn in by a user of the instrument 10, the anvil 24 may pivot about the pivot point 25 into the clamped or closed position. If clamping of the end effector 12 is satisfactory, the operator may actuate the firing trigger 20, which, as explained in more detail below, causes the knife 32 and sled 33 to travel longitudinally along the channel 22, thereby cutting tissue clamped within the end effector 12. The movement of the sled 33 along the channel 22 causes the staples of the staple cartridge 34 to be driven through the severed tissue and against the closed anvil 24, which turns the staples to fasten the severed tissue. U.S. Pat. No. 6,978,921, entitled "Surgical Stapling Instrument Incorporating An E-Beam Firing Mechanism," which is incorporated herein by reference, provides more details about such two-stroke cutting and fastening instruments. According to various embodiments, the sled 33 may be an integral part of the cartridge 34, such that when the knife 32 retracts following the cutting operation, the sled 33 does not retract.

It should be noted that although the embodiments of the instrument 10 described herein employ an end effector 12 that staples the severed tissue, in other embodiments different techniques for fastening or sealing the severed tissue may be used. For example, end effectors that use RF energy or adhesives to fasten the severed tissue may also be used. U.S. Pat. No. 5,810,811, entitled "Electrosurgical Hemostatic Device," which is incorporated herein by reference, discloses a cutting instrument that uses RF energy to fasten the severed tissue. U.S. patent application Ser. No. 11/267,811, entitled "Surgical Stapling Instruments Structured For Delivery Of Medical Agents" and U.S. patent application Ser. No. 11/267,383, entitled "Surgical Stapling Instruments Structured For Pump-Assisted Delivery Of Medical Agents," both of which are also incorporated herein by reference, disclose cutting instruments that use adhesives to fasten the severed tissue. Accordingly, although the description herein refers to cutting/stapling operations and the like below, it should be recognized that this is an example embodiment and is not meant to be limiting. Other tissue-fastening techniques may also be used.

Figure 4:
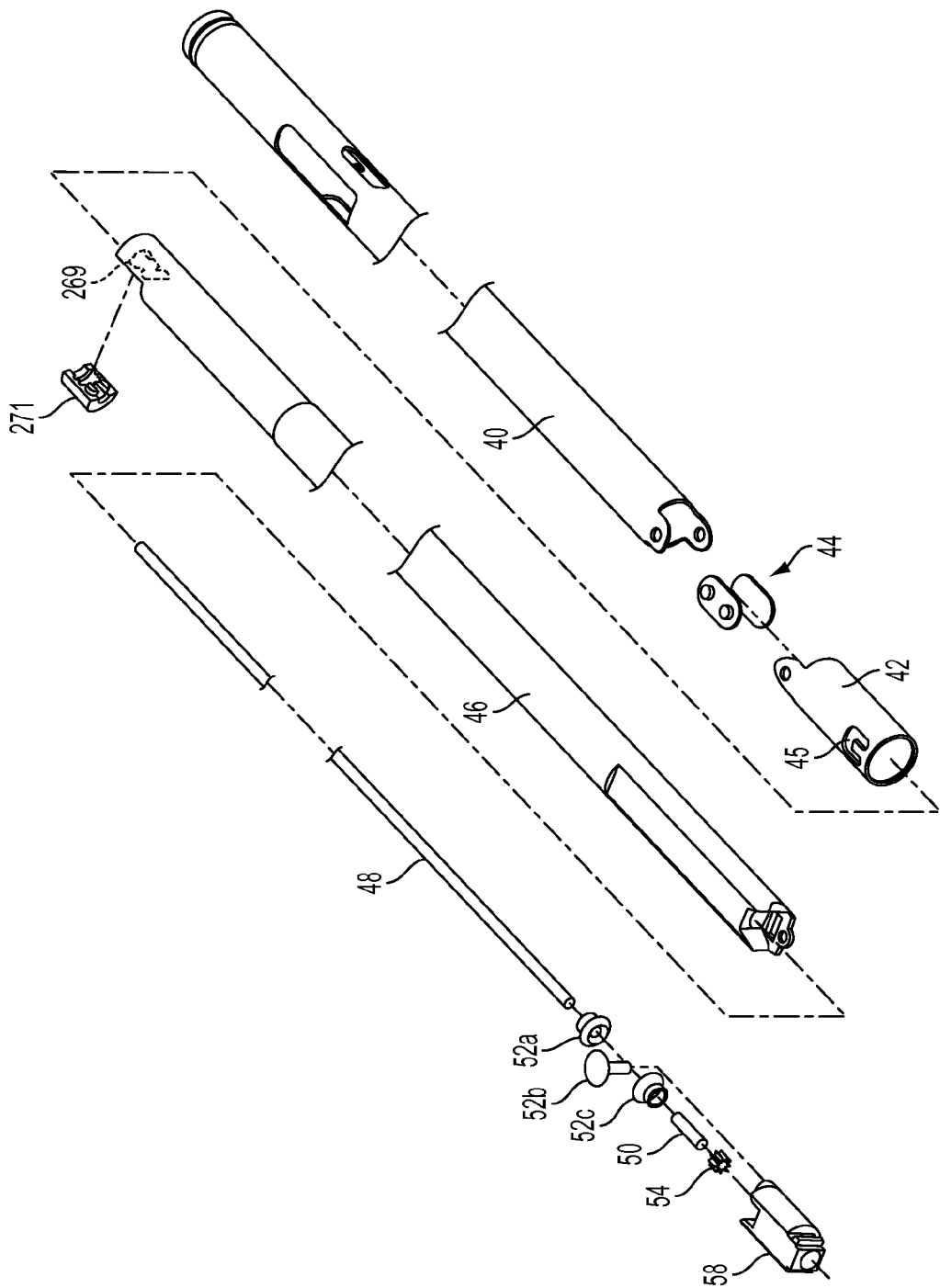
FIGS. 4 and 5 are exploded views of one embodiment of the end effector and shaft of the surgical cutting and fastening instrument of FIGS. 1 and 2.
Figure 5:
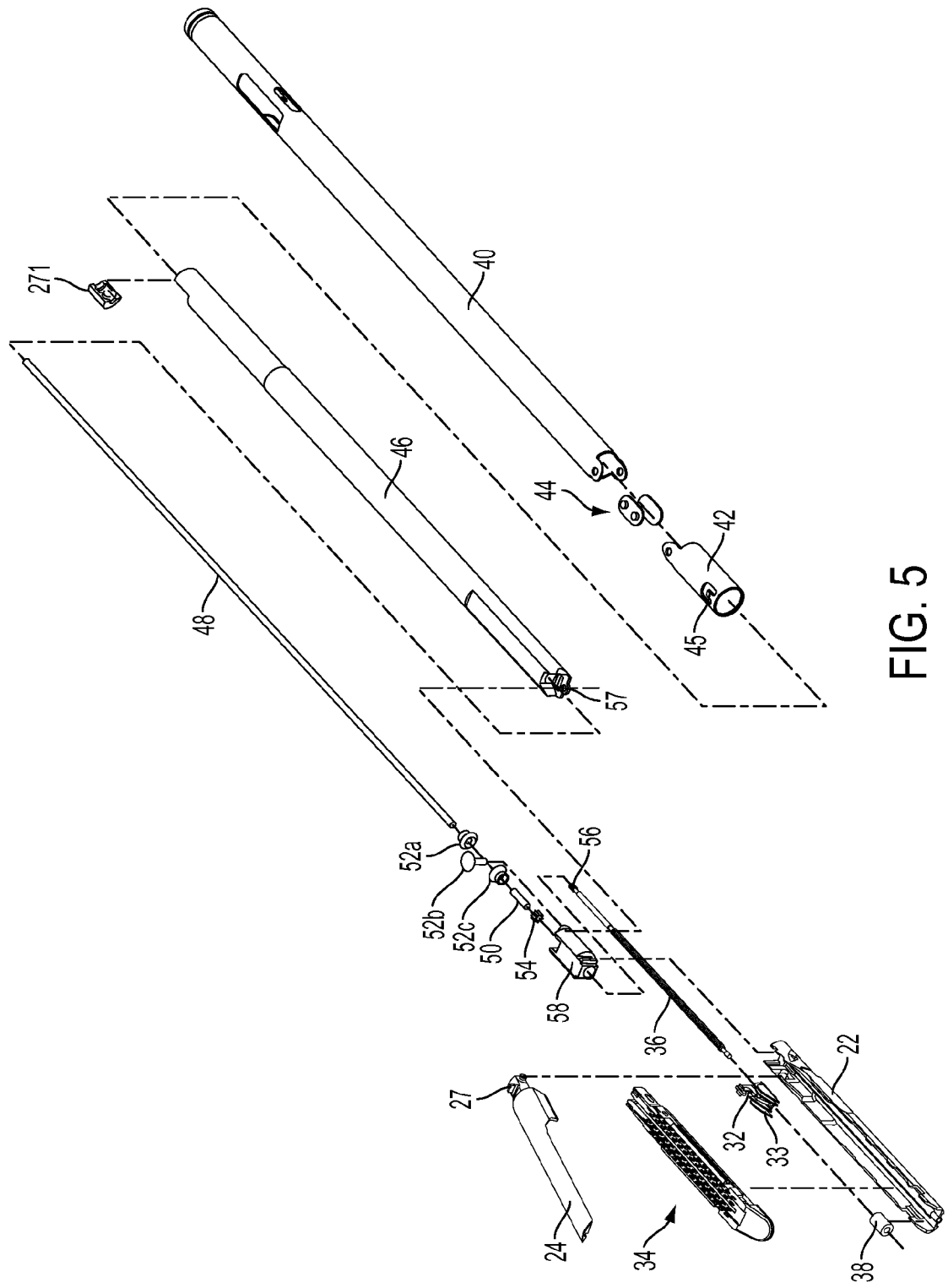
Figure 6:
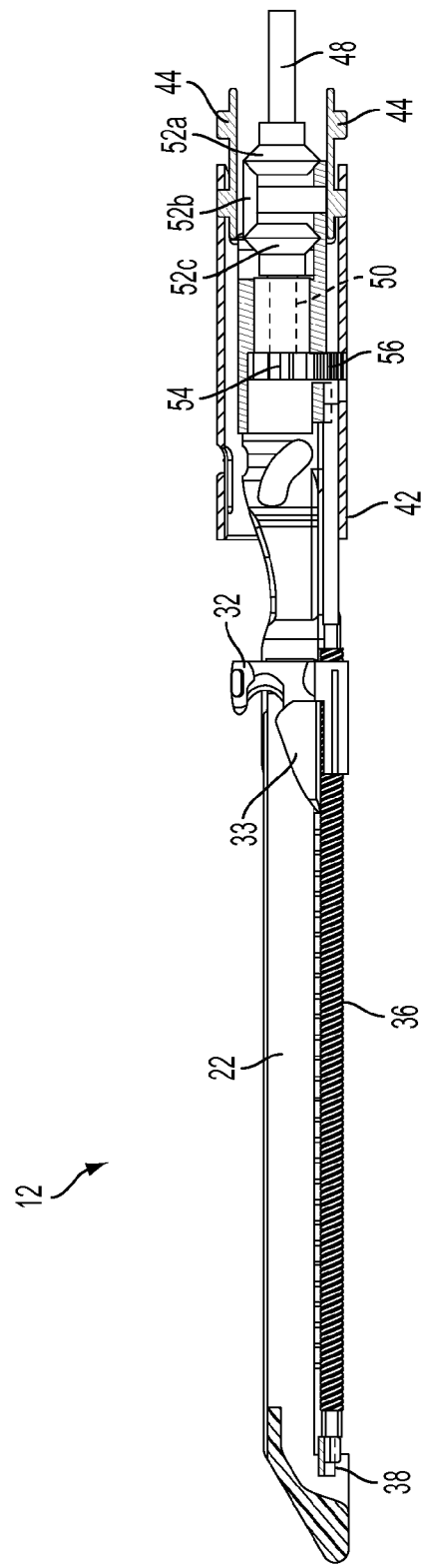
FIG. 6 is a side view of one embodiment the end effector of the surgical cutting and fastening instrument of FIGS. 1 and 2.
Figure 7:
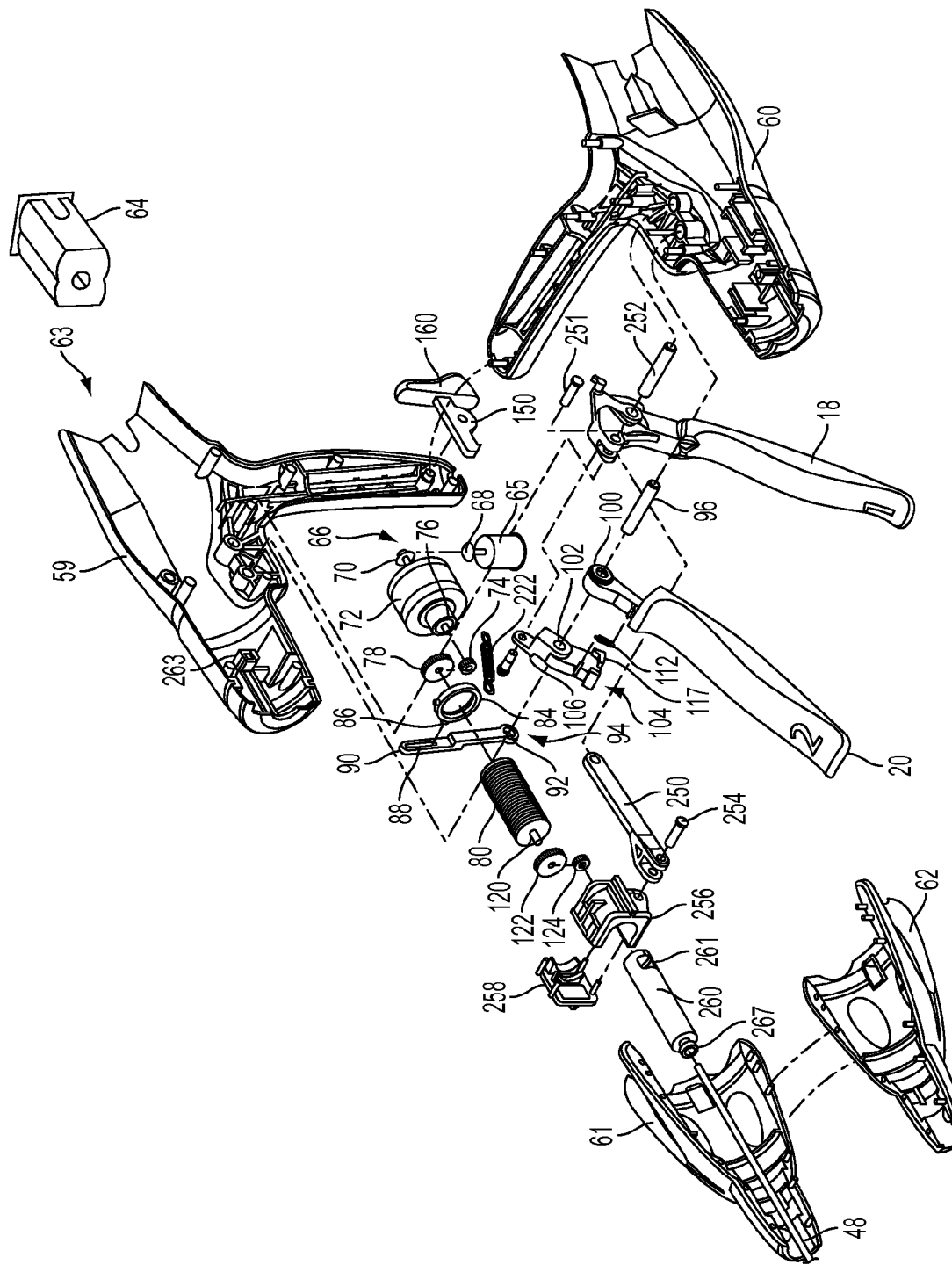
FIG. 7 is an exploded view of one embodiment of a motor-driven endocutter.

FIGS. 4 and 5 are exploded views and FIG. 6 is a side view of one embodiment of the end effector 12 and shaft 8. As shown in the illustrated embodiment, the shaft 8 may include a proximate closure tube 40 and a distal closure tube 42 pivotably linked by a pivot links 44. The distal closure tube 42 includes an opening 45 into which the tab 27 on the anvil 24 is inserted in order to open and close the anvil 24, as further described below. Disposed inside the closure tubes 40, 42 may be a proximate spine tube 46. Disposed inside the proximate spine tube 46 may be a main rotational (or proximate) drive shaft 48 that communicates with a secondary (or distal) drive shaft 50 via a bevel gear assembly 52. The secondary drive shaft 50 is connected to a drive gear 54 that engages a proximate drive gear 56 of the helical screw shaft 36. When the main drive shaft 48 is caused to rotate by actuation of the firing trigger 20 (as explained in more detail below), the bevel gear assembly 52a-c causes the secondary drive shaft 50 to rotate, which in turn, because of the engagement of the drive gears 54, 56, causes the helical screw shaft 36 to rotate, which causes the knife/sled driving member 32 to travel longitudinally along the channel 22 to cut any tissue clamped within the end effector 12. The vertical bevel gear 52b may sit and pivot in an opening 57 in the distal end of the proximate spine tube 46. A distal spine tube 58 may be used to enclose the secondary drive shaft 50 and the drive gears 54, 56. Collectively, the main drive shaft 48, the secondary drive shaft 50, and the articulation assembly (e.g., the bevel gear assembly 52a-c) are sometimes referred to herein as the "main drive shaft assembly."

A bearing 38 is threaded on the helical drive screw 36. The bearing 36 is also connected to the knife 32. When the helical drive screw 36 forward rotates, the bearing 38 traverses the helical drive screw 36 distally, driving the cutting instrument 32 and, in the process, the sled 33 to perform the cutting/stapling operation. The sled 33 may be made of, for example, plastic, and may have a sloped distal surface. As the sled 33 traverses the channel 22, the sloped forward surface may push up or drive the staples in the staple cartridge 34 through the clamped tissue and against the anvil 24. The anvil 24 turns the staples, thereby stapling the severed tissue. When the knife 32 is retracted, the knife 32 and sled 33 may become disengaged, thereby leaving the sled 33 at the distal end of the channel 22.

Because of the lack of user feedback for the cutting/stapling operation, there is a general lack of acceptance among physicians of motor-driven surgical instruments where the cutting/stapling operation is actuated by merely pressing a button. In contrast, various embodiments may provide a motor-driven endocutter with user-feedback of the deployment, force, and/or position of the cutting instrument in the end effector.

FIGS. 7-10 illustrate one embodiment of a motor-driven endocutter, and in particular the handle 6 thereof, that provides user-feedback regarding the deployment and loading force of the cutting instrument in the end effector. In addition, the embodiment may use power provided by the user in retracting the firing trigger 20 to power the device (a so-called "power assist" mode). As shown in the illustrated embodiment, the handle 6 includes exterior lower side pieces 59, 60 and exterior upper side pieces 61, 62 that fit together to form, in general, the exterior of the handle 6. A battery 64, such as a Li ion battery, may be provided in a battery dock 63. In some embodiments, the battery 64 is provided in the pistol grip portion 26 of the handle 6. Although the battery 64 is illustrated as containing multiple cells connected together, it is to be appreciated that the battery 64, in some embodiments, may include a single cell. The battery 64 may power a motor 65 disposed in an upper portion of the pistol grip portion 26 of the handle 6. According to various embodiments, the motor 65 may be a DC brushed driving motor having a maximum rotation of, approximately, 5000 RPM. The motor 65 may drive a 90° bevel gear assembly 66 comprising a first bevel gear 68 and a second bevel gear 70. The bevel gear assembly 66 may drive a planetary gear assembly 72. The planetary gear assembly 72 may include a pinion gear 74 connected to a drive shaft 76. The pinion gear 74 may drive a mating ring gear 78 that drives a helical gear drum 80 via a drive shaft 82. A ring 84 may be threaded on the helical gear drum 80. Thus, when the motor 65 rotates, the ring 84 is caused to travel along the helical gear drum 80 by means of the interposed bevel gear assembly 66, planetary gear assembly 72 and ring gear 78.

The handle 6 may also include a run motor sensor 110 in communication with the firing trigger 20 to detect when the firing trigger 20 has been drawn in (or "closed") toward the pistol grip portion 26 of the handle 6 by the operator to thereby actuate the cutting/stapling operation by the end effector 12. The sensor 110 may be a proportional sensor such as, for example, a rheostat or variable resistor. When the firing trigger 20 is drawn in, the sensor 110 detects the movement, and sends an electrical signal indicative of the voltage (or power) to be supplied to the motor 65. When the sensor 110 is a variable resistor or the like, the rotation of the motor 65 may be generally proportional to the amount of movement of the firing trigger 20. That is, if the operator only draws or closes the firing trigger 20 in a little bit, the rotation of the motor 65 is relatively low. When the firing trigger 20 is fully drawn in (or in the fully closed position), the rotation of the motor 65 is at its maximum. In other words, the harder the user pulls on the firing trigger 20, the more voltage is applied to the motor 65, causing greater rates of rotation.

The handle 6 may include a middle handle piece 104 adjacent to the upper portion of the firing trigger 20. The handle 6 also may comprise a bias spring 112 connected between posts on the middle handle piece 104 and the firing trigger 20. The bias spring 112 may bias the firing trigger 20 to its fully open position. In that way, when the operator releases the firing trigger 20, the bias spring 112 will pull the firing trigger 20 to its open position, thereby removing actuation of the sensor 110, thereby stopping rotation of the motor 65. Moreover, by virtue of the bias spring 112, any time a user closes the firing trigger 20, the user will experience resistance to the closing operation, thereby providing the user with feedback as to the amount of rotation exerted by the motor 65. Further, the operator could stop retracting the firing trigger 20 to thereby remove force from the sensor 100, to thereby stop the motor 65. As such, the user may stop the deployment of the end effector 12, thereby providing a measure of control of the cutting/fastening operation to the operator.

The distal end of the helical gear drum 80 includes a distal drive shaft 120 that drives a ring gear 122, which mates with a pinion gear 124. The pinion gear 124 is connected to the main drive shaft 48 of the main drive shaft assembly. In that way, rotation of the motor 65 causes the main drive shaft assembly to rotate, which causes actuation of the end effector 12, as described above.

The ring 84 threaded on the helical gear drum 80 may include a post 86 that is disposed within a slot 88 of a slotted arm 90. The slotted arm 90 has an opening 92 its opposite end 94 that receives a pivot pin 96 that is connected between the handle exterior side pieces 59, 60. The pivot pin 96 is also disposed through an opening 100 in the firing trigger 20 and an opening 102 in the middle handle piece 104.

In addition, the handle 6 may include a reverse motor (or end-of-stroke sensor) 130 and a stop motor (or beginning-of-stroke) sensor 142. In various embodiments, the reverse motor sensor 130 may be a limit switch located at the distal end of the helical gear drum 80 such that the ring 84 threaded on the helical gear drum 80 contacts and trips the reverse motor sensor 130 when the ring 84 reaches the distal end of the helical gear drum 80. The reverse motor sensor 130, when activated, sends a signal to the motor 65 to reverse its rotation direction, thereby withdrawing the knife 32 of the end effector 12 following the cutting operation.

The stop motor sensor 142 may be, for example, a normally-closed limit switch. In various embodiments, it may be located at the proximate end of the helical gear drum 80 so that the ring 84 trips the switch 142 when the ring 84 reaches the proximate end of the helical gear drum 80.

In operation, when an operator of the instrument 10 pulls back the firing trigger 20, the sensor 110 detects the deployment of the firing trigger 20 and sends a signal to the motor 65 to cause forward rotation of the motor 65 at, for example, a rate proportional to how hard the operator pulls back the firing trigger 20. The forward rotation of the motor 65 in turn causes the ring gear 78 at the distal end of the planetary gear assembly 72 to rotate, thereby causing the helical gear drum 80 to rotate, causing the ring 84 threaded on the helical gear drum 80 to travel distally along the helical gear drum 80. The rotation of the helical gear drum 80 also drives the main drive shaft assembly as described above, which in turn causes deployment of the knife 32 in the end effector 12. That is, the knife 32 and sled 33 are caused to traverse the channel 22 longitudinally, thereby cutting tissue clamped in the end effector 12. Also, the stapling operation of the end effector 12 is caused to happen in embodiments where a stapling-type end effector is used.

By the time the cutting/stapling operation of the end effector 12 is complete, the ring 84 on the helical gear drum 80 will have reached the distal end of the helical gear drum 80, thereby causing the reverse motor sensor 130 to be tripped, which sends a signal to the motor 65 to cause the motor 65 to reverse its rotation. This in turn causes the knife 32 to retract, and also causes the ring 84 on the helical gear drum 80 to move back to the proximate end of the helical gear drum 80.

Figure 8:
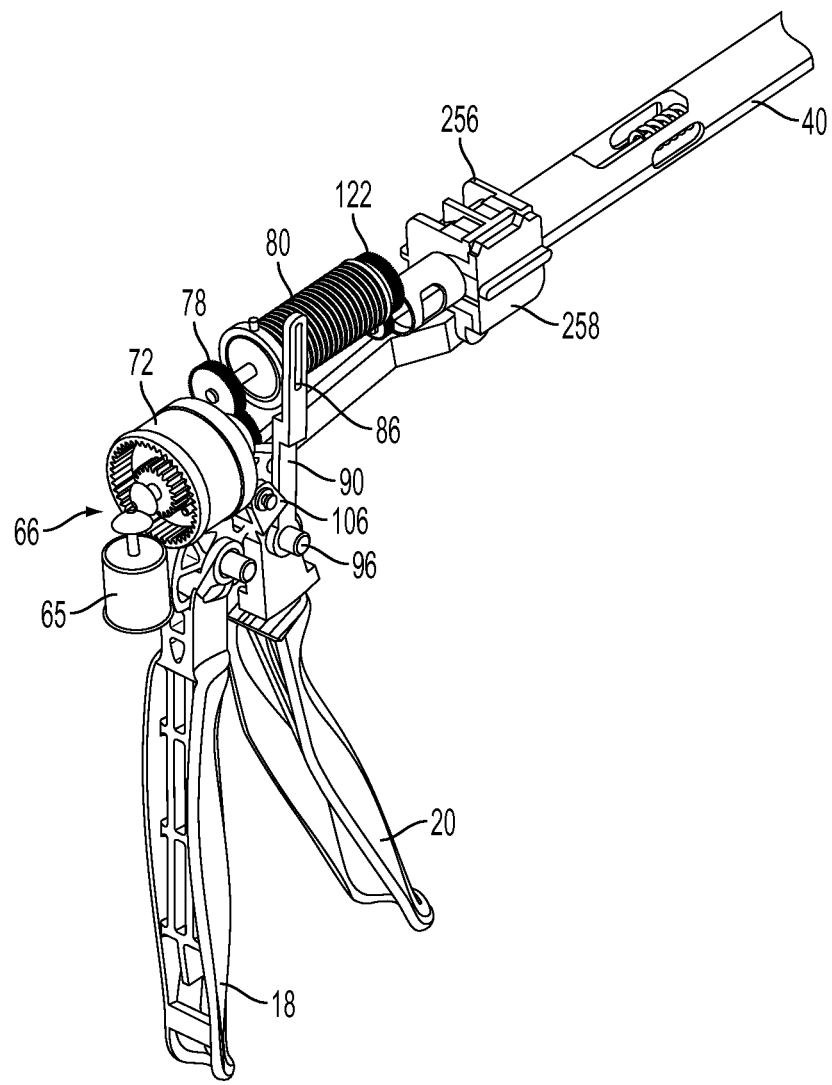
FIGS. 8 and 9 are partial perspective views of one embodiment of the handle of the endocutter of FIG. 7.
Figure 9:
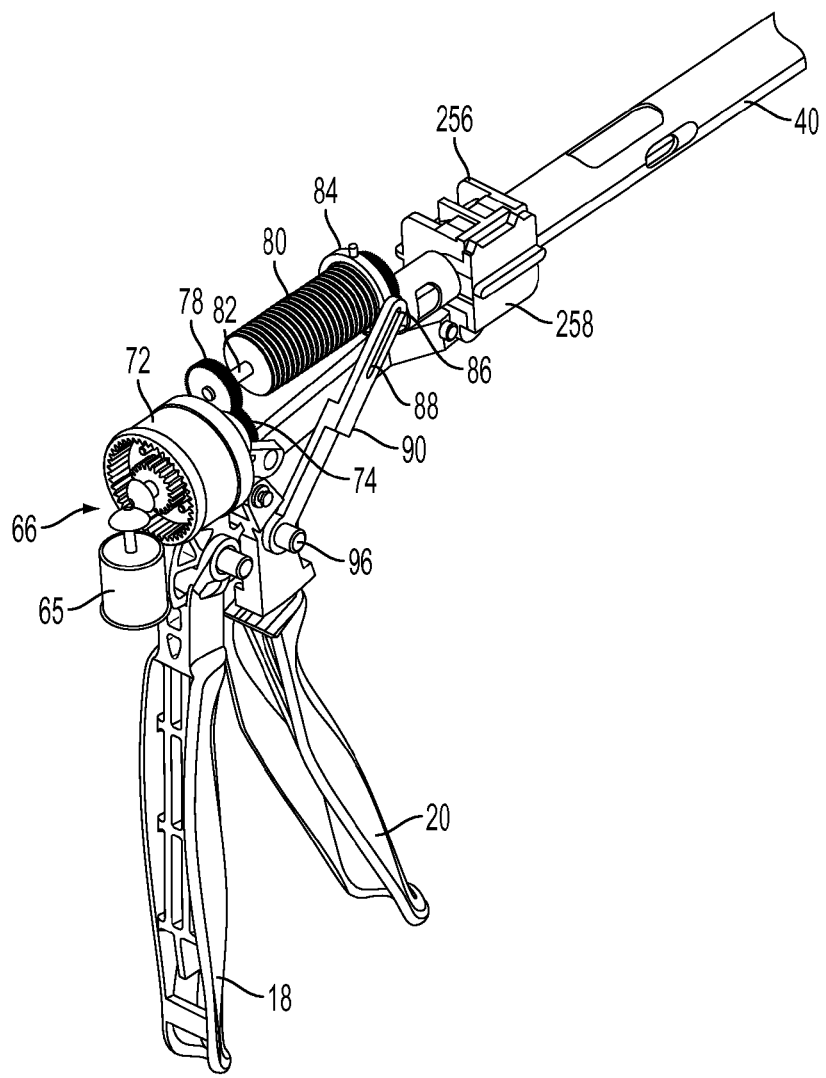
Figure 10:
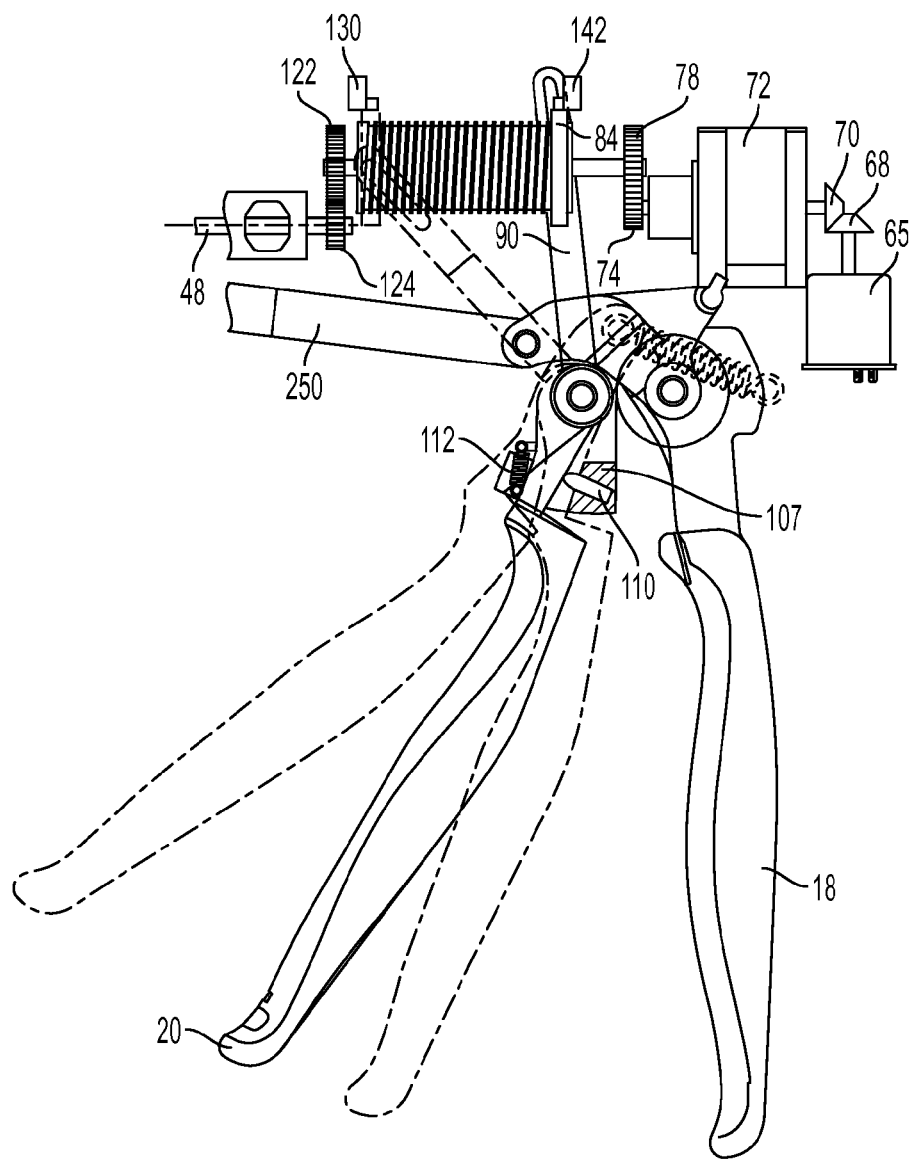
FIG. 10 is a side view of one embodiment of the handle of the endocutter of FIG. 7.

The middle handle piece 104 includes a backside shoulder 106 that engages the slotted arm 90 as best shown in FIGS. 8 and 9. The middle handle piece 104 also has a forward motion stop 107 that engages the firing trigger 20. The movement of the slotted arm 90 is controlled, as explained above, by rotation of the motor 65. When the slotted arm 90 rotates CCW as the ring 84 travels from the proximate end of the helical gear drum 80 to the distal end, the middle handle piece 104 will be free to rotate CCW. Thus, as the user draws in the firing trigger 20, the firing trigger 20 will engage the forward motion stop 107 of the middle handle piece 104, causing the middle handle piece 104 to rotate CCW. Due to the backside shoulder 106 engaging the slotted arm 90, however, the middle handle piece 104 will only be able to rotate CCW as far as the slotted arm 90 permits. In that way, if the motor 65 should stop rotating for some reason, the slotted arm 90 will stop rotating, and the user will not be able to further draw in the firing trigger 20 because the middle handle piece 104 will not be free to rotate CCW due to the slotted arm 90.

FIGS. 41 and 42 illustrate two states of one embodiment of a variable sensor that may be used as the run motor sensor 110. The sensor 110 may include a face portion 280, a first electrode (A) 282, a second electrode (B) 284, and a compressible dielectric material 286 (e.g., EAP) between the electrodes 282, 284. The sensor 110 may be positioned such that the face portion 280 contacts the firing trigger 20 when retracted. Accordingly, when the firing trigger 20 is retracted, the dielectric material 286 is compressed, as shown in FIG. 42, such that the electrodes 282, 284 are closer together. Since the distance "b" between the electrodes 282, 284 is directly related to the impedance between the electrodes 282, 284, the greater the distance the more impedance, and the closer the distance the less impedance. In that way, the amount that the dielectric material 286 is compressed due to retraction of the firing trigger 20 (denoted as force "F" in FIG. 42) is proportional to the impedance between the electrodes 282, 284, which can be used to proportionally control the motor 65.

Components of an example closure system for closing (or clamping) the anvil 24 of the end effector 12 by retracting the closure trigger 18 are also shown in FIGS. 7-10. In the illustrated embodiment, the closure system includes a yoke 250 connected to the closure trigger 18 by a pin 251 that is inserted through aligned openings in both the closure trigger 18 and the yoke 250. A pivot pin 252, about which the closure trigger 18 pivots, is inserted through another opening in the closure trigger 18 which is offset from where the pin 251 is inserted through the closure trigger 18. Thus, retraction of the closure trigger 18 causes the upper part of the closure trigger 18, to which the yoke 250 is attached via the pin 251, to rotate CCW. The distal end of the yoke 250 is connected, via a pin 254, to a first closure bracket 256. The first closure bracket 256 connects to a second closure bracket 258. Collectively, the closure brackets 256, 258 define an opening in which the proximate end of the proximate closure tube 40 (see FIG. 4) is seated and held such that longitudinal movement of the closure brackets 256, 258 causes longitudinal motion by the proximate closure tube 40. The instrument 10 also includes a closure rod 260 disposed inside the proximate closure tube 40. The closure rod 260 may include a window 261 into which a post 263 on one of the handle exterior pieces, such as exterior lower side piece 59 in the illustrated embodiment, is disposed to fixedly connect the closure rod 260 to the handle 6. In that way, the proximate closure tube 40 is capable of moving longitudinally relative to the closure rod 260. The closure rod 260 may also include a distal collar 267 that fits into a cavity 269 in proximate spine tube 46 and is retained therein by a cap 271 (see FIG. 4).

In operation, when the yoke 250 rotates due to retraction of the closure trigger 18, the closure brackets 256, 258 cause the proximate closure tube 40 to move distally (e.g., away from the handle end of the instrument 10), which causes the distal closure tube 42 to move distally, which causes the anvil 24 to rotate about the pivot point 25 into the clamped or closed position. When the closure trigger 18 is unlocked from the locked position, the proximate closure tube 40 is caused to slide proximally, which causes the distal closure tube 42 to slide proximally, which by virtue of the tab 27 being inserted in the window 45 of the distal closure tube 42, causes the anvil 24 to pivot about the pivot point 25 into the open or unclamped position. In that way, by retracting and locking the closure trigger 18, an operator may clamp tissue between the anvil 24 and channel 22, and may unclamp the tissue following the cutting/stapling operation by unlocking the closure trigger 18 from the locked position.

Figure 11:
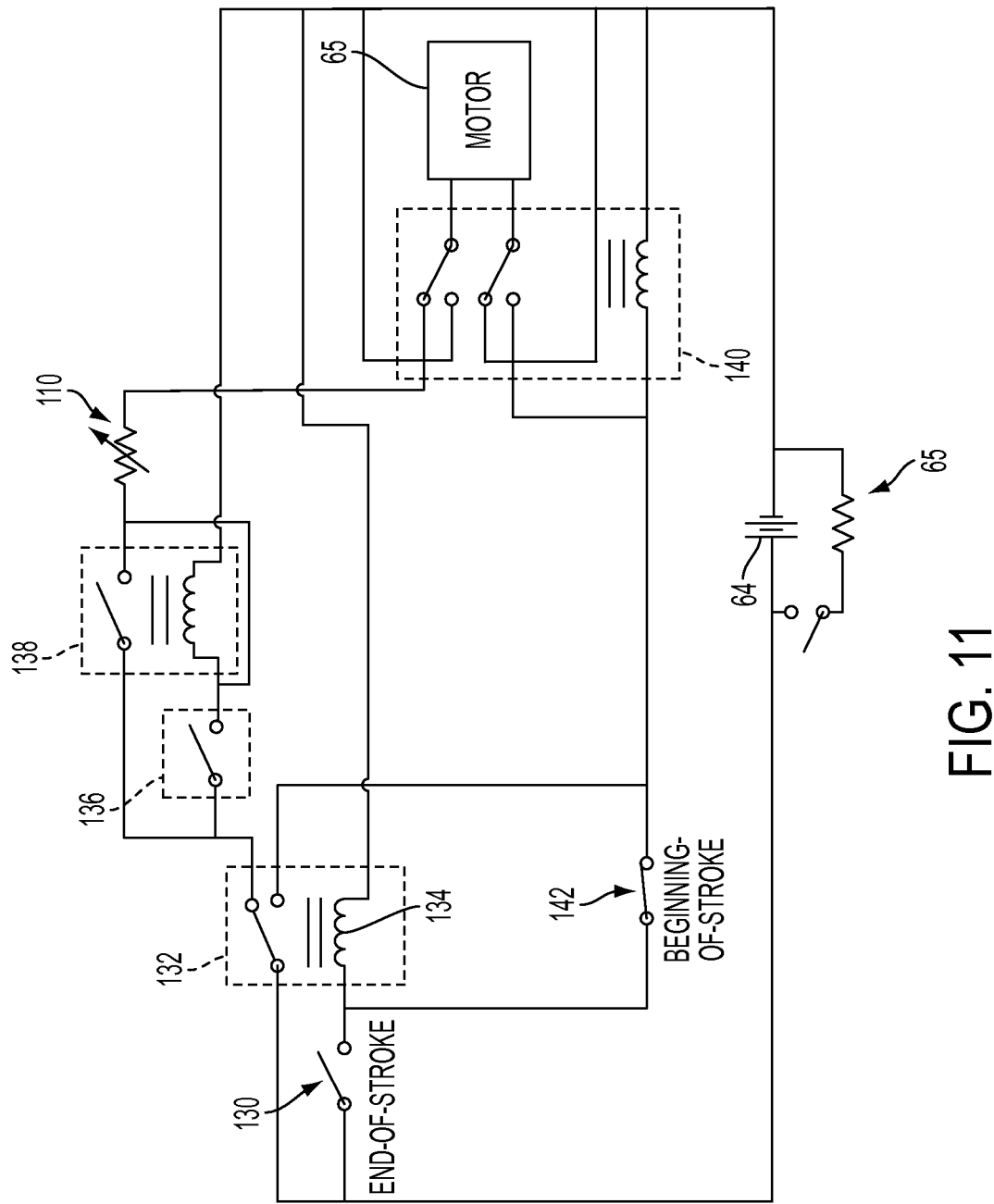
FIG. 11 is a schematic diagram of one embodiment of an electrical circuit of a surgical cutting and fastening instrument.

FIG. 11 is a schematic diagram of one embodiment of an electrical circuit of the instrument 10. When an operator initially pulls in the firing trigger 20 after locking the closure trigger 18, the sensor 110 is activated, allowing current to flow therethrough. If the normally-open reverse motor sensor switch 130 is open (meaning the end of the end effector stroke has not been reached), current will flow to a single pole, double throw relay 132. Since the reverse motor sensor switch 130 is not closed, the coil 134 of the relay 132 will not be energized, so the relay 132 will be in its non-energized state. The circuit also includes a cartridge lockout sensor switch 136. If the end effector 12 includes a staple cartridge 34, the sensor switch 136 will be in the closed state, allowing current to flow. Otherwise, if the end effector 12 does not include a staple cartridge 34, the sensor switch 136 will be open, thereby preventing the battery 64 from powering the motor 65. As discussed in the more detail below, when the battery 64 is inserted into the instrument 10, a resistive element 65 may be connected into the electrical circuit to discharge the battery 64.

When the staple cartridge 34 is present, the sensor switch 136 is closed, which energizes a single pole, single throw relay 138. When the relay 138 is energized, current flows through the relay 138, through the variable resistor sensor 110, and to the motor 65 via a double pole, double throw relay 140, thereby powering the motor 65 and allowing it to rotate in the forward direction.

When the end effector 12 reaches the end of its stroke, the reverse motor sensor 130 will be activated, thereby closing the switch 130 and energizing the relay 132. This causes the relay 132 to assume its energized state (not shown in FIG. 11), which causes current to bypass the cartridge lockout sensor switch 136 and variable resistor 110, and instead causes current to flow to both the normally-closed double pole, double throw relay 140 and back to the motor 65, but in a manner, via the relay 140, that causes the motor 65 to reverse its rotational direction.

Because the stop motor sensor switch 142 is normally-closed, current will flow back to the relay 132 to keep it energized until the switch 142 opens. When the knife 32 is fully retracted, the stop motor sensor switch 142 is activated, causing the switch 142 to open, thereby removing power from the motor 65.

In other embodiments, rather than a proportional-type sensor 110, an on-off type sensor could be used. In such embodiments, the rate of rotation of the motor 65 would not be proportional to the force applied by the operator. Rather, the motor 65 would generally rotate at a constant rate. But the operator would still experience force feedback because the firing trigger 20 is geared into the gear drive train.

Figure 12:
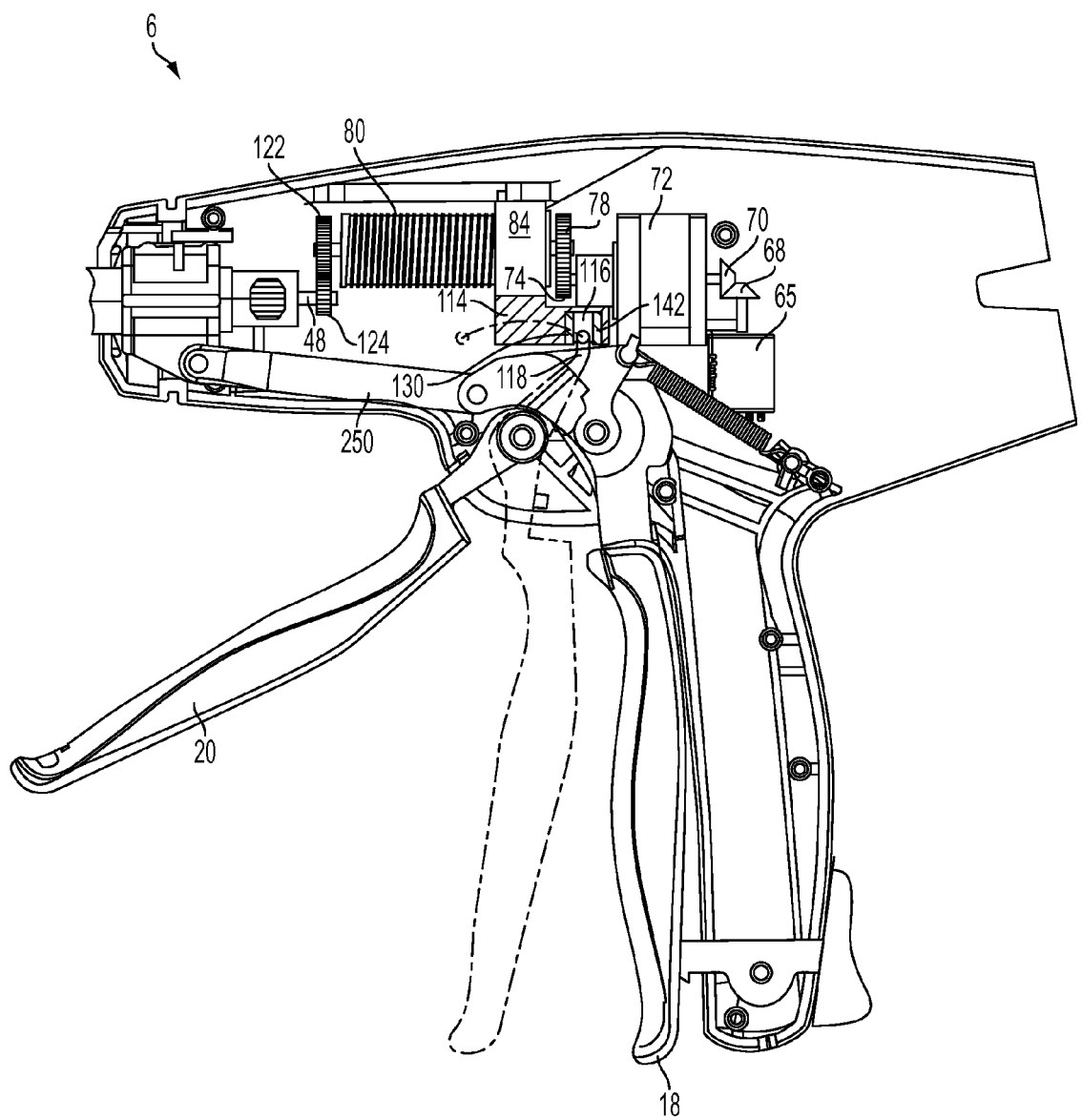
FIG. 12 is a side-view of a handle of one embodiment of a power-assist motorized endocutter.

FIG. 12 is a side-view of the handle 6 of a power-assist motorized endocutter according to another embodiment. The embodiment of FIG. 12 is similar to that of FIGS. 7-10 except that in the embodiment of FIG. 12, there is no slotted arm 90 connected to the ring 84 threaded on the helical gear drum 80. Instead, in the embodiment of FIG. 12, the ring 84 includes a sensor portion 114 that moves with the ring 84 as the ring 84 advances down (and back) on the helical gear drum 80. The sensor portion 114 includes a notch 116. The reverse motor sensor 130 may be located at the distal end of the notch 116 and the stop motor sensor 142 may be located at the proximate end of the notch 116. As the ring 84 moves down the helical gear drum 80 (and back), the sensor portion 114 moves with it. Further, as shown in FIG. 12, the middle piece 104 may have an arm 118 that extends into the notch 116.

In operation, as an operator of the instrument 10 retracts in the firing trigger 20 toward the pistol grip 26, the run motor sensor 110 detects the motion and sends a signal to power the motor 65, which causes, among other things, the helical gear drum 80 to rotate. As the helical gear drum 80 rotates, the ring 84 threaded on the helical gear drum 80 advances (or retracts, depending on the rotation). Also, due to the pulling in of the firing trigger 20, the middle piece 104 is caused to rotate CCW with the firing trigger 20 due to the forward motion stop 107 that engages the firing trigger 20. The CCW rotation of the middle piece 104 cause the arm 118 to rotate CCW with the sensor portion 114 of the ring 84 such that the arm 118 stays disposed in the notch 116. When the ring 84 reaches the distal end of the helical gear drum 80, the arm 118 will contact and thereby trip the reverse motor sensor 130. Similarly, when the ring 84 reaches the proximate end of the helical gear drum 80, the arm 118 will contact and thereby trip the stop motor sensor 142. Such actions may reverse and stop the motor 65, respectively, as described above.

Figure 13:
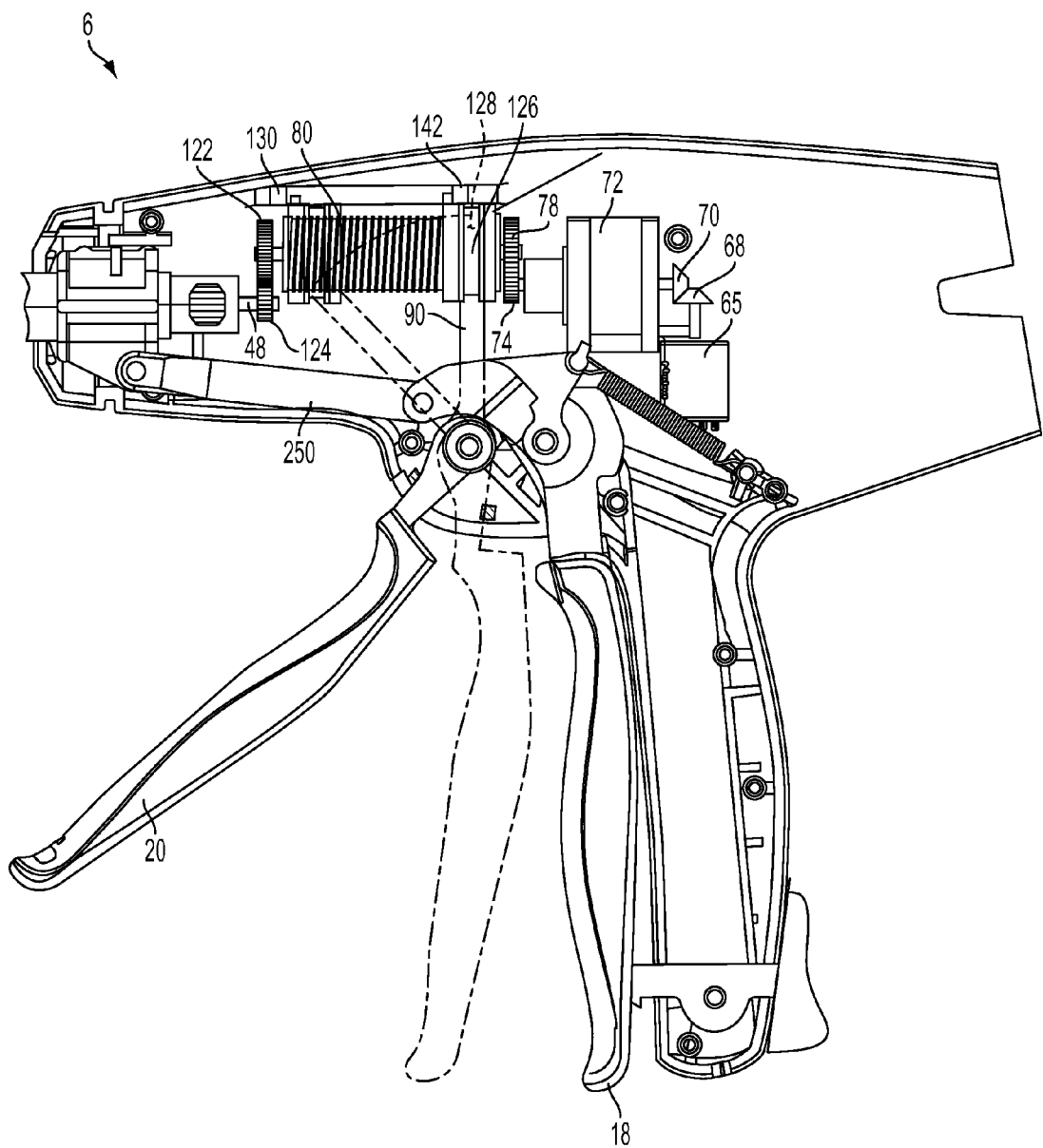
FIG. 13 is a side-view of a handle of another embodiment of a power-assist motorized endocutter.

FIG. 13 is a side-view of the handle 6 of a power-assist motorized endocutter according to another embodiment. The embodiment of FIG. 13 is similar to that of FIGS. 7-10 except that in the embodiment of FIG. 13, there is no slot in the arm 90. Instead, the ring 84 threaded on the helical gear drum 80 includes a vertical channel 126. Instead of a slot, the arm 90 includes a post 128 that is disposed in the channel 126. As the helical gear drum 80 rotates, the ring 84 threaded on the helical gear drum 80 advances (or retracts, depending on the rotation). The arm 90 rotates CCW as the ring 84 advances due to the post 128 being disposed in the channel 126, as shown in FIG. 13.

Figure 14:
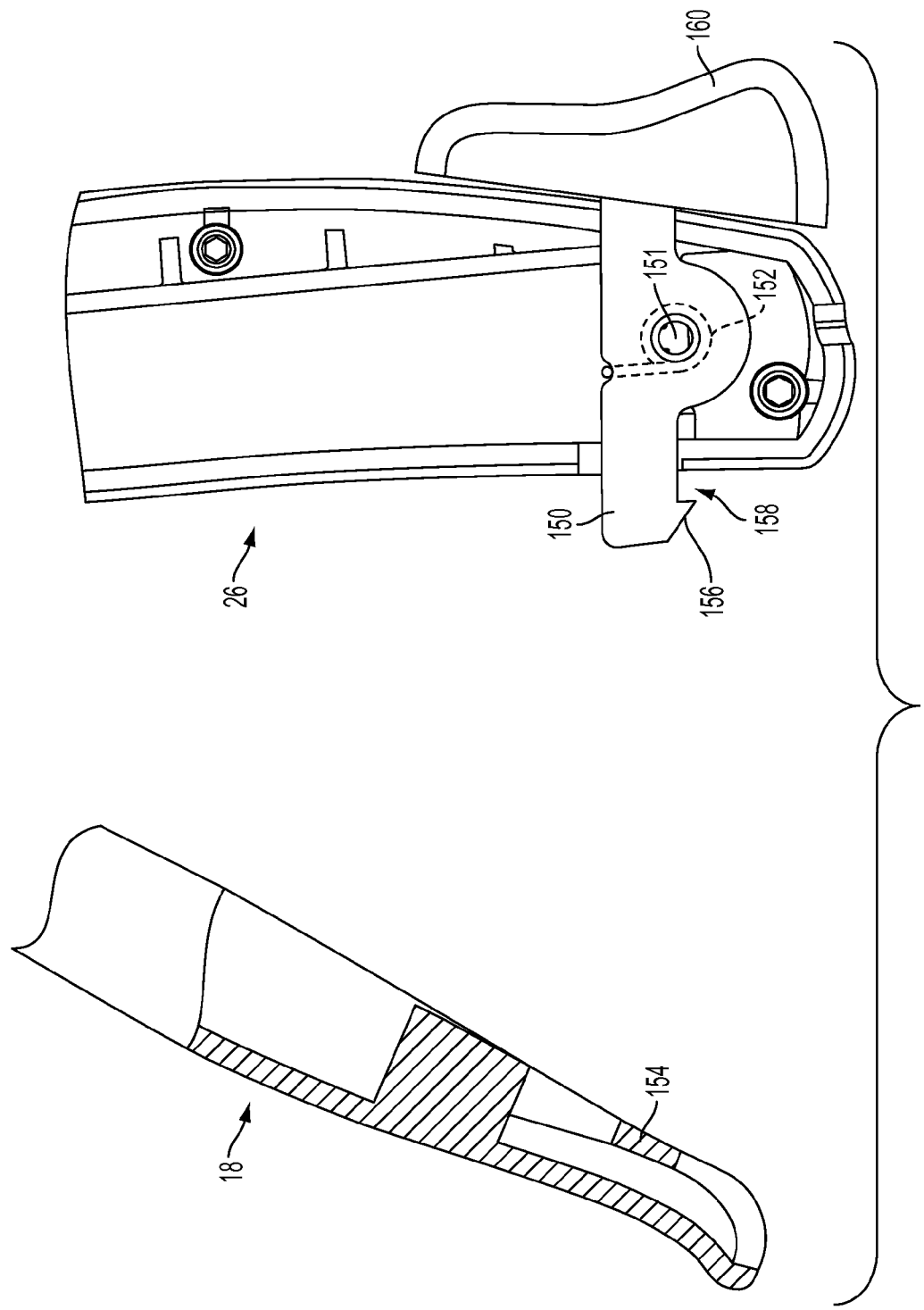
FIGS. 14 and 15 show one embodiment of a closure trigger locking mechanism.
Figure 15:
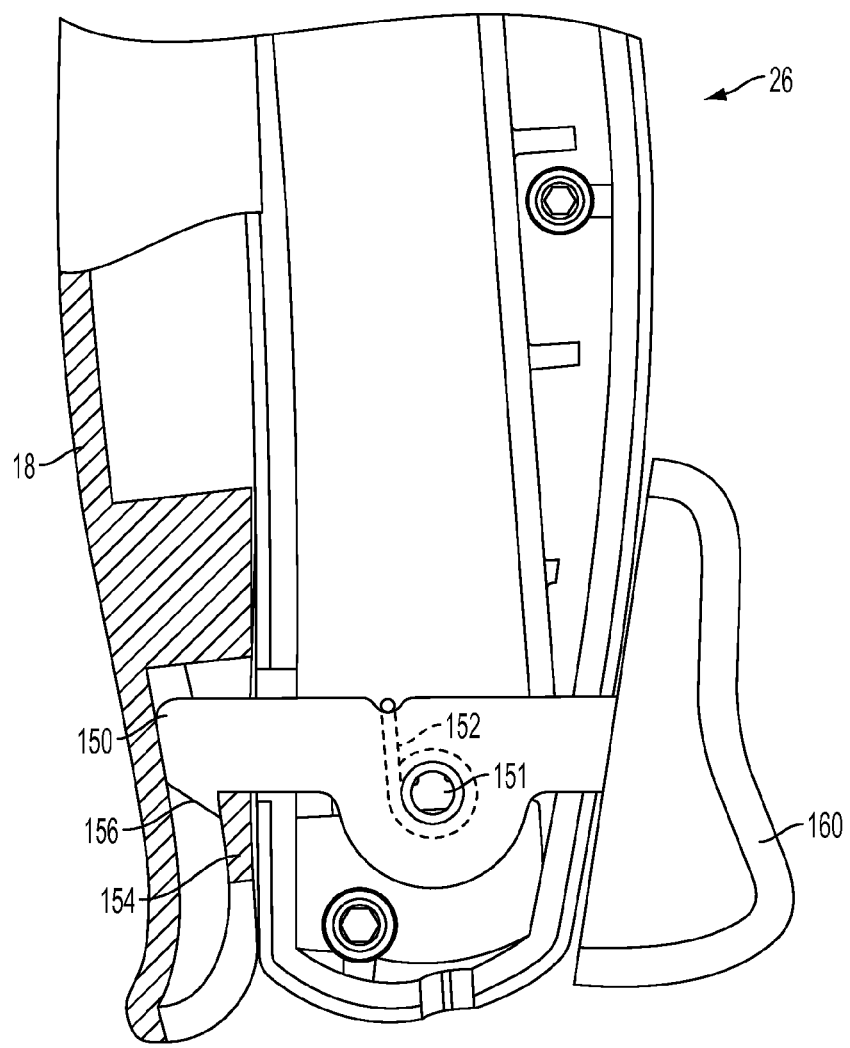

As mentioned above, in using a two-stroke motorized instrument, the operator first pulls back and locks the closure trigger 18. FIGS. 14 and 15 show one embodiment of a closure trigger 18 locking mechanism for locking the closure trigger 18 to the pistol grip portion 26 of the handle 6. In the illustrated embodiment, the pistol grip portion 26 includes a hook 150 that is biased to rotate CCW about a pivot point 151 by a torsion spring 152. Also, the closure trigger 18 includes a closure bar 154. As the operator draws in the closure trigger 18, the closure bar 154 engages a sloped portion 156 of the hook 150, thereby rotating the hook 150 upward (or CW in FIGS. 14-15) until the closure bar 154 completely passes the sloped portion 156 into a recessed notch 158 of the hook 150, which locks the closure trigger 18 in place. The operator may release the closure trigger 18 by pushing down on a slide button release 160 on the back or opposite side of the pistol grip portion 26. Pushing down the slide button release 160 rotates the hook 150 CW such that the closure bar 154 is released from the recessed notch 158.

Figure 16:
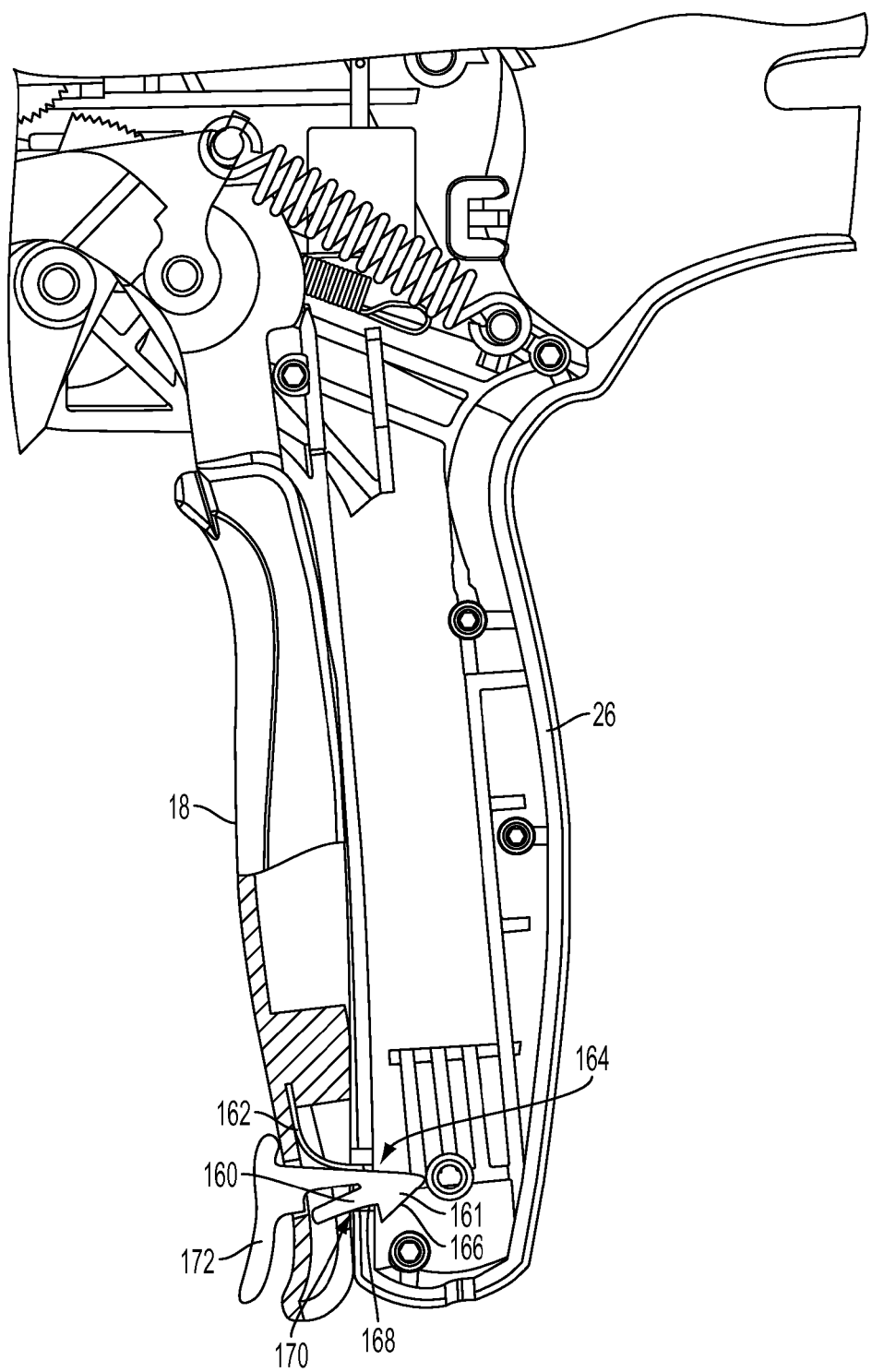
FIG. 16 shows another embodiment of a closure trigger locking mechanism

FIG. 16 shows another closure trigger locking mechanism according to various embodiments. In the embodiment of FIG. 16, the closure trigger 18 includes a wedge 160 having an arrow-head portion 161. The arrow-head portion 161 is biased downward (or CW) by a leaf spring 162. The wedge 160 and leaf spring 162 may be made from, for example, molded plastic. When the closure trigger 18 is retracted, the arrow-head portion 161 is inserted through an opening 164 in the pistol grip portion 26 of the handle 6. A lower chamfered surface 166 of the arrow-head portion 161 engages a lower sidewall 168 of the opening 164, forcing the arrow-head portion 161 to rotate CCW. Eventually the lower chamfered surface 166 fully passes the lower sidewall 168, removing the CCW force on the arrow-head portion 161, causing the lower sidewall 168 to slip into a locked position in a notch 170 behind the arrow-head portion 161.

To unlock the closure trigger 18, a user presses down on a button 172 on the opposite side of the closure trigger 18, causing the arrow-head portion 161 to rotate CCW and allowing the arrow-head portion 161 to slide out of the opening 164.

Figure 17:
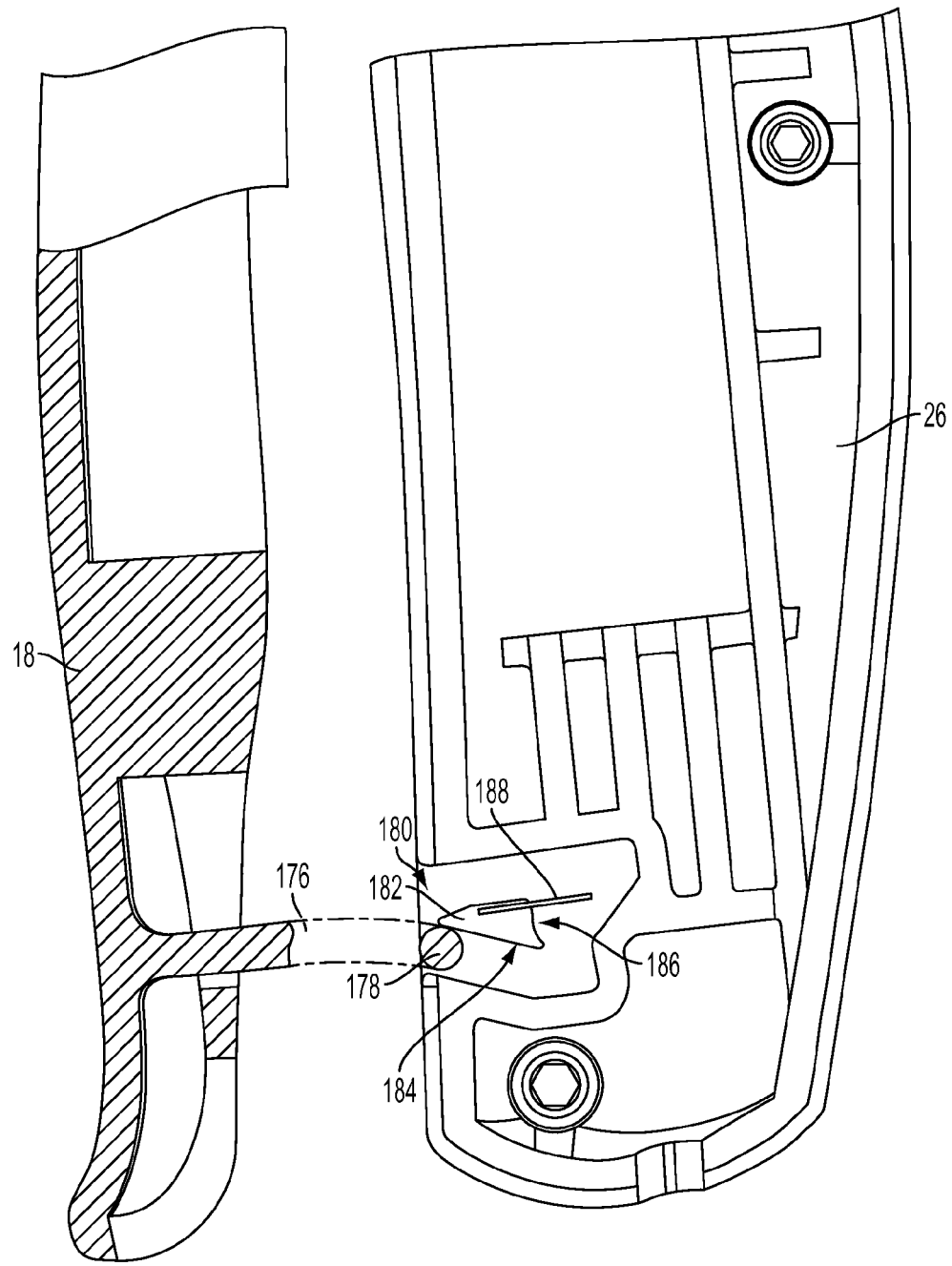
FIGS. 17-22 show another embodiment of a closure trigger locking mechanism.
Figure 18:
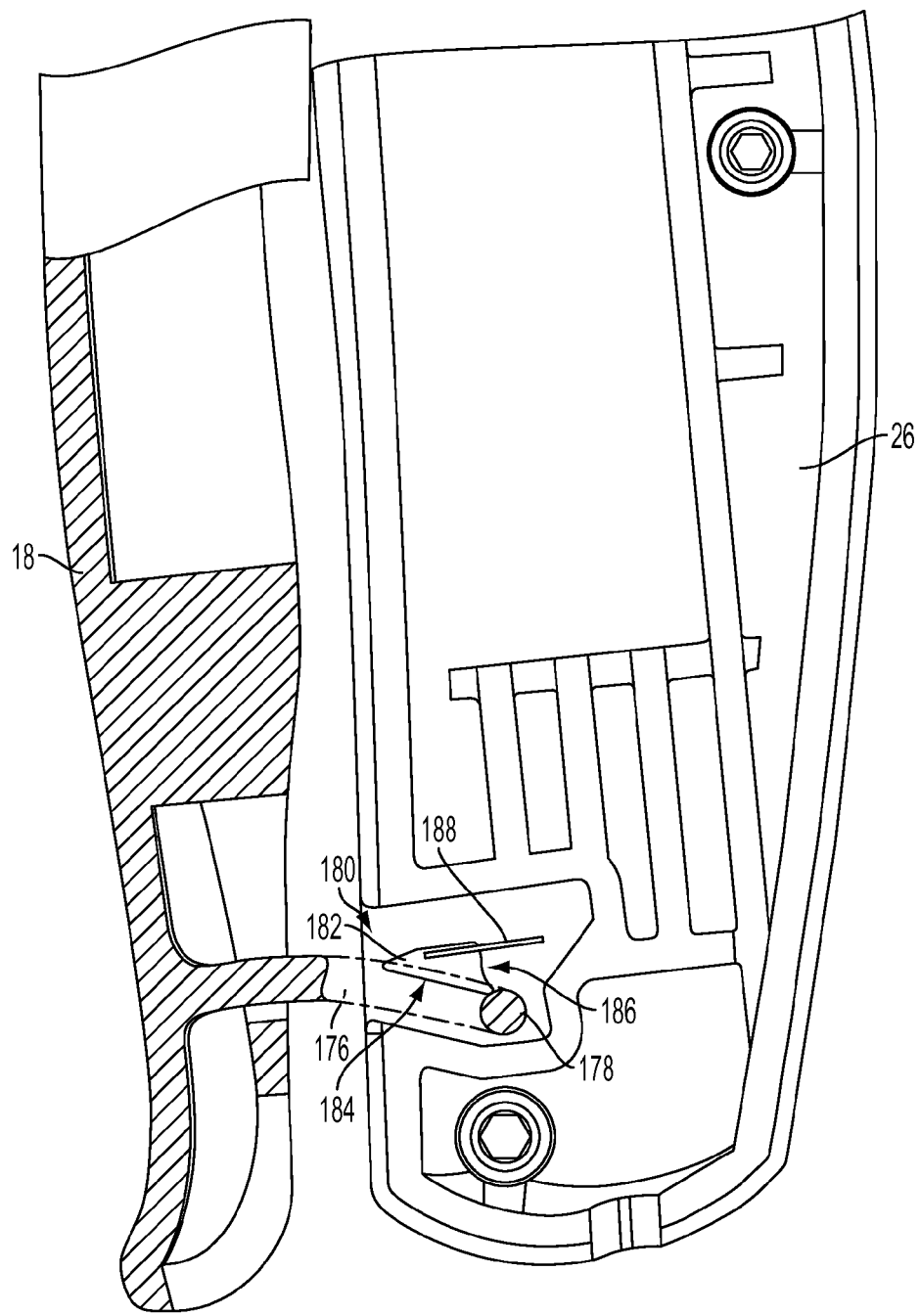
Figure 19:
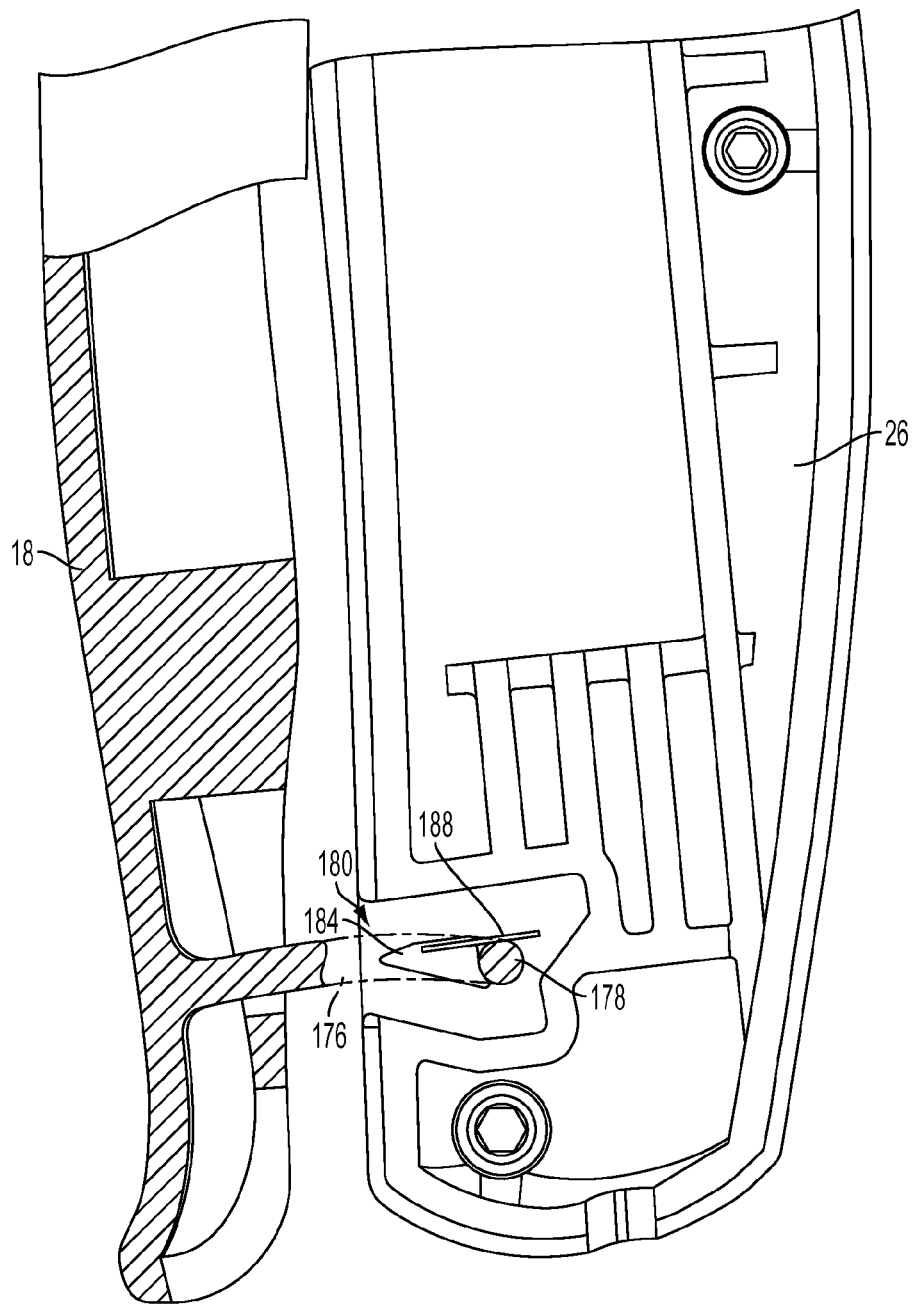

FIGS. 17-22 show another embodiment of a closure trigger locking mechanism. As shown in this embodiment, the closure trigger 18 includes a flexible longitudinal arm 176 that includes a lateral pin 178 extending therefrom. The arm 176 and pin 178 may be made from molded plastic, for example. The pistol grip portion 26 of the handle 6 includes an opening 180 with a laterally extending wedge 182 disposed therein. When the closure trigger 18 is retracted, the pin 178 engages the wedge 182, and the pin 178 is forced downward (e.g., the arm 176 is rotated CW) by the lower surface 184 of the wedge 182, as shown in FIGS. 17 and 18. When the pin 178 fully passes the lower surface 184, the CW force on the arm 176 is removed, and the pin 178 is rotated CCW such that the pin 178 comes to rest in a notch 186 behind the wedge 182, as shown in FIG. 19, thereby locking the closure trigger 18. The pin 178 is further held in place in the locked position by a flexible stop 188 extending from the wedge 184.

Figure 20:
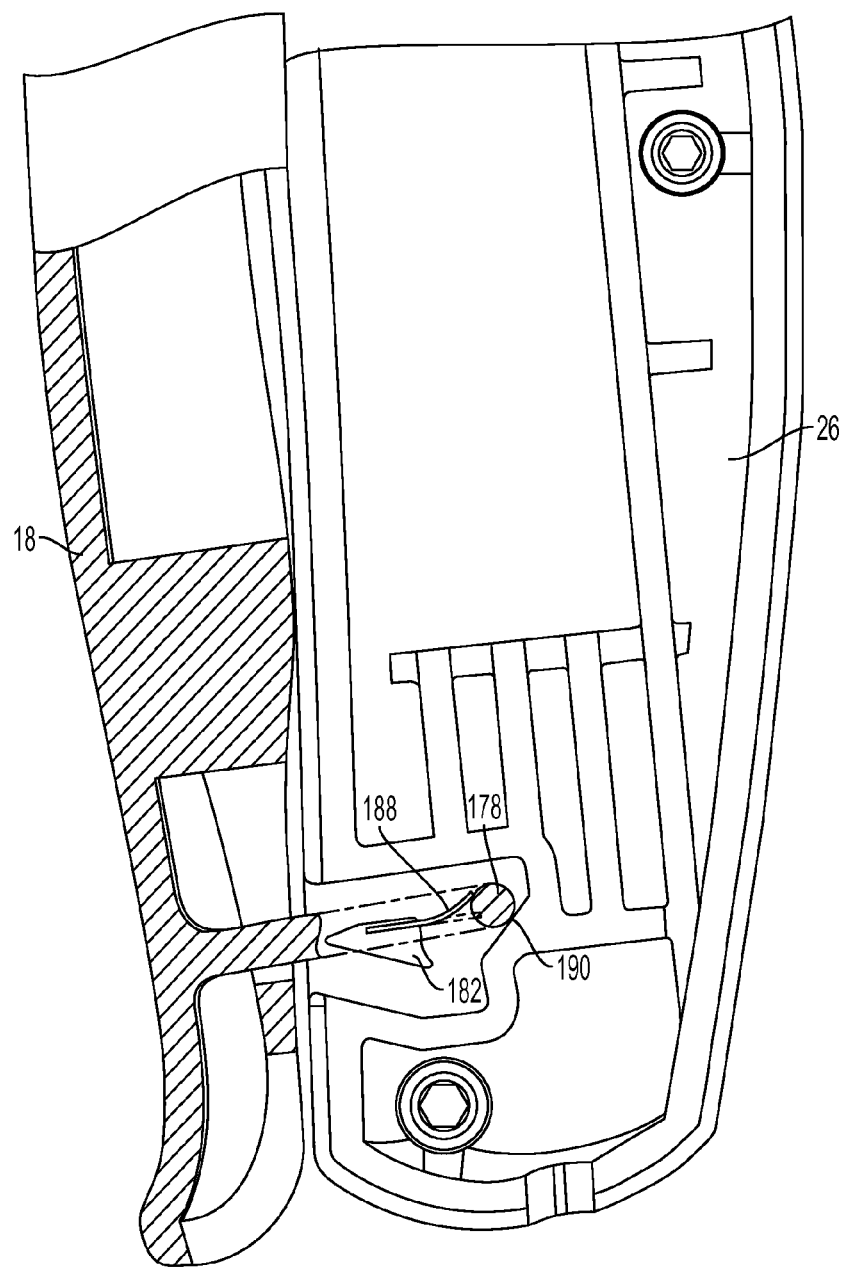
Figure 21:
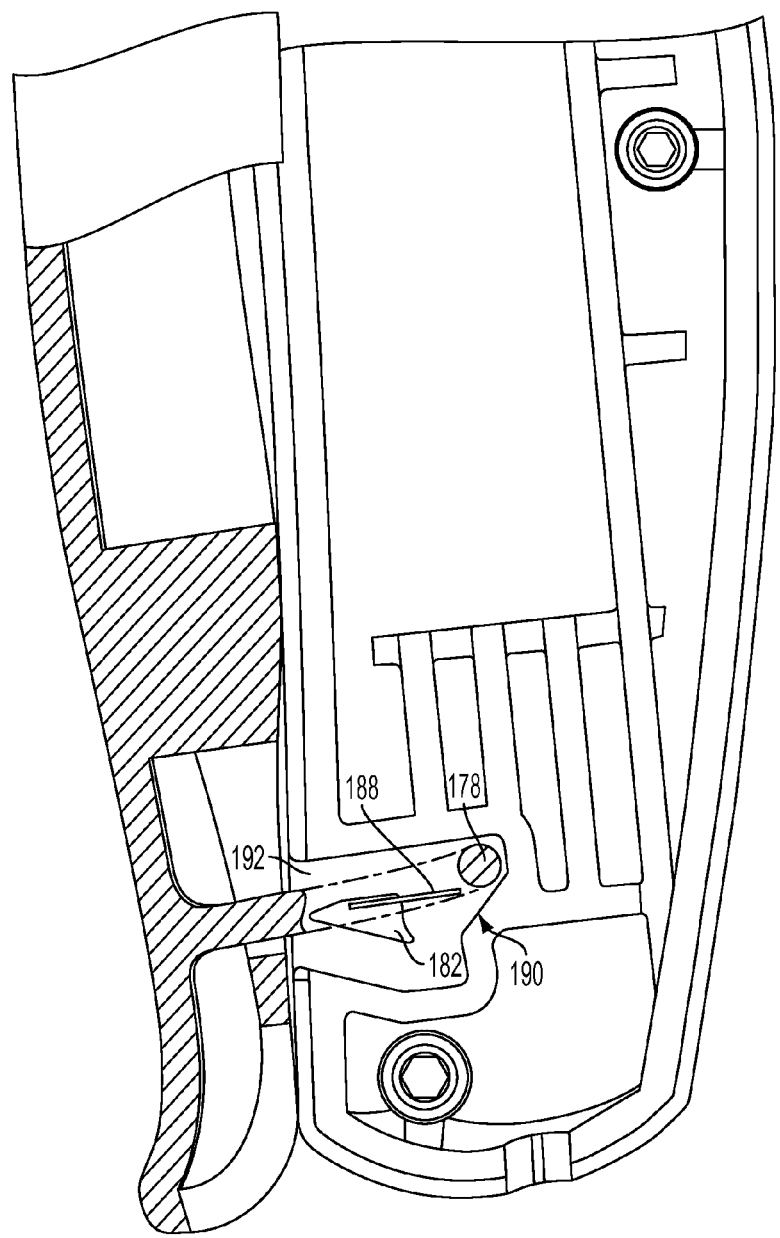
Figure 22:
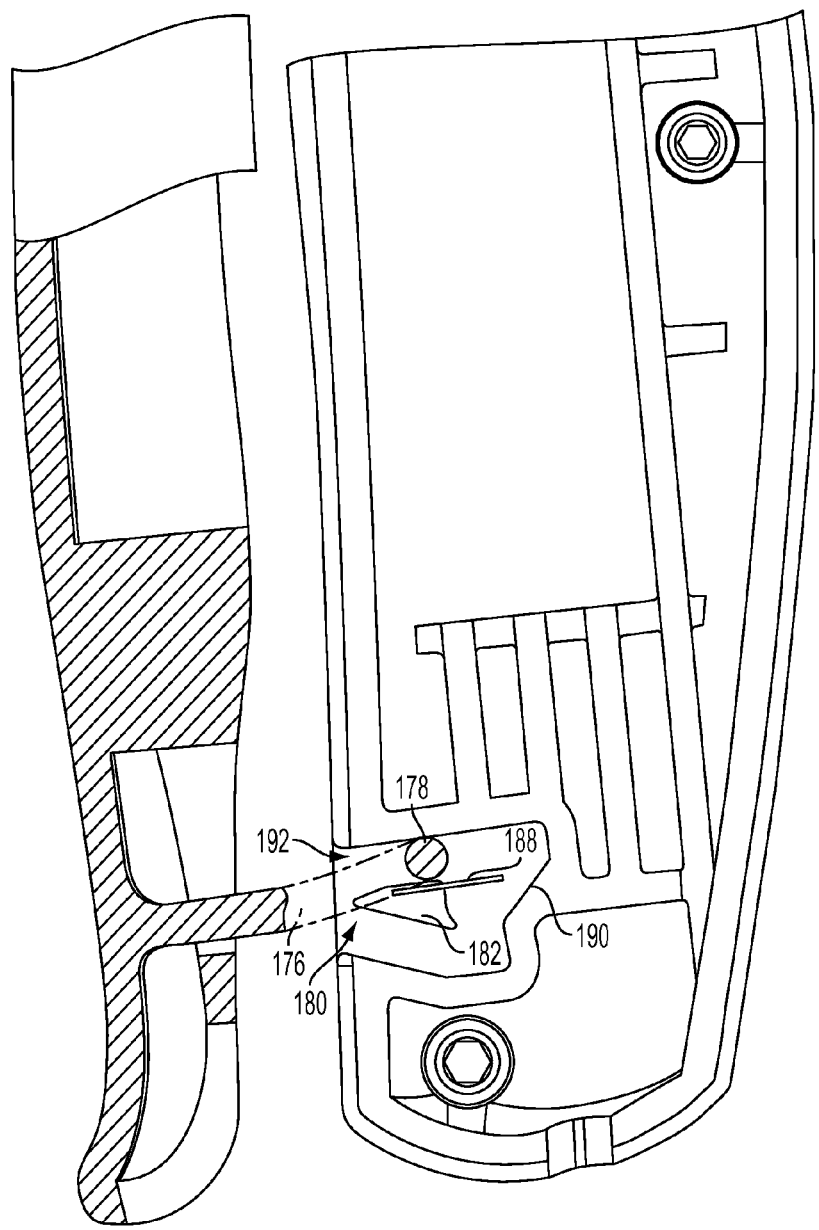

To unlock the closure trigger 18, the operator may further squeeze the closure trigger 18, causing the pin 178 to engage a sloped backwall 190 of the opening 180, forcing the pin 178 upward past the flexible stop 188, as shown in FIGS. 20 and 21. The pin 178 is then free to travel out an upper channel 192 in the opening 180 such that the closure trigger 18 is no longer locked to the pistol grip portion 26, as shown in FIG. 22.

FIGS. 23A-B show a universal joint ("u-joint") 195 that may be employed at the articulation point of a surgical instrument, such as the instrument 10. The second piece 195-2 of the u-joint 195 rotates in a horizontal plane in which the first piece 195-1 lies. FIG. 23A shows the u-joint 195 in a linear (180°) orientation and FIG. 23B shows the u-joint 195 at approximately a 150° orientation. The u-joint 195 may be used instead of the bevel gears 52a-c (see FIG. 4, for example) at the articulation point 14 of the main drive shaft assembly to articulate the end effector 12. FIGS. 24A-B show a torsion cable 197 that may be used in lieu of both the bevel gears 52a-c and the u-joint 195 to realize articulation of the end effector 12.

FIGS. 25-31 illustrate another embodiment of a motorized, two-stroke surgical cutting and fastening instrument 10 with power assist. The embodiment of FIGS. 25-31 is similar to that of FIGS. 6-10 except that instead of the helical gear drum 80, the embodiment of FIGS. 25-31 includes an alternative gear drive assembly. The embodiment of FIGS. 25-31 includes a gear box assembly 200 including a number of gears disposed in a frame 201, wherein the gears are connected between the planetary gear 72 and the pinion gear 124 at the proximate end of the drive shaft 48. As explained further below, the gear box assembly 200 provides feedback to the user via the firing trigger 20 regarding the deployment and loading force of the end effector 12. Also, the user may provide power to the system via the gear box assembly 200 to assist the deployment of the end effector 12. In that sense, like the embodiments described above, the embodiment of FIGS. 25-31 is another power assist, motorized instrument 10 that provides feedback to the user regarding the loading force experienced by the cutting instrument 32.

In the illustrated embodiment, the firing trigger 20 includes two pieces: a main body portion 202 and a stiffening portion 204. The main body portion 202 may be made of plastic, for example, and the stiffening portion 204 may be made out of a more rigid material, such as metal. In the illustrated embodiment, the stiffening portion 204 is adjacent to the main body portion 202, but according to other embodiments, the stiffening portion 204 could be disposed inside the main body portion 202. A pivot pin 207 may be inserted through openings in the firing trigger pieces 202, 204 and may be the point about which the firing trigger 20 rotates. In addition, a spring 222 may bias the firing trigger 20 to rotate in a CCW direction. The spring 222 may have a distal end connected to a pin 224 that is connected to the pieces 202, 204 of the firing trigger 20. The proximate end of the spring 222 may be connected to one of the handle exterior lower side pieces 59, 60.

In the illustrated embodiment, both the main body portion 202 and the stiffening portion 204 include gear portions 206, 208 (respectively) at their upper end portions. The gear portions 206, 208 engage a gear in the gear box assembly 200, as explained below, to drive the main drive shaft assembly and to provide feedback to the user regarding the deployment of the end effector 12.

The gear box assembly 200 may include as shown, in the illustrated embodiment, six (6) gears. A first gear 210 of the gear box assembly 200 engages the gear portions 206, 208 of the firing trigger 20. In addition, the first gear 210 engages a smaller second gear 212, the smaller second gear 212 being coaxial with a large third gear 214. The third gear 214 engages a smaller fourth gear 216, the smaller fourth gear 216 being coaxial with a fifth gear 218. The fifth gear 218 is a 90° bevel gear that engages a mating 90° bevel gear 220 (best shown in FIG. 31) that is connected to the pinion gear 124 that drives the main drive shaft 48.

In operation, when the user retracts the firing trigger 20, a run motor sensor (not shown) is activated, which may provide a signal to the motor 65 to rotate at a rate proportional to the extent or force with which the operator is retracting the firing trigger 20. This causes the motor 65 to rotate at a speed proportional to the signal from the sensor. The sensor is not shown for this embodiment, but it could be similar to the run motor sensor 110 described above. The sensor could be located in the handle 6 such that it is depressed when the firing trigger 20 is retracted. Also, instead of a proportional-type sensor, an on/off type sensor may be used.

Rotation of the motor 65 causes the bevel gears 66, 70 to rotate, which causes the planetary gear 72 to rotate, which causes, via the drive shaft 76, the ring gear 122 to rotate. The ring gear 122 meshes with the pinion gear 124, which is connected to the main drive shaft 48. Thus, rotation of the pinion gear 124 drives the main drive shaft 48, which causes actuation of the cutting/stapling operation of the end effector 12.

Forward rotation of the pinion gear 124 in turn causes the bevel gear 220 to rotate, which causes, by way of the rest of the gears of the gear box assembly 200, the first gear 210 to rotate. The first gear 210 engages the gear portions 206, 208 of the firing trigger 20, thereby causing the firing trigger 20 to rotate CCW when the motor 65 provides forward drive for the end effector 12 (and to rotate CCW when the motor 65 rotates in reverse to retract the end effector 12). In that way, the user experiences feedback regarding loading force and deployment of the end effector 12 by way of the user's grip on the firing trigger 20. Thus, when the user retracts the firing trigger 20, the operator will experience a resistance related to the load force experienced by the end effector 12. Similarly, when the operator releases the firing trigger 20 after the cutting/stapling operation so that it can return to its original position, the user will experience a CW rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portions 206, 208 to rotate CCW, which causes the gears of the gear box assembly 200 to rotate, thereby causing the pinion gear 124 to rotate, which causes the main drive shaft 48 to rotate.

Although not shown in FIGS. 25-31, the instrument 10 may further include reverse motor and stop motor sensors. As described above, the reverse motor and stop motor sensors may detect, respectively, the end of the cutting stroke (full deployment of the knife 32 and sled 33) and the end of retraction operation (full retraction of the knife 32). A circuit similar to that described above in connection with FIG. 11 may be used to appropriately power the motor 65.

FIGS. 32-36 illustrate another embodiment of a two-stroke, motorized surgical cutting and fastening instrument 10 with power assist. The embodiment of FIGS. 32-36 is similar to that of FIGS. 25-31 except that in the embodiment of FIGS. 32-36, the firing trigger 20 includes a lower portion 228 and an upper portion 230. Both portions 228, 230 are connected to and pivot about a pivot pin 207 that is disposed through each portion 228, 230. The upper portion 230 includes a gear portion 232 that engages the first gear 210 of the gear box assembly 200. The spring 222 is connected to the upper portion 230 such that the upper portion is biased to rotate in the CW direction. The upper portion 230 may also include a lower arm 234 that contacts an upper surface of the lower portion 228 of the firing trigger 20 such that when the upper portion 230 is caused to rotate CW the lower portion 228 also rotates CW, and when the lower portion 228 rotates CCW the upper portion 230 also rotates CCW. Similarly, the lower portion 228 includes a rotational stop 238 that engages a lower shoulder of the upper portion 230. In that way, when the upper portion 230 is caused to rotate CCW the lower portion 228 also rotates CCW, and when the lower portion 228 rotates CW the upper portion 230 also rotates CW.

The illustrated embodiment also includes the run motor sensor 110 that communicates a signal to the motor 65 that, in various embodiments, may cause the motor 65 to rotate at a speed proportional to the force applied by the operator when retracting the firing trigger 20. The sensor 110 may be, for example, a rheostat or some other variable resistance sensor, as explained herein. In addition, the instrument 10 may include a reverse motor sensor 130 that is tripped or switched when contacted by a front face 242 of the upper portion 230 of the firing trigger 20. When activated, the reverse motor sensor 130 sends a signal to the motor 65 to reverse direction. Also, the instrument 10 may include a stop motor sensor 142 that is tripped or actuated when contacted by the lower portion 228 of the firing trigger 20. When activated, the stop motor sensor 142 sends a signal to stop the reverse rotation of the motor 65.

Figure 32:
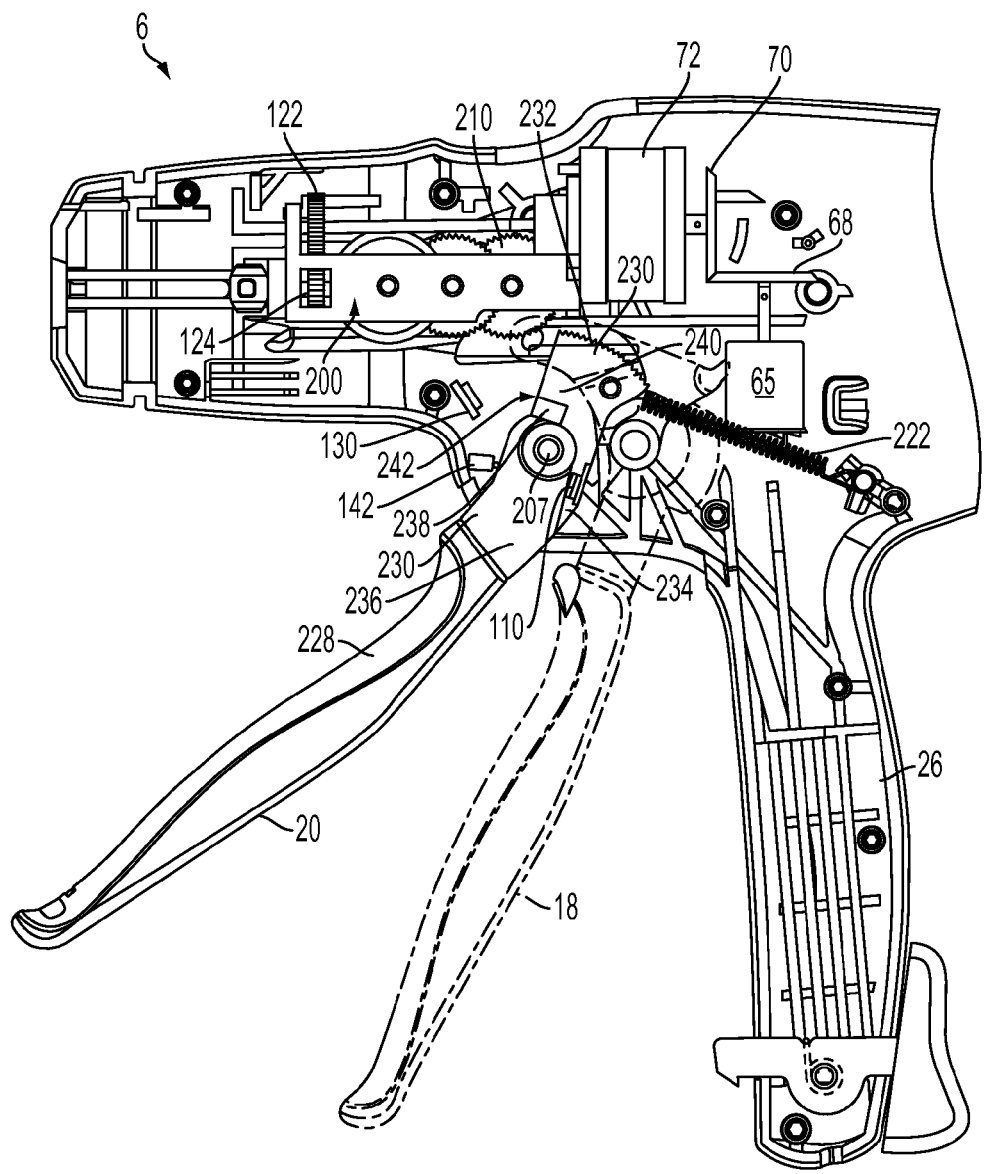
Figure 33:
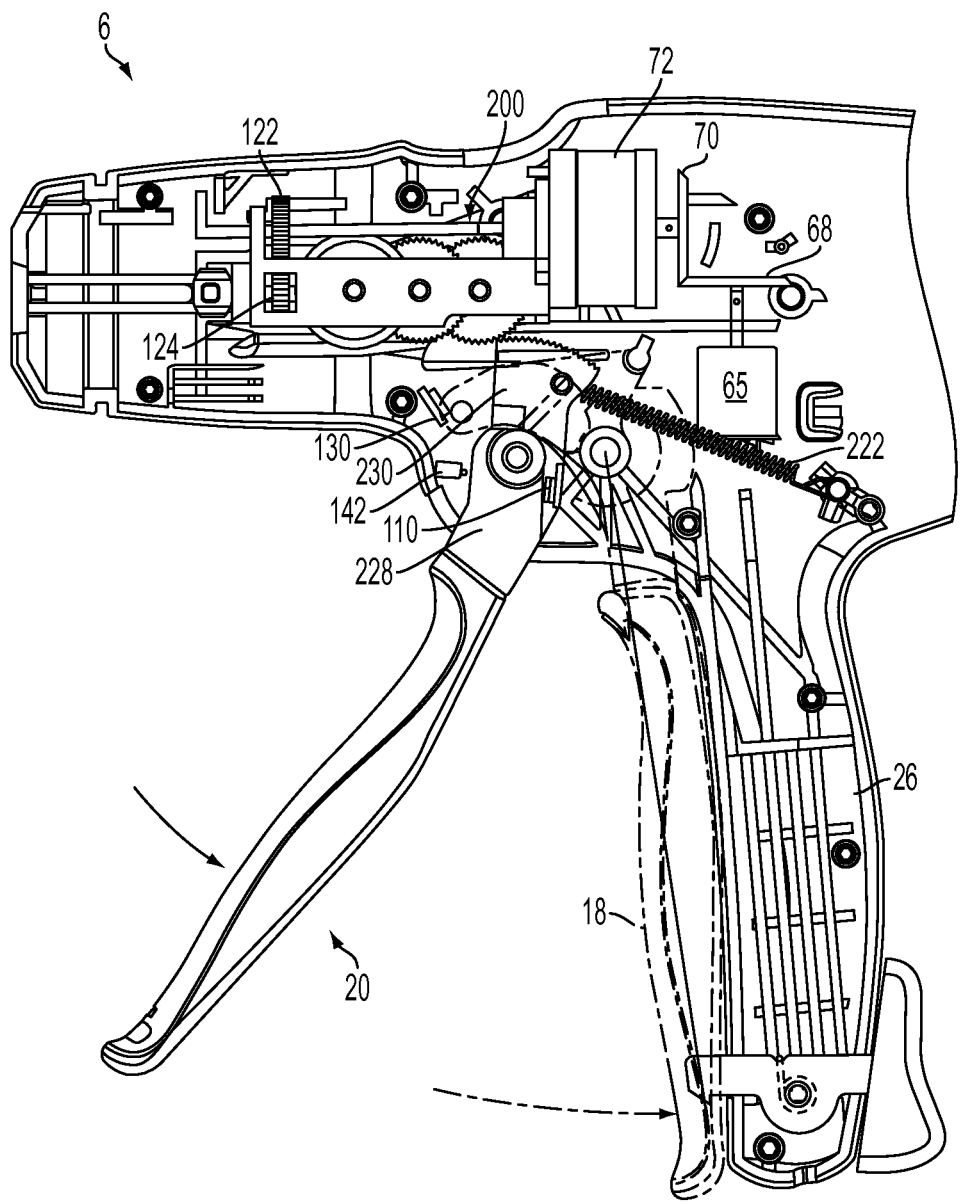
Figure 34:
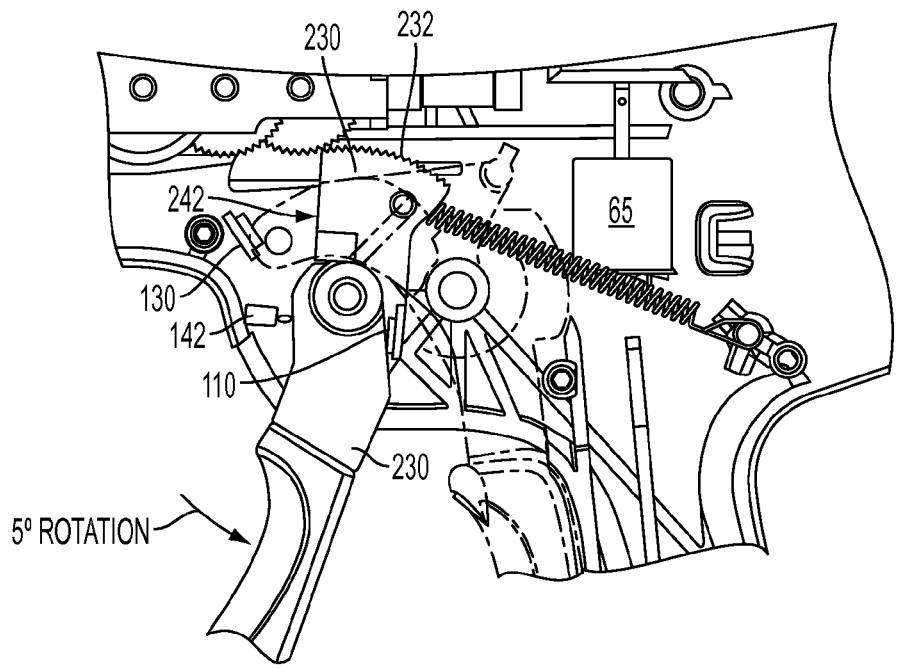
Figure 35:
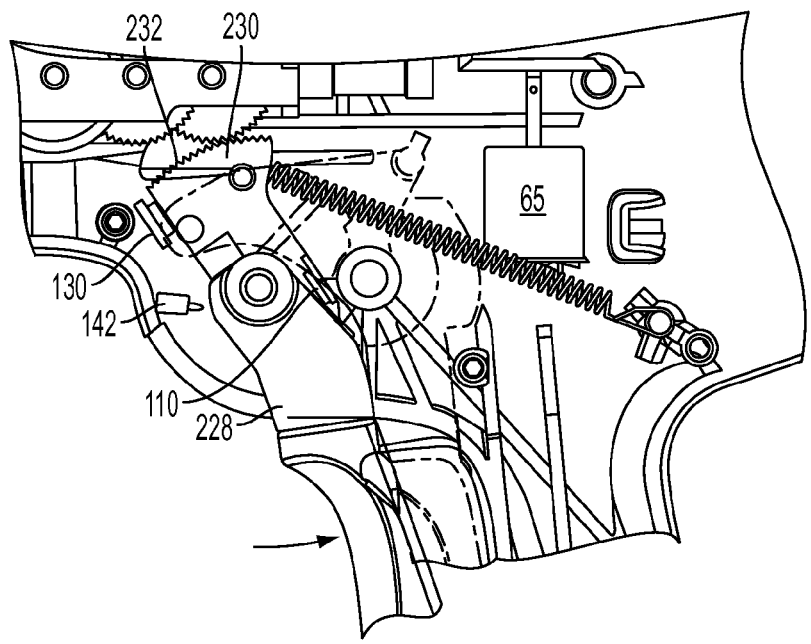
Figure 36:
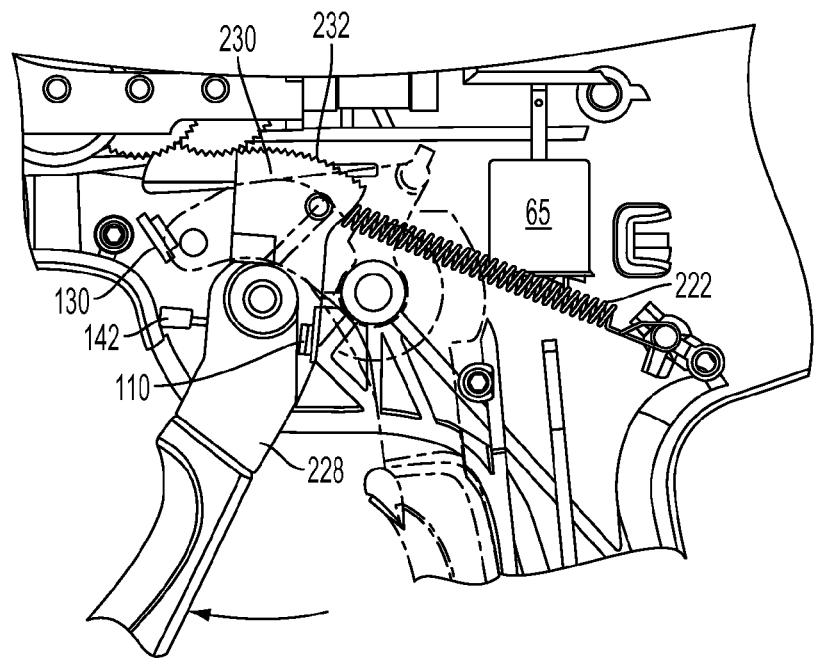

In operation, when an operator retracts the closure trigger 18 into the locked position, the firing trigger 20 is retracted slightly (through mechanisms known in the art, including U.S. Pat. No. 6,978,921, entitled "Surgical Stapling Instrument Incorporating An E-Beam Firing Mechanism" and U.S. Pat. No. 6,905,057, entitled "Surgical Stapling Instrument Incorporating A Firing Mechanism Having A Linked Rack Transmission," both of which are incorporated herein by reference) so that the user can grasp the firing trigger 20 to initiate the cutting/stapling operation, as shown in FIGS. 32 and 33. At that point, as shown in FIG. 33, the gear portion 232 of the upper portion 230 of the firing trigger 20 moves into engagement with the first gear 210 of the gear box assembly 200. When the operator retracts the firing trigger 20, according to various embodiments, the firing trigger 20 may rotate a small amount, such as five degrees, before tripping the run motor sensor 110, as shown in FIG. 34. Activation of the sensor 110 causes the motor 65 to forward rotate at a rate proportional to the retraction force applied by the operator. The forward rotation of the motor 65 causes, as described above, the main drive shaft 48 to rotate, which causes the knife 32 in the end effector 12 to be deployed (e.g., begin traversing the channel 22). Rotation of the pinion gear 124, which is connected to the main drive shaft 48, causes the gears 210-220 in the gear box assembly 200 to rotate. Since the first gear 210 is in engagement with the gear portion 232 of the upper portion 230 of the firing trigger 20, the upper portion 230 is caused to rotate CCW, which causes the lower portion 228 to also rotate CCW.

When the knife 32 is fully deployed (e.g., at the end of the cutting stroke), the front face 242 of the upper portion 230 trips the reverse motor sensor 130, which sends a signal to the motor 65 to reverse rotational direction. This causes the main drive shaft assembly to reverse rotational direction to retract the knife 32. Reverse rotation of the main drive shaft assembly causes the gears 210-220 in the gear box assembly to reverse direction, which causes the upper portion 230 of the firing trigger 20 to rotate CW, which causes the lower portion 228 of the firing trigger 20 to rotate CW until the front face 242 of the upper portion 230 trips or actuates the stop motor sensor 142 when the knife 32 is fully retracted, which causes the motor 65 to stop. In that way, the user experiences feedback regarding deployment of the end effector 12 by way of the user's grip on the firing trigger 20. Thus, when the user retracts the firing trigger 20, the operator will experience a resistance related to the deployment of the end effector 12 and, in particular, to the loading force experienced by the knife 32. Similarly, when the operator releases the firing trigger 20 after the cutting/stapling operation so that it can return to its original position, the user will experience a CW rotation force from the firing trigger 20 that is generally proportional to the reverse speed of the motor 65.

It should also be noted that in this embodiment the user can apply force (either in lieu of or in addition to the force from the motor 65) to actuate the main drive shaft assembly (and hence the cutting/stapling operation of the end effector 12) through retracting the firing trigger 20. That is, retracting the firing trigger 20 causes the gear portion 232 of the upper portion 230 to rotate CCW, which causes the gears of the gear box assembly 200 to rotate, thereby causing the pinion gear 124 to rotate, which causes the main drive shaft assembly to rotate.

The above-described embodiments employed power-assist user feedback systems, with or without adaptive control (e.g., using a sensor 110, 130, and 142 outside of the closed loop system of the motor, gear drive train, and end effector) for a two-stroke, motorized surgical cutting and fastening instrument. That is, force applied by the user in retracting the firing trigger 20 may be added to the force applied by the motor 65 by virtue of the firing trigger 20 being geared into (either directly or indirectly) the gear drive train between the motor 65 and the main drive shaft 48. In other embodiments, the user may be provided with tactile feedback regarding the position of the knife 32 in the end effector 12, but without having the firing trigger 20 geared into the gear drive train. FIGS. 37-40 illustrate one embodiment of a motorized surgical cutting and fastening instrument 10 with such a tactile position feedback system.

In the illustrated embodiment of FIGS. 37-40, the firing trigger 20 may have a lower portion 228 and an upper portion 230, similar to the instrument 10 shown in FIGS. 32-36. Unlike the embodiment of FIG. 32-36, however, the upper portion 230 does not have a gear portion that mates with part of the gear drive train. Instead, the instrument 10 includes a second motor 265 with a threaded rod 266 threaded therein. The threaded rod 266 reciprocates longitudinally in and out of the motor 265 as the motor 265 rotates, depending on the direction of rotation. The instrument 10 also includes an encoder 268 that is responsive to the rotations of the main drive shaft 48 for translating the incremental angular motion of the main drive shaft 48 (or other component of the main drive assembly) into a corresponding series of digital signals, for example. In the illustrated embodiment, the pinion gear 124 includes a proximate drive shaft 270 that connects to the encoder 268.

The instrument 10 also includes a control circuit (not shown), which may be implemented using a microcontroller or some other type of integrated circuit, that receives the digital signals from the encoder 268. Based on the signals from the encoder 268, the control circuit may calculate the stage of deployment of the knife 32 in the end effector 12. That is, the control circuit can calculate if the knife 32 is fully deployed, fully retracted, or at an intermittent stage. Based on the calculation of the stage of deployment of the end effector 12, the control circuit may send a signal to the second motor 265 to control its rotation to thereby control the reciprocating movement of the threaded rod 266.

Figure 37:
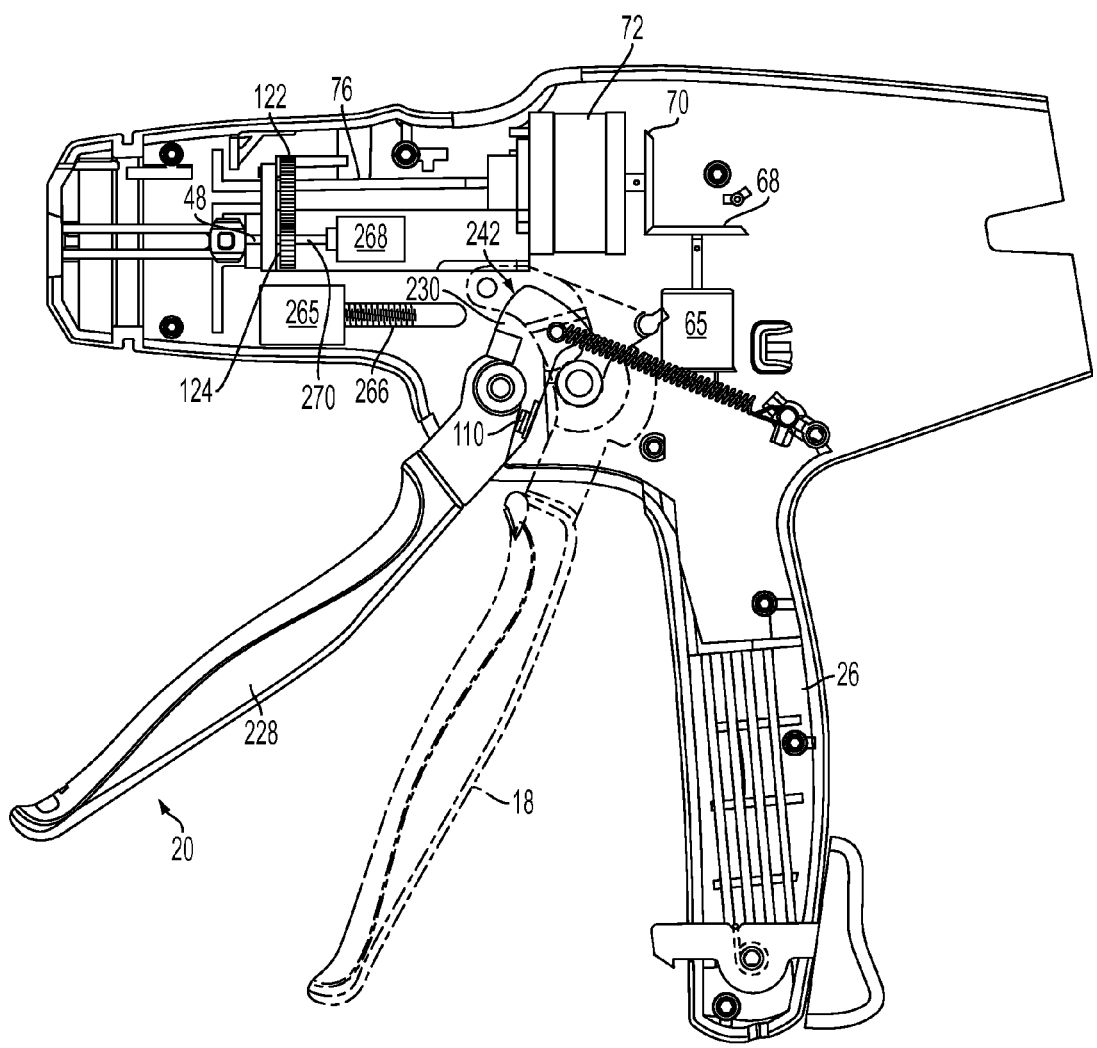
Figure 38:
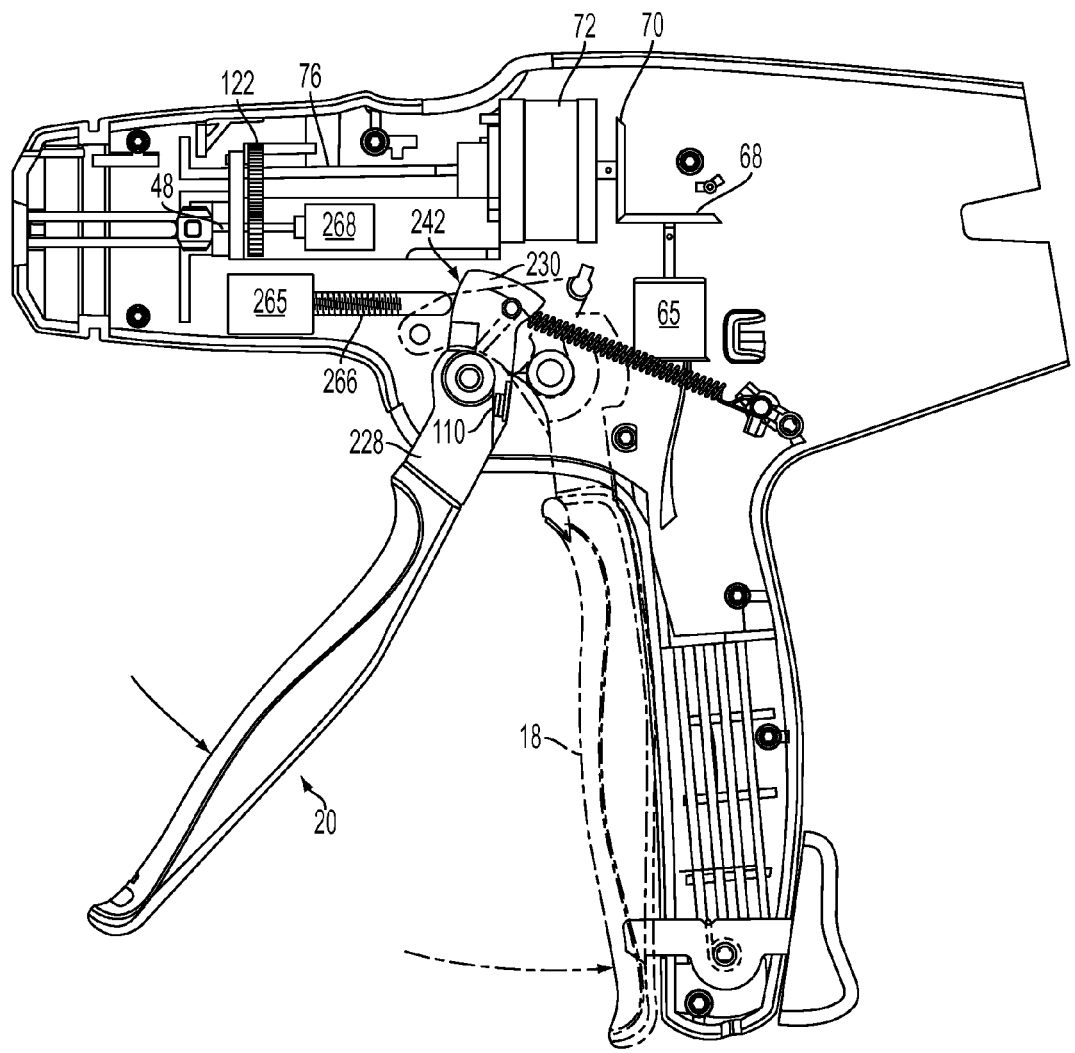
Figure 39:
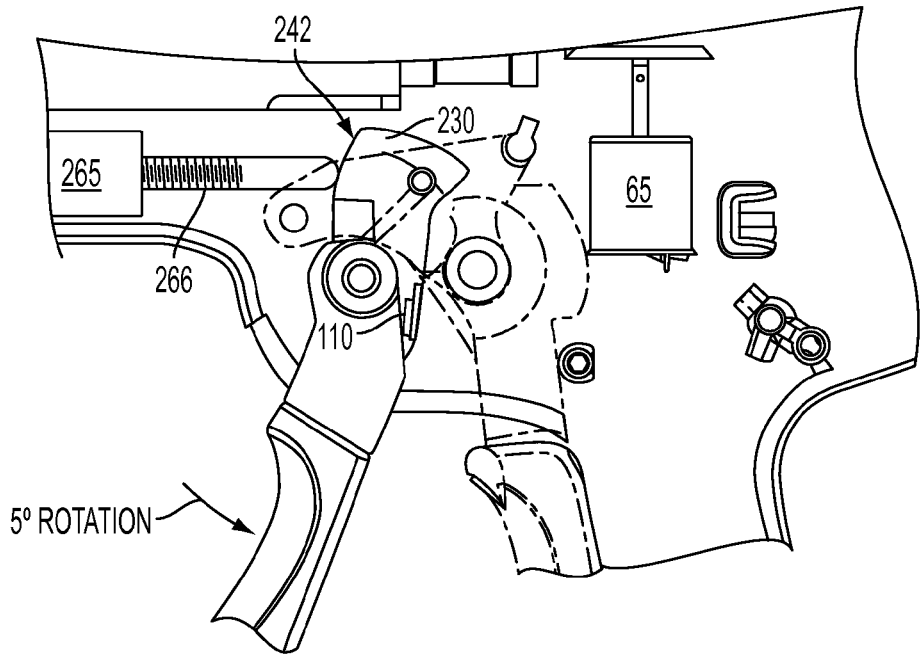
Figure 40:
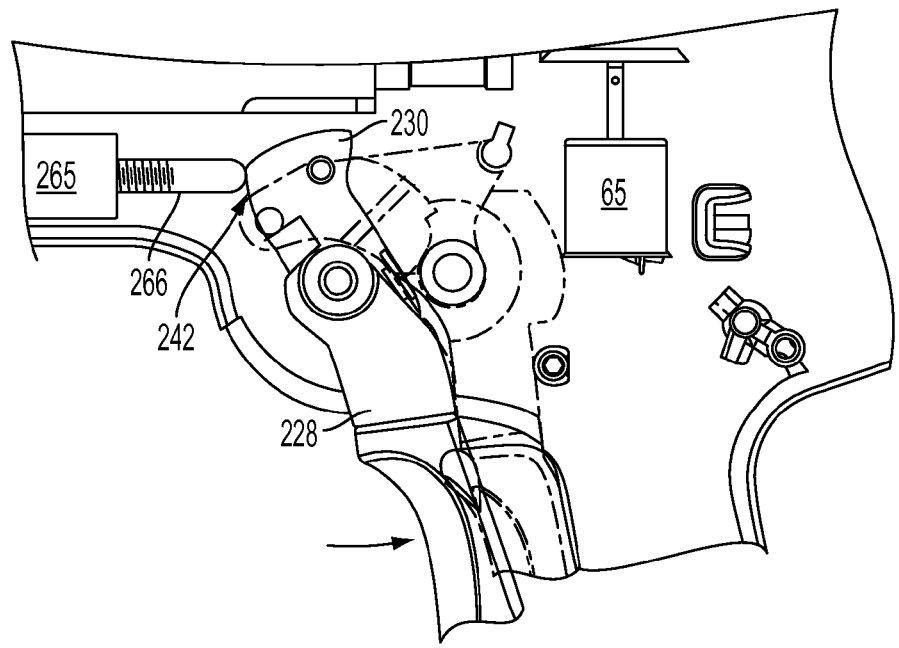

In operation, as shown in FIG. 37, when the closure trigger 18 is not locked into the clamped position, the firing trigger 20 rotated away from the pistol grip portion 26 of the handle 6 such that the front face 242 of the upper portion 230 of the firing trigger 20 is not in contact with the proximate end of the threaded rod 266. When the operator retracts the closure trigger 18 and locks it in the clamped position, the firing trigger 20 rotates slightly towards the closure trigger 18 so that the operator can grasp the firing trigger 20, as shown in FIG. 38. In this position, the front face 242 of the upper portion 230 contacts the proximate end of the threaded rod 266.

As the user then retracts the firing trigger 20, after an initial rotational amount (e.g., 5 degrees of rotation) the run motor sensor 110 may be activated such that, as explained above, the sensor 110 sends a signal to the motor 65 to cause it to rotate at a forward speed proportional to the amount of retraction force applied by the operator to the firing trigger 20. Forward rotation of the motor 65 causes the main drive shaft 48 to rotate via the gear drive train, which causes the knife 32 and sled 33 to travel down the channel 22 and sever tissue clamped in the end effector 12. The control circuit receives the output signals from the encoder 268 regarding the incremental rotations of the main drive shaft assembly and sends a signal to the second motor 265 to cause the second motor 265 to rotate, which causes the threaded rod 266 to retract into the motor 265. This allows the upper portion 230 of the firing trigger 20 to rotate CCW, which allows the lower portion 228 of the firing trigger to also rotate CCW. In that way, because the reciprocating movement of the threaded rod 266 is related to the rotations of the main drive shaft assembly, the operator of the instrument 10, by way of his/her grip on the firing trigger 20, experiences tactile feedback as to the position of the end effector 12. The retraction force applied by the operator, however, does not directly affect the drive of the main drive shaft assembly because the firing trigger 20 is not geared into the gear drive train in this embodiment.

By virtue of tracking the incremental rotations of the main drive shaft assembly via the output signals from the encoder 268, the control circuit can calculate when the knife 32 is fully deployed (e.g., fully extended). At this point, the control circuit may send a signal to the motor 65 to reverse direction to cause retraction of the knife 32. The reverse direction of the motor 65 causes the rotation of the main drive shaft assembly to reverse direction, which is also detected by the encoder 268. Based on the reverse rotation detected by the encoder 268, the control circuit sends a signal to the second motor 265 to cause it to reverse rotational direction such that the threaded rod 266 starts to extend longitudinally from the motor 265. This motion forces the upper portion 230 of the firing trigger 20 to rotate CW, which causes the lower portion 228 to rotate CW. In that way, the operator may experience a CW force from the firing trigger 20, which provides feedback to the operator as to the retraction position of the knife 32 in the end effector 12. The control circuit can determine when the knife 32 is fully retracted. At this point, the control circuit may send a signal to the motor 65 to stop rotation.

According to other embodiments, rather than having the control circuit determine the position of the knife 32, reverse motor and stop motor sensors may be used, as described above. In addition, rather than using a proportional sensor 110 to control the rotation of the motor 65, an on/off switch or sensor can be used. In such an embodiment, the operator would not be able to control the rate of rotation of the motor 65. Rather, it would rotate at a preprogrammed rate.

FIG. 43 is a partial cross-sectional view of a surgical instrument 300 with various components removed for clarity. The surgical instrument 300 has a rack 302 (shown in cross-section) for driving an end effector (not shown). A pinion gear 304 engages with the rack 302 such that rotation of the pinion gear 304 in a CCW direction distally translates the rack 302 and rotation of the pinion gear 304 in the CW direction proximally translates the rack 302. The pinion gear 304 may rotate about an axel 306 and may be driven by a motor which is operationally controlled by a trigger (not shown). In one embodiment, the pinion gear 304 may be biased in a first direction 303 by a biasing member 308. The biasing member 308 may be a spring, as illustrated, although any other suitable biasing technique may be used. The surgical instrument 300 may comprise a lever 310 that may be used, for example, in the event the energy level of the surgical instrument's power source falls below sufficient operational levels. In one embodiment, the level 310 is generally concealed from the user by a door 312, which may be removed by the user to access the lever 310. The lever 310 may be rotatable about a pivot 314 in a direction indicated by arrow 316. A locking cam 318 may be attached to the lever 310 such that rotation of the lever 310 about the pivot 314 rotates the locking cam 318. In some embodiments, the locking cam 318 is unitary with the lever 310.

Figure 44B:
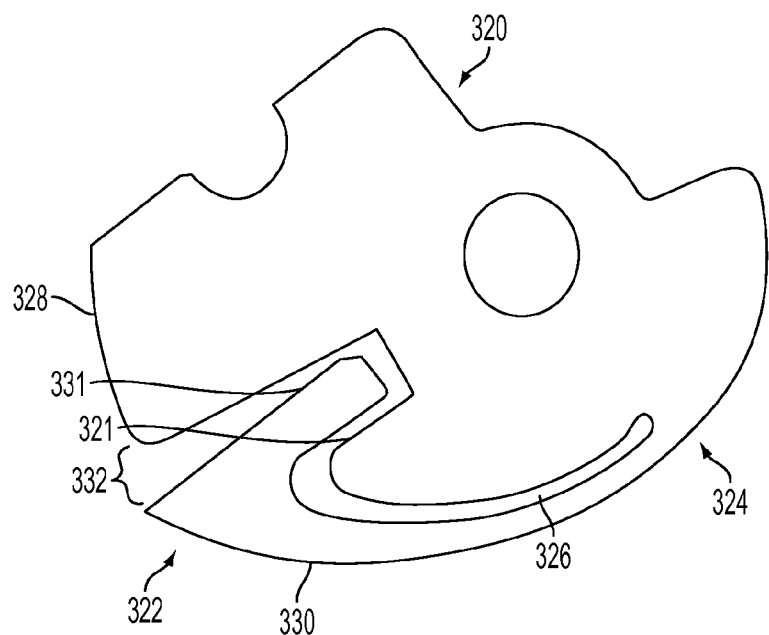

FIGS. 44A and 44B illustrate the locking cam 318 during various states of operation. The locking cam 318 comprises a body portion 320 and a spring portion 322 that may pivot, or otherwise flex, with respect to the body portion 320 about a hinge portion 324. The hinge portion 324 may comprise, for example, a living hinge. In one embodiment, the body portion 320 and the spring portion 322 are unitary and formed from a single piece of material. The locking cam 318 may define a clearance 326 that allows the spring portion 322 to pivot toward the body portion 320. The spring portion 322 may have a tooth 331 that is received by a notch 321 in the body portion 320. On their respective outer peripheries, the body portion 320 may have a first contacting surface 328 and the spring portion 322 may have a second contacting surface 330. In the closed position (FIG. 44A), the first contacting surface 328 is generally aligned with the second contacting surface 330 such that the outer periphery of the locking cam 318 has a generally continuous cammed surface. In the open position (FIG. 44B), the spring portion 322 pivots away from the body portion 320 to increase the clearance 326. A gap 332 is created between the first contacting surface 328 and the second contacting surface 330.

Referring now to FIGS. 43, 44A, and 44B, upon rotation of the lever 310 in the direction indicated by arrow 316, the locking cam 318 is rotated and the second outer surface 330 of the spring portion 322 first contacts a top surface 342 of the pinion gear 304. As a result of this contact, the spring portion 322 is pivoted toward the body portion 320 to create a generally continuous periphery. As the locking cam 318 continues to rotate, the second contacting surface 330 and then the first contacting surface 328 exerts force on the pinion gear 304 to overcome the biasing force applied by the biasing member 308. As a result, the pinion gear 304 is pushed in the direction indicated by arrow 324 as the lever 310 is rotated in the direction indicated by arrow 316. The movement of the pinion gear 304 decouples it from the rack 320 allowing the rack 320 to translate freely. Once the spring portion 322 clears the top surface 342 of the pinion gear 304, it pivots to the open position (FIG. 44B) to lock the locking cam 318 into place. Once in the open position, the locking cam 318 will be impeded from rotating in the direction indicated by arrow 344 (FIG. 43) due to the engagement of the spring portion 322 with the pinion gear 304.

FIGS. 45A, 45B, and 45C show a locking cam 418 and a gear 404 during three stages of operation. Various components have been removed and/or simplified for clarity. As illustrated, the locking cam 418 may be manufactured from a single piece of material. The locking cam 418 comprises a spring portion 422 that is pivotable with respect to a body portion 420. FIG. 45A shows the locking cam 418 in a non-engaged position. In this position, a distal portion 423 of the spring portion 422 is separated from the body portion 420. As illustrated in FIG. 45B, when the locking cam 418 is rotated in the direction indicated by arrow 416, the spring portion 422 is drawn toward the body portion 420 to create a generally continuous periphery spanning the spring portion 422 and the body portion 420. As the locking cam 418 contacts a central hub 442, the pinion gear 404 moves in the direction indicated by arrow 443. As the locking cam 418 continues to rotate in the direction indicated by arrow 416, eventually the spring portion 422 passes over the central hub 442. As shown in FIG. 45C, when the distal portion 423 of the spring portion 422 separates from the body portion 420, it engages the teeth of the pinion gear 404 to lock the locking cam 418 into an engaged position. Accordingly, in various embodiments, while the locking cam 418 may be made from a single piece of material, it may function as two parts (e.g., a cam and a locking mechanism).

FIG. 46 illustrates one embodiment of a surgical instrument 500. The instrument 500 comprises a handle 502, a pistol grip 501, a trigger 504 and an end effector 505. According to various embodiments, the handle 502, trigger 504 and end effector 505 may operate in a manner similar to that of the various handles 6, triggers, 18, 20 and end effectors 12 described herein. In addition to, or instead of, the functionality described herein above, the end effector 501 may comprise surgical implements for cutting, clasping, laser cutting and/or coagulation, RF cutting and/or coagulation, ultrasonic cutting and/or coagulation, for example.

The handle 502 of the instrument 500 may house at least one battery unit 506. The battery unit 506 may comprise a single battery or a plurality of batteries arranged in a series and/or parallel configuration. The handle 502 may comprise a battery dock 508 to which the battery unit 506 may be attached. The battery dock 508 may be any suitable structure for coupling the battery unit 506 to the instrument 500. For example, the battery dock 508 may be a cavity in the handle 502 configured to receive at least a portion of the battery unit 506, as illustrated. In other embodiments, the battery dock 508 may be implemented using a variety of other structures. In one embodiment, the battery dock 508 is a post that is received by the battery unit 506. In one embodiment, the pistol grip 501 comprises the battery dock 508. In any event, as discussed in more detail below, the battery dock 508 may comprise a protruding portion to interact with the battery unit 506 upon attachment of the battery unit 506 to the handle 502. Once attached, the battery unit 506 may be electrically connected to and may provide power to a circuit 514 of the instrument 500. The circuit may be located in the handle 502, as shown, in the end effector 505, or in any combination of locations within the instrument 500. In use, the circuit 514 may power the operation of at least one surgical implement at the end effector 505. For example, the circuit 514 may comprise an electric motor for operating an electrically powered cutter, clasper, or other mechanical device. In addition to, or instead of a motor, the circuit 514 may comprise suitable circuit components for implementing an RF, ultrasonic, or other type of non-motor-powered surgical implement.

FIGS. 47A, 47B, 47C schematically illustrate the battery unit 506 and a portion of the instrument 500. The battery unit 506 may comprise a drain that automatically completes a circuit within the battery unit 506 upon attachment to the instrument 500. The drain serves to slowly reduce the charge of the battery unit 506 over time. Once the battery unit 506 has been sufficiently drained it may be disposed as non-hazardous waste, for example. The battery unit 506 may comprise a voltage source 510. In one embodiment, the voltage source 510 is a lithium battery and comprises at least one cell selected from the group consisting of a CR123 cell and a CR2 cell. As is to be appreciated, any suitable voltage source may be used. The battery unit 506 also comprises a drain 512 that is electrically coupled to the voltage source 510 when a switch 516 is closed. The battery unit 506 and the instrument 500 each comprise electrically conductive contacts 518, 520, respectively, that are placed into contact upon attachment of the battery unit 506 to the instrument 500. FIG. 47A illustrates the battery in a non-attached position. The switch 516 is in an open position and the voltage source 510 may be in a fully charged condition. FIG. 47B illustrates that battery unit 506 in an attached position. The conductive contacts 518 of the battery unit 506 are in electrical communication with the contacts 520 of the instrument thereby allowing the battery unit 506 to supply energy to the circuit 514 (FIG. 46). In the attached position, the switch 516 transitions to the closed position to electrically couple the voltage source 510 to the drain 512. Energy will flow from the voltage source 510 through the drain 512 during operation of the instrument. In other words, the drain 512 will be draining the charge from the voltage source 510 concurrently as the battery unit 506 is supplying operational power to the instrument 500. As discussed in more detail below, a portion of the instrument 500 may physically interact with the drain 512 during attachment of the battery unit 506 to the instrument 500 to transition the switch 516 from the open to the closed state. FIG. 47C illustrates the battery unit 506 in a non-attached position. In one embodiment, the switch 516 remains in the closed position to continue to drain the voltage source 510 even after the battery unit 506 has been detached from the instrument 500.

FIG. 48 is a graph 600 of the voltage level of the battery unit 506 over time, as measured from the time of attachment to the instrument 500, in accordance with one non-limiting embodiment. The graph 600 is illustrates the voltage levels of a 6V cell of the battery unit 506. The graph 600 is merely representative of one embodiment of the battery unit 506. As is to be appreciated, while the graph 600 illustrates a 6 VDC power supply, the battery unit 506 may supply any suitable voltage, such as 9 VDC, 12 VDC or 18 VDC, for example. As discussed in more detail below, the battery unit 506 may comprise multiple cells arranged in a parallel and/or series configuration. The graph 600 includes three example discharge curves 602, 604, 606. As illustrated by the first discharge curve 602, the voltage of the power source 510 drops below 2.0 volts after around 28 hours. As illustrated by the second discharge curve 604, the voltage of the power source 510 drops below 2.0 volts after around 30 hours. As illustrated by the third discharge curve 606, the voltage of the power source 510 drops below 2.0 volts after around 33 hours. The overall shape of the discharge curve may depend upon, for example, the level of activity of the instrument 500 during the surgical procedure. For example, the instrument associated with the first discharge curve 602 was more heavily used during the surgical procedure than the instrument associated with discharge curve 606. In any event, the drain 512 maintains the voltage level of the battery unit 506 at a satisfactory level for a certain time period to ensure that the instrument can be used for its intended purpose during the course of the surgical procedure. For example, in one embodiment, the voltage level of the battery unit 506 is maintained around 6 volts for approximately 12 hours. After 12 hours, the voltage level gradually decreases to a non-hazardous level. As is to be appreciated, the drain 512 may be calibrated to deplete the voltage source faster or slower.

In one embodiment, a resistive element is use to reduce the energy level of the voltage source. FIG. 49A is a simplified circuit diagram of a battery unit 616 comprising a drain 612. The battery unit 616 may be attached to an instrument 500, for example, via its contacts 618. In this embodiment, the battery unit 616 comprises a first grouping of cells 610 and a second grouping of cells 611. In one embodiment, the first and second grouping of cells 610, 611 are lithium batteries. The first and second grouping of cells 610, 611 may each have a plurality of separate cells 610a, 610b, 611a, 611b arranged in a parallel formation. For example, the first and second grouping of cells 610, 611 may each be 6 VDC and arranged in a series configuration to produce 12 VDC at the contacts 618 of the battery unit 616 when fully charged. The cells 610a, 610b, 611a, 611b, however, may be electrically connected to one another in series or parallel or any other combination thereof.

In one embodiment, the drain 612 comprises a first resistive element 622 and a second resistive element 624. As is to be appreciated, in some embodiments, the battery unit 616 may comprise, for example, multiple drains 612 each having more or less than two resistive elements or other circuitry. In the illustrated embodiment, the first resistive element 622 is coupled across a first anode 626 and a first cathode 628 of the first grouping of cells 610 through a first switch 630. The first resistive element 624 may be coupled across a second anode 632 and a second cathode 634 of the second grouping of cells 611 through a second switch 636. The first and second switches 630, 636 may be closed upon attachment of the battery unit 616 to the surgical instrument 500 in order to initiate the draining of the first and second grouping of cells 610, 611.

The value of the resistive elements utilized by the drain 612 may vary based on implementation. In one embodiment, the first resistive element 622 has a resistance in the range of about 90 ohms to about 110 ohms. In one embodiment, the first resistive element 622 has a resistance in the range of about 97 ohms to about 104 ohms. In one embodiment, the resistive element 622 is 102.9 ohms and has a power rating of 1 watt. The determination of the necessary resistance is based at least partially on the capacity of the voltage source, the voltage level of the voltage source, and the desired temporal length of the drainage curve. For example, in one embodiment the battery capacity of the first grouping of cells 610 is 1400 mAh, the voltage level is 6 VDC, and the target drain time is 24 hours. Diving 1400 mAh by 24 hours yields a current of 0.0582 A. Using Ohm's law, 6 V divided by 0.582 A yields a resistance of 102.9 ohms. With a current of 0.583 and a resistance of 102.9 ohms, the power dissipated by the resistor is 0.350 W. As is to be appreciated, different voltage levels, battery capacities, and desired time of discharge will result in different resistance values.

FIG. 49B is a simplified circuit diagram of yet another embodiment of a battery unit. In FIG. 49B, a battery unit 660 is attachable to a surgical instrument 650 having multiple sets of contacts. As illustrated, the surgical instrument 650 has a first set of contacts 652A, 652B and a second set of contacts 654A, 654B. The battery unit 660 has a first set of contacts 656A, 656B and a second set of contacts 658A, 658B configured to engage the contacts of the surgical instrument 650. In the illustrated embodiment, the battery unit 660 comprises a first cell 662 in series with a second cell 664 that supply power to the surgical instrument 650 through its first set of contacts 652A, 652B. The battery unit 660 may also comprises a third cell 668 in series with a fourth cell 670 that supply power to the surgical instrument 650 through its second set of contacts 654A, 654B. The first, second, third and fourth cells 662, 664, 668, 670 may each provide any suitable voltage level when fully charged, such as 3 VDC or 6 VDC, for example. In one embodiment, the battery unit 660 delivers a total of about 12 VDC to the surgical instrument 650 when the battery unit is fully charged (e.g., about 6 VDC via the first set of contacts 656A, 656B and about 6 VDV via the second set of contacts 658A, 658B). The battery unit 660 may comprise a first drain 672 and a second drain 674. While the first drain 672 and the second drain 674 are schematically illustrated separately in FIG. 49A, it is to be appreciated that the drains 672 and 674 may be implemented on a single circuit board, or through any other suitable implementation. The first drain 672 comprises a first resistive element 674 that is connected in a series arrangement with the first and second cells 662, 664 and a first switch 680. The second drain 674 comprises a second resistive element 682 that is connected in a series arrangement with the third and fourth cells 668, 670 and a second switch 684. The first and second switches 680, 684 are illustrated in an open position. When the first switch 680 is closed (e.g., during attachment of the battery unit 660 to the surgical instrument 650), current flows from the first and second cells 662, 664 through the first resistive element 678 to discharge those cells. Similarly, when the second switch 684 is closed (e.g., during attachment of the battery unit 660 to the surgical instrument 650), current flows from the third and fourth cells 668, 670 through the first resistive element 678 those cells.

FIG. 50 is a simplified circuit diagram of a battery unit 716 comprising a first drain 712 and a second drain 713. The battery unit 716 may be attached to an instrument 500, for example, via its contacts 718. In this embodiment, the battery unit 716 comprises a first grouping of cells 710, a second grouping of cells 711, and a third cell 714. The first drain 712 comprises a first resistive element 722 and a second resistive element 724. The second drain 713 comprises a third resistive element 726. The resistive elements 722, 724, 726 are coupled to respective cells through switches 730, 736, and 738. The switches 730, 736, and 738 may be closed upon attachment of the battery unit 716 to the surgical instrument 500 in order to initiate the draining of the first and second grouping of cells 610, 611 and the third cell 716. The resistance of the third resistive element 726 may be similar or different from the resistances of the first and second resistive element 722, 724. As described above, the resistance of the third resistive element 726 may at least partially depend on the voltage of the third cell 714 and the desired characteristics of the drainage curve.

FIGS. 51-53 are perspective views of a battery unit 800 implementing the schematic of the battery unit 616 shown in FIG. 49. The battery unit 800 may comprise a casing 802 defining an interior cavity 810. While the interior cavity 810 is illustrated in a central portion of the casing 802, it is to be appreciated that the internal cavity 810 may be positioned in any suitable location. The casing 802 may be covered by a cap 804 that may be secured to the casing 802 utilizing one or more mechanical latches 806, 808. FIG. 52 illustrates one embodiment of the battery unit 800 with the cap 804 removed to show a plurality of cells 812 within. Any suitable number and/or type of cells 812 may be used. For example, CR123 and/or CR2 cells may be used. FIG. 53 illustrates one embodiment of the battery unit 800 with a portion of the casing 802 removed to reveal the cells 812.

FIGS. 54A and 54B illustrate cross-sectional views of one embodiment of the battery unit 800 including a translatable drain 812. The drain 812 may be positioned within the interior cavity 810 and may be translatable within the interior cavity 810 in the directions of arrow 815. FIGS. 54A shows the drain 812 in an open position and FIG. 54B shows the drain 812 in a closed position. The drain 812 may comprise at least two contacts 816, 818. When the drain 812 is in the open position, a portion of the contacts 816, 818 may touch a non-conductive portion of the casing 802, such as fingers 820, 822. According to various embodiments, the contacts 816, 818 may be biased to exert a force against the fingers 820, 822 in order to resist movement of the drain 812 in the direction of the arrows 815. Also, in some embodiments, the fingers 820, 822 may define one or more protrusions or stepped down portions, as shown in FIGS. 54A and 54B. The battery unit 800 may also comprise one or more electrodes, such as first electrode 824 and second electrode 826. The first and second electrodes 824 and 826 may each be electrically coupled to a cathode or an anode of cells contained within the battery unit 800. In the closed position (FIG. 54B), the contacts 816, 818 are in electrical connection with the electrodes 824, 826, thereby allowing the voltage source to discharge through the drain 812. As discussed in more detail below, the drain 812 may be translated from the open position to the closed position upon attachment of the battery unit 800 to a surgical instrument.

FIG. 55 is a perspective view of the drain 812 in accordance with one non-limiting embodiment. The contacts 816, 818 of the drain 812 may be coupled to a base portion 830 of the drain 812. Similarly contacts 836, 838 of the drain 812 may be coupled to the base portion 830 of the drain 812. According to various embodiments, the contacts 816, 818 may be electrically connected to one another via a resistive element (not shown) mounted to a circuit board 832. Similarly, the contacts 836, 838 may be electrically connected to one another via a resistive element mounted to the circuit board 832. As illustrated, the contacts 816, 818, 836, 838 may have a bend or curvature to bias the contacts towards an outward position when they are inwardly compressed. Additionally, in one embodiment, the distal end of each of the contacts 816, 818, 836, 838 may have an inwardly turned section. The base portion 830 may comprise a contacting surface 840 that engages the instrument when the battery unit 800 is attached to the instrument. Through this engagement, the drain 812 may be translated relative to the casing 800.

FIG. 56 illustrates the battery unit 800 attached to a battery dock 850. For clarity, various components have been removed. Referring now to FIGS. 54A, 54B, 55 and 56, the battery dock 850 comprises a protruding member 858 sized to be received by the cavity 810 (FIG. 51) of the battery unit 800. Prior to attachment, the drain 812 is in the open position (FIG. 54A). During attachment of the battery unit 800 to the battery dock 850, the protruding member 858 is inserted into the cavity 810 and the battery unit 800 is moved relative to the battery dock 850 in the direction indicated by arrow 862. Eventually the distal end 860 of the protruding member 858 contacts the contacting surface 840 of the drain 812. As the user continues to attach the battery unit 800, the drain 812 is translated relative to the casing 802 in the direction indicated by arrow 864 and moves into the closed position (FIG. 54B). In this position, the battery unit 800 commences to slowly drain. When the battery unit 800 is removed from the battery dock 850, the drain 812 may remain in the position shown in FIG. 54B. In this way, the cells (not shown) of the battery unit 800 may drain any remaining charge across a resistive element either before or during disposal.

As is to be appreciated, the translatable discharge drain of the battery unit is not limited the implementation illustrated in FIG. 56. FIGS. 57A and 57B, for example, illustrate a battery unit 900 and drain 912 with various components removed for clarity. The drain 912 that is translatable between an open position (FIG. 57A) and a closed position (FIG. 57B). In the open position, contacts 916, 918 are engaged with non-conductive portions of a casing 920, 922, respectively. The drain 912 may ride in a track 914 when translating between the open position and the closed position. FIG. 57B shows the battery unit 900 in a closed position after a ram 958 has translated the drain 912 in the direction indicated by arrow 964. The ram 958 may be a component of a battery dock of a surgical instrument, for example. In one embodiment, the battery dock comprises a cavity that is dimensioned to receive the battery unit 900, and the ram 958 is positioned within the cavity. In the closed position, the contacts 916, 918 are in electrical contact with electrodes 924, 926. The drain 912 may comprise a printed circuit board 932 to which at least one resistive element is mounted using a surface mount or a through-hole connection, for example.

FIGS. 58A and 58B illustrate a battery unit 1000 in accordance with another non-limiting embodiment. Various components have been omitted for clarity. The battery unit 1000 comprises a drain 1012 that is translatable between an open position (FIG. 58A) and a closed position (FIG. 58B). The battery unit 1000 may comprise a first electrode 1024 with a contact 1025 and a second electrode 1026 with a contact 1027. The electrodes 1024, 1026 may be in contact with cells (not shown) of the battery unit 1000. In the open position, contacts 1016, 1018 of the drain 1012 are not engaged with contacts 1025, 1027 of the electrodes 1024, 1026. The drain 1012 may ride in a track 1014 when translating between the open position and the closed position. FIG. 58B shows the battery unit 1000 in a closed position after a ram 1058 has translated the drain 1012 in the direction indicated by arrow 1064. The ram 1058 may be a component of a battery dock of a surgical instrument, for example. In the closed position, the contacts 1016, 1018 of the drain 1012 are in electrical contact with the contacts 1025, 1027 of the electrodes 1024, 1026. The drain 1012 may comprise a printed circuit board 1032 that includes at least one resistive element. In some embodiments, the contacts 1016, 1018 themselves may comprise the resistive elements. In fact, the resistive elements may be elements of any suitable resistance value and any suitable mechanical configuration.

FIG. 59 is a perspective view of a battery unit 1100. FIGS. 60A and 60B show internals views of the battery unit 1100 during various stages of operation with various components removed for clarity. The battery unit 1100 has one cell 1102 and an outer casing 1104 that defines a cavity 1110. The outer casing 1104 may be non-conductive and have conductive contacts for supplying energy to circuitry of a surgical instrument when the battery unit 1100 is attached to a surgical instrument. In one embodiment, the battery unit 1100 is received by a cavity in a pistol grip portion of a surgical instrument. The battery unit 1100 comprises a drain 1112 that is translatable between an open position (FIG. 60A) and a closed position (FIG. 60B). In one embodiment the drain 1112 has first and second contacts 1116, 1118 that are coupled to a circuit board 1132. The circuit board 1132 may include, for example, at least one resistive element. In some embodiments, the circuit board 1132 includes additional circuitry. The battery unit 1100 comprises a first electrode 1124 coupled to an anode of the cell 1102 and a second electrode coupled to a cathode of the cell 1102. Before the battery unit 1100 is attached to an instrument, the drain 1112 is in the open position (FIG. 60A). In the illustrated embodiment, the first contact 1116 is electrically coupled to the first electrode 1124 and the second contact 1118 is resting on, or otherwise contacting, a non-conductive finger 1120. As the battery unit 1100 is attached to an instrument, a protruding portion 1158 of the instrument may be received by the cavity 1110 and contact the drain 1112 to drive the drain 1112 in the direction indicated by the arrow 1164. In the closed position (FIG. 60B) the first contact 1116 is electrically coupled to the first electrode 1124 and the second contact 1118 is electrically coupled to the second electrode 1126. In this position, a closed circuit is created that allows the cell 1102 to discharge energy through the drain 1112.

Additional details regarding surgical instruments and battery units are described in U.S. patent application Ser. No. 12/884,838, entitled "SURGICAL INSTRUMENTS AND BATTERIES FOR SURGICAL INSTRUMENTS," filed Sep. 17, 2010, and incorporated herein by reference in its entirety.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument comprising:
   an end effector;
   a handle operatively coupled to the end effector, wherein the handle comprises a trigger to actuate the end effector, the handle comprising a battery dock;
   the battery dock comprising a protruding member; and
   a battery unit attachable to the battery dock, wherein the battery unit is in electrical contact with at least one of the handle and the end effector when attached to the battery dock, and wherein the battery unit comprises:
      a casing;
      an anode and a first cathode positioned within the casing; and
      a translatable discharge drain, wherein, upon attachment of the battery unit to the battery dock, the protruding member contacts the discharge drain and the discharge drain translates with respect to casing to electrically couple the first anode of the battery unit to the first cathode of the battery unit.

2. The surgical instrument of claim 1, wherein the discharge drain comprises a first contact and a second contact, and at least one resistive element electrically coupled to the first and second contact, wherein, upon attachment of the battery unit to the battery dock, the discharge drain electrically couples the anode to the cathode through the at least one resistive element.

3. The surgical system of claim 2, wherein the at least one resistive element has a resistance in the range of about 90 ohms to about 110 ohms.

4. The surgical instrument of claim 1, wherein the anode comprises a first anode and the cathode comprises a first cathode, wherein the battery unit comprises a second anode and a second cathode positioned within the casing and wherein, upon attachment of the battery unit to the battery dock, the discharge drain electrically couples the second anode to the second cathode.

5. The surgical instrument of claim 1, wherein the end effector comprises at least one implement selected from the group consisting of: a cutter, a clasper, a stapler, an RF implement, an ultrasonic implement, and a laser implement.

6. The surgical instrument of claim 1, wherein the battery unit comprises at least one cell selected from the group consisting of a CR123 cell and a CR2 cell.

7. A surgical system comprising:
   a surgical instrument comprising a battery compartment;
   a protruding member positioned proximate the battery compartment; and
   a battery unit, wherein the battery unit comprises:
      a casing;
      a plurality of cells positioned within the casing, wherein at least a portion of the plurality of cells are not electrically connected to one another; and
      a discharge switch having an open position and a closed position, wherein, when in the closed position, the discharge switch electrically couples an anode of the battery unit to a cathode of the battery unit, wherein the discharge switch is mechanically biased towards the closed position, wherein the discharge switch is held in the open position by a non-conductive portion of the casing, and wherein the discharge switch is translated into the closed position by the protruding member upon attachment of the battery unit into the battery compartment of the surgical instrument.

8. The surgical system of claim 7, wherein the end effector comprises at least one implement selected from the group consisting of: a cutter, a clasper, a stapler, an RF sealing implement, and an ultrasonic implement.

9. The surgical system of claim 7, wherein the discharge switch translates relative to the non-conductive portion of the casing upon attachment of the battery unit into the battery compartment of the surgical instrument.

10. The surgical system of claim 9, wherein the non-conduction portion of the casing comprises a non-conductive finger.

11. The surgical system of claim 7, wherein the discharge switch comprises a circuit board and at least one resistive element is mounted to the circuit board and electrically coupled to at least one cell when the discharge switch is in the closed position.

12. The surgical system of claim 7, wherein the casing defines a cavity dimensioned to receive the protruding member.

13. The surgical system of claim 7, wherein the plurality of cells comprises at least one cell selected from the group consisting of a CR123 cell and a CR2 cell.

14. A surgical system comprising:
   a surgical device comprising a battery dock; and
   a battery unit, wherein the battery unit comprises:
      a first and second grouping of cells; and
      a translatable battery drain positioned proximate the first and second grouping of cells; wherein the translatable battery drain comprises a first and second set of contacts; wherein, in a first position, the first and second set of contacts are not electrically coupled to the first and second grouping of cells; and wherein, in a second position, the first set of contacts is electrically coupled to the first grouping of cells and the second set of contacts is electrically coupled to the second grouping of cells; wherein the translatable battery drain translates from the first position to the second position upon attachment of the battery unit to the battery dock.

15. The surgical system of claim 14, wherein the battery unit comprises at a first conductive path and a second conductive path, wherein the first and second contacts engage the first and second conductive paths, respectively, upon attachment of the battery unit to the battery dock.

16. The surgical system of claim 14, wherein the battery dock comprises a ram dimensioned to engage the translatable battery drain.

17. The surgical system of claim 14, wherein the translatable battery drain comprises first and second resistive elements, wherein the first set of contacts are electrically coupled to the first resistive element and the second set of contacts are electrically coupled to the second resistive element.

18. The surgical system of claim 17, wherein the first and second resistive elements each have a resistance in the range of about 90 ohms to about 110 ohms.

19. The surgical system of claim 14, wherein the first and second grouping of cells each comprise at least one cell selected from the group consisting of a CR123 cell and a CR2 cell.

20. The surgical system of claim 14, comprising a locking cam, the locking cam comprising a body portion and a spring portion pivotable with respect to the body portion.

* * * * *